United States Patent
Miikkulainen et al.

(10) Patent No.: US 11,403,532 B2
(45) Date of Patent: Aug. 2, 2022

(54) METHOD AND SYSTEM FOR FINDING A SOLUTION TO A PROVIDED PROBLEM BY SELECTING A WINNER IN EVOLUTIONARY OPTIMIZATION OF A GENETIC ALGORITHM

(71) Applicant: Cognizant Technology Solutions U.S. Corporation, College Station, TX (US)

(72) Inventors: Risto Miikkulainen, Stanford, CA (US); Hormoz Shahrzad, Dublin, CA (US); Nigel Duffy, San Francisco, CA (US); Philip M. Long, Palo Alto, CA (US)

(73) Assignee: Cognizant Technology Solutions U.S. Corporation, College Station, TX (US)

( * ) Notice: Subject to any disclaimer, the term of this patent is extended or adjusted under 35 U.S.C. 154(b) by 855 days.

(21) Appl. No.: 15/911,048

(22) Filed: Mar. 2, 2018

(65) Prior Publication Data
US 2018/0253649 A1    Sep. 6, 2018

Related U.S. Application Data

(60) Provisional application No. 62/466,227, filed on Mar. 2, 2017.

(51) Int. Cl.
*G06N 3/12* (2006.01)
*G16B 40/00* (2019.01)
(Continued)

(52) U.S. Cl.
CPC ......... *G06N 3/126* (2013.01); *G06Q 30/0242* (2013.01); *G06Q 30/0243* (2013.01);
(Continued)

(58) Field of Classification Search
CPC .... G06N 3/126; G16B 40/00; G06Q 30/0242; G06Q 30/0243; G06Q 30/0244; G06Q 30/0277
See application file for complete search history.

(56) References Cited

U.S. PATENT DOCUMENTS

| | | | |
|---|---|---|---|
| 4,935,877 A | 6/1990 | Koza | |
| 4,950,270 A | 8/1990 | Bowman et al. | |

(Continued)

FOREIGN PATENT DOCUMENTS

| | | |
|---|---|---|
| EP | 2422276 | 2/2012 |
| EP | 2422278 | 2/2012 |

(Continued)

OTHER PUBLICATIONS

Jenna Carr, An Introduction to Genetic Algorithms, May 2014 (Year: 2014).*

(Continued)

*Primary Examiner* — Omar F Fernandez Rivas
*Assistant Examiner* — Selene A. Haedi
(74) *Attorney, Agent, or Firm* — Dawn-Marie Bey; Bey & Cotropia PLLC

(57) ABSTRACT

A method for finding a solution to a problem is provided. The method includes storing candidate individuals in a candidate pool and evolving the candidate individuals by performing steps including (i) testing each of the candidate individuals to obtain test results, (ii) assigning a performance measure to the tested candidate individuals, (iii) discarding candidate individuals from the candidate pool in dependence upon their assigned performance measure, and (iv) adding, to the candidate pool, a new candidate individual procreated from candidate individuals remaining in the candidate pool. The method further includes selecting, as the winning candidate individual, a candidate individual (Continued)

having a best neighborhood performance measure, where the neighborhood performance measure of a particular candidate individual is given by the performance measures of (i) the particular candidate individual and (ii) K neighborhood candidate individuals which are nearest in the candidate pool to the particular candidate individual, and where K>0.

**21 Claims, 22 Drawing Sheets
(5 of 22 Drawing Sheet(s) Filed in Color)**

(51) Int. Cl.
*G06Q 30/02* (2012.01)
*G16B 40/20* (2019.01)

(52) U.S. Cl.
CPC ..... *G06Q 30/0244* (2013.01); *G06Q 30/0277* (2013.01); *G16B 40/00* (2019.02); *G16B 40/20* (2019.02)

(56) References Cited

U.S. PATENT DOCUMENTS

| | | |
|---|---|---|
| 5,136,686 A | 8/1992 | Koza |
| 5,343,554 A | 8/1994 | Koza et al. |
| 5,568,590 A | 10/1996 | Tolson |
| 5,761,381 A | 6/1998 | Arci et al. |
| 5,845,266 A | 12/1998 | Lupien et al. |
| 5,849,013 A | 12/1998 | Whittaker et al. |
| 5,860,978 A | 1/1999 | McDevitt et al. |
| 5,867,397 A | 2/1999 | Koza et al. |
| 5,920,848 A | 7/1999 | Schutzer et al. |
| 5,930,780 A | 7/1999 | Hughes et al. |
| 5,968,045 A | 10/1999 | Frazier |
| 5,970,487 A | 10/1999 | Shackleford et al. |
| 6,001,100 A | 12/1999 | Sherman et al. |
| 6,010,503 A | 1/2000 | Richelsoph et al. |
| 6,059,818 A | 5/2000 | Johnson et al. |
| 6,088,690 A | 7/2000 | Gounares et al. |
| 6,240,399 B1 | 5/2001 | Frank et al. |
| 6,249,783 B1 | 6/2001 | Crone et al. |
| 6,302,886 B1 | 10/2001 | McDevitt et al. |
| 6,523,016 B1 | 2/2003 | Michalski |
| 6,730,124 B2 | 5/2004 | Steiner |
| 6,890,354 B2 | 5/2005 | Steiner et al. |
| 6,957,200 B2 | 10/2005 | Buczak et al. |
| 7,013,344 B2 | 3/2006 | Megiddo |
| 7,016,882 B2 | 3/2006 | Afeyan et al. |
| 7,035,740 B2 | 4/2006 | Kermani |
| 7,047,169 B2 | 5/2006 | Pelikan et al. |
| 7,137,996 B2 | 11/2006 | Steiner et al. |
| 7,141,066 B2 | 11/2006 | Steiner et al. |
| 7,201,773 B2 | 4/2007 | Steiner et al. |
| 7,353,184 B2 | 4/2008 | Kirschenbaum et al. |
| 7,356,518 B2 | 4/2008 | Bonabeau et al. |
| 7,370,013 B1 | 5/2008 | Aziz et al. |
| 7,444,309 B2 | 10/2008 | Branke et al. |
| 7,603,326 B2 | 10/2009 | Bonabeau et al. |
| 7,624,077 B2 | 11/2009 | Bonabeau et al. |
| 7,707,220 B2 | 4/2010 | Bonabeau et al. |
| 7,882,048 B2 | 2/2011 | Bonabeau et al. |
| 8,062,295 B2 | 11/2011 | McDevitt et al. |
| 8,110,001 B2 | 2/2012 | Carter et al. |
| 8,117,139 B2 | 2/2012 | Bonabeau et al. |
| 8,117,140 B2 | 2/2012 | Bonabeau et al. |
| 8,423,323 B2 | 4/2013 | Bonabeau |
| 8,527,433 B2 | 9/2013 | Hodjat et al. |
| 8,775,341 B1 | 7/2014 | Commons |
| 8,805,715 B1 | 8/2014 | Jones et al. |
| 8,868,446 B2 | 10/2014 | Lamoureux et al. |
| 8,909,570 B1 | 12/2014 | Hodjat et al. |
| 8,918,349 B2 | 12/2014 | Hodjat et al. |
| 9,002,729 B2 | 4/2015 | Natoli et al. |
| 9,008,416 B2 | 4/2015 | Movellan et al. |
| 9,104,978 B2 | 8/2015 | Zeine et al. |
| 9,256,837 B1 | 2/2016 | Hodjat et al. |
| 9,304,895 B1 | 4/2016 | Shahrzad et al. |
| 9,311,383 B1 | 4/2016 | Karty et al. |
| 9,367,816 B1 | 6/2016 | Demaneuf et al. |
| RE46,178 E | 10/2016 | Afeyan et al. |
| 9,466,023 B1 | 10/2016 | Shahrzad et al. |
| 9,684,875 B1 | 6/2017 | Hodjat et al. |
| 9,734,215 B2 | 8/2017 | Hodjat et al. |
| 2002/0019844 A1 | 2/2002 | Kurowski et al. |
| 2002/0082077 A1 | 6/2002 | Johnson et al. |
| 2003/0078585 A1 | 4/2003 | Johnson et al. |
| 2003/0158887 A1 | 8/2003 | Megiddo |
| 2003/0216780 A1 | 11/2003 | Fitts et al. |
| 2004/0002735 A1 | 1/2004 | Lizardi et al. |
| 2004/0025109 A1 | 2/2004 | Harrington et al. |
| 2004/0122785 A1 | 6/2004 | Brown et al. |
| 2004/0143559 A1 | 7/2004 | Ayala |
| 2004/0210545 A1 | 10/2004 | Branke et al. |
| 2004/0254901 A1 | 12/2004 | Bonabeau et al. |
| 2005/0033672 A1 | 2/2005 | Lasry et al. |
| 2005/0159812 A1 | 7/2005 | Dinger et al. |
| 2005/0187848 A1 | 8/2005 | Bonissone et al. |
| 2005/0198103 A1 | 9/2005 | Ching |
| 2005/0203621 A1 | 9/2005 | Steiner et al. |
| 2006/0089646 A1 | 4/2006 | Bonutti |
| 2006/0103667 A1 | 5/2006 | Amit et al. |
| 2006/0225003 A1 | 10/2006 | Agogino et al. |
| 2007/0094072 A1 | 4/2007 | Vidals et al. |
| 2007/0094168 A1 | 4/2007 | Ayala et al. |
| 2007/0100907 A1 | 5/2007 | Bayer |
| 2007/0143198 A1 | 6/2007 | Brandes et al. |
| 2007/0143759 A1 | 6/2007 | Ozgur et al. |
| 2007/0185990 A1 | 8/2007 | Ono et al. |
| 2007/0239632 A1 | 10/2007 | Burges et al. |
| 2007/0298866 A1 | 12/2007 | Gaudiano et al. |
| 2008/0071588 A1 | 3/2008 | Eder |
| 2008/0086138 A1 | 4/2008 | Stone et al. |
| 2008/0209320 A1 | 8/2008 | Mawhinney et al. |
| 2008/0228271 A1 | 9/2008 | Stone et al. |
| 2008/0228644 A1 | 9/2008 | Birkestrand et al. |
| 2009/0030859 A1 | 1/2009 | Buchs et al. |
| 2009/0125370 A1 | 5/2009 | Blondeau et al. |
| 2009/0259534 A1 | 10/2009 | Utter et al. |
| 2009/0307638 A1 | 12/2009 | McConaghy |
| 2009/0327913 A1 | 12/2009 | Adar et al. |
| 2010/0003640 A1 | 1/2010 | Damstra et al. |
| 2010/0030720 A1 | 2/2010 | Stephens |
| 2010/0082104 A1 | 4/2010 | Carter et al. |
| 2010/0169234 A1 | 7/2010 | Metzger et al. |
| 2010/0182935 A1 | 7/2010 | David |
| 2010/0274355 A1 | 10/2010 | McGuire et al. |
| 2010/0274736 A1 | 10/2010 | Hodjat et al. |
| 2010/0274742 A1 | 10/2010 | Hodjat et al. |
| 2010/0293119 A1 | 11/2010 | Ferringer et al. |
| 2010/0324676 A1 | 12/2010 | Albertorio et al. |
| 2011/0066185 A1 | 3/2011 | Wotton, III |
| 2011/0161264 A1 | 6/2011 | Cantin |
| 2011/0179370 A1 | 7/2011 | Cardno et al. |
| 2011/0261049 A1 | 10/2011 | Cardno et al. |
| 2012/0150626 A1* | 6/2012 | Zhang ............... G06Q 30/0243 705/14.42 |
| 2012/0239517 A1 | 9/2012 | Blondeau et al. |
| 2012/0303564 A1 | 11/2012 | Dobson et al. |
| 2013/0024290 A1 | 1/2013 | Berg et al. |
| 2013/0116730 A1 | 5/2013 | Denham et al. |
| 2013/0124440 A1 | 5/2013 | Hodjat et al. |
| 2013/0218821 A1 | 8/2013 | Szatmary et al. |
| 2013/0254036 A1 | 9/2013 | Trinh et al. |
| 2013/0254142 A1 | 9/2013 | Hodjat et al. |
| 2013/0282626 A1 | 10/2013 | White et al. |
| 2014/0006316 A1 | 1/2014 | Hodjat et al. |
| 2014/0067514 A1 | 3/2014 | Vitti et al. |
| 2014/0067516 A1 | 3/2014 | Price et al. |
| 2014/0075004 A1 | 3/2014 | Van Dusen et al. |
| 2014/0075336 A1 | 3/2014 | Curtis et al. |
| 2014/0189714 A1 | 7/2014 | Lawbaugh et al. |
| 2014/0236875 A1 | 8/2014 | Phillipps et al. |
| 2014/0257346 A1 | 9/2014 | Sengun et al. |

(56) References Cited

U.S. PATENT DOCUMENTS

| | | | |
|---|---|---|---|
| 2014/0279203 A1 | 9/2014 | Malek et al. | |
| 2014/0321737 A1 | 10/2014 | Movellan et al. | |
| 2014/0344013 A1 | 11/2014 | Karty et al. | |
| 2014/0372344 A1 | 12/2014 | Morris et al. | |
| 2015/0006442 A1 | 1/2015 | Ogilvie et al. | |
| 2015/0019173 A1 | 1/2015 | Amid et al. | |
| 2015/0039026 A1 | 2/2015 | Pasquali et al. | |
| 2015/0095756 A1 | 4/2015 | Aganovic et al. | |
| 2015/0157449 A1 | 6/2015 | Gustafson et al. | |
| 2015/0254328 A1 | 9/2015 | Dereszynski et al. | |
| 2016/0081790 A1 | 3/2016 | Coumoyer et al. ... | A61F 1/0811 |
| 2016/0321716 A1 | 11/2016 | Ravikant et al. | |
| 2017/0039198 A1 | 2/2017 | Ramamurthy et al. | |
| 2017/0060963 A1 | 3/2017 | Whittaker et al. | |
| 2017/0124600 A1 | 5/2017 | Katzen et al. | |
| 2017/0132553 A1 | 5/2017 | Theirl et al. | |
| 2017/0193366 A1 | 7/2017 | Miikkulainen et al. | |
| 2017/0193367 A1 | 7/2017 | Miikkulainen et al. | |
| 2017/0193403 A1 | 7/2017 | Iscoe et al. | |
| 2017/0300966 A1 | 10/2017 | Dereszynski et al. | |
| 2017/0323219 A1 | 11/2017 | Shahrzad et al. | |
| 2018/0253649 A1 | 9/2018 | Miikkulainen et al. | |

FOREIGN PATENT DOCUMENTS

| | | | |
|---|---|---|---|
| JP | 08-110804 | 4/1996 | |
| JP | 2001325041 | 11/2001 | |
| JP | 2003044665 | 2/2003 | |
| JP | 2004240671 | 8/2004 | |
| JP | 2004302741 | 10/2004 | |
| JP | 2007207173 | 8/2007 | |
| JP | 2007522547 | 8/2007 | |
| WO | WO 2016/207731 | 12/1916 | |
| WO | WO 2000/002138 | 1/2000 | |
| WO | WO-0002138 A1 * | 1/2000 | ............ G06Q 30/02 |
| WO | WO 2005/073854 | 8/2005 | |
| WO | WO 2010/127039 | 11/2010 | |
| WO | WO 2010/127042 | 11/2010 | |

OTHER PUBLICATIONS

L. Darrell Whitley, Andrew M. Sutton. Partial Neighborhoods of Elementary Landscapes. 2009. ACM. (Year: 2009).*

Janez Demšar. Statistical Comparisons of Classifiers over Multiple Data Sets. 2006. Journal of Machine Learning Research. (Year: 2006).*

Cheng et. al. "A Reference Vector Guided Evolutionary Algorithm for Many-Objective Optimization", Oct. 2016 (Year: 2016).*

Tan et. al., "Evolutionary Algorithms With Dynamic Population Size and Local Exploration for Multiobjective Optimization", Dec. 2001 (Year: 2001).*

U.S. Appl. No. 15/399,450—Office Action dated Jul. 30, 2019, 51 pp.

Shrivastava, et al., A Review on Web Recommendation System, International Journal of Computer Applications (0975-8887) vol. 83—No. 17, Dec. 2013, pp. 14-17 (Year: 2013).

PCT/IB17/050044—International Preliminary Report on Patentability, dated Jul. 10, 2018, 10 pp.

PCT/IB17/050043—International Preliminary Report on Patentability, dated Jul. 10, 2018, 7 pp.

PCT/IB17/050043—International Search Report and Written Opinion, dated May 24, 2017, 17 pp.

PCT/IB17/50044—International Search Report and Written Opinion dated Jun. 1, 2017, 21 pages.

"It's All A/Bout Testing: The Netflix Experimentation Platform" [online], Apr. 29, 2016 [Retrieved Jun. 28, 2020], Netflix Technology Blog, Retrieved from the Internet: https://netflixtechblog.com/its-all-a-bout-testing-the-netflix-experimentation-platform-4e1ca458c15, 10 pp.

"Look Inside4 a 1,024 Recipe Multivariate Experiment" [online], Aug. 13, 2009 [retrieved on Jun. 28, 2020], 4 pp., Retrieved from the Internet: https://youtube.googleblog.com/2009/08/look-inside-1024-recipe-multivariate.html.

"Product Integration Testing at the Speed of Netflix" [online], Jul. 5, 2016 [retrieved Jun. 28, 2020], Netflix Technology Blog, 9 pp., Retrieved from the Internet: https://netflixtechblog.com/product-integration-testing-at-the-speed-of-netflix-72e4117734a7.

Nesamoney, Diaz, "Personalized Digital Advertising", 2015, cover page through p. 6 and Index, 34 pages.

Chris Saint-Amant, "Scaling A/B Testing on Netflix.com With Node.js" [on line], Aug. 18, 2014 [retrieved Jun. 28, 2020], Netflix Technology Blog, 3 pp., Retrieved from the Internet: https://netflixtechblog/sacling-a-b-testing-on-netflix-com-with-node-js-5938101c00fc.

Baveye, Automatic Prediction of Emotions Induced by Movies, Doctoral Thesis, University of Lyon, 2015, pp. 1-162 (Year: 2015).

U.S. Appl. No. 15/399,433—Office Action dated Aug. 30, 2018, 29 pages.

U.S. Appl. No. 15/399,433—Preliminary Amendment dated Jan. 3, 2018, 7 pages.

U.S. Appl. No. 15/399,433—Response to Office Action dated Aug. 30, 2018, filed Feb. 28, 2019, 11 pages.

U.S. Appl. No. 15/399,433—Notice of Allowance, dated Apr. 3, 2019, 19 pp.

Marks, P. H., "Rigidfix™ ACL Cross Pin System," 1999, Surgical Technique guide (4 pages).

"ACL Graft Choices" [online], 2008 [retrieved on Jun. 28, 2020], Centers for Orthopaedics, 10 pp., https://web.archive.org/web/20150810131913/http:/www.orthoassociates.com/SP11B35/.

Edgar, C. M., et al., "Prospective Comparison of Auto and Allograft Hamstring Tendon Constructs for ACL Reconstruction," Clin. Orthop. Relat. Res., 2008, 2238-2246. (9 pages).

Shahrzad, et al., "Estimating the Advantage of Age-Layering in Evolutionary Algorithms," in Proceedings of the Genetic and Evolutionary Computation Conference (GECCO-2016), Denver, CO, 2016.

Kohavi, et al., "Online Controlled Experiments and A/B Tests," 2015.

Shahrzad, et al. "Nonparametric Functional Estimation," 2014.

"κ-means clustering" [online], Wikipedia, [retrieved on Apr. 4, 2019], Retrieved from the Internet: http://en.wikipedia.org/wiki/K-means_clustering, 13 pp.

"κ-medoids" [online], Wikipedia, [retrieved on Apr. 4, 2019], Retrieved from the Internet: http://en.wikipedia.org/wik/K-medoids, 6 pp.

Miikkulainen, et al., "Howto Select a Winner in Evolutionary Optimization?", IEEE Symposium Series in Computational Intelligence, 2017.

Shahrzad, et al., "Tackling the Boolean Multiplexer Function Using a Highly Distributed Genetic Programming System," in Genetic Programming Theory and Practice XII, 7 pp., 2015.

International Search Report and Written Opinion for PCT Application No. PCTG/US18/66610, dated Apr. 15, 2019, 8 pp.

U.S. Appl. No. 13/358,381—Office Action dated Jul. 8, 2014, 30 pp.

Freitas, A., "A review of evolutionary algorithms for data mining," Soft Computing for Knowledge Discovery and Data Mining, Springer US, 2008 pp. 79-111.

U.S. Appl. No. 13/540,507—Office Action dated Sep. 9, 2014, 25 pp.

Bongard, J. C. et al., "Guarding Against Premature Convergence while Accelerating Evolutionary Search", GECCO'10: Proceedings of the 12th annual conference on Genetic and Evolutionary Computation, 8 pages (2010).

Hornby, Gregory S.; "The Age-Layered Population Structure (ALPS) Evolutionary Algorithm"; 2009; ACM; GECCO '09; 7 pages.

Gaspar-Cunha, A. et al., "A Multi-Objective Evolutionary Algorithm Using Neural Networks to Approximate Fitness Evaluations," Int'l J. Computers, Systems and Signals, 6(1) 2005, pp. 18-36.

Kosorukofi, A. "Using incremental evaluation and adaptive choice of operators in a genetic algorithm," Proc. Genetic and Evolutionary Computation Conference, GECCO—Sep. 2002, 7pp.

Nelson, A. "Fitness functions in evolutionary robotics: A survey and analysis," Robotics and Autonomous Systems 57 (Apr. 30, 2009) 345-370.

(56) References Cited

OTHER PUBLICATIONS

Wu, A. S., et al., "An incremental fitness function for partitioning parallel tasks," Proc. Genetic and Evolutionary Computation Conf. (Aug. 2001), 8 pp.
Whitehead, B.A. "Genetic Evolution of Radial Basis Function Coverage Using Orthogonal Niches," IEEE Transactions on Neural Networks, 7:6, (Nov. 1996) 1525-28.
Bui L.T. et al., "Local models: an approach to distributed multi-objective optimization," Computational Optimization and Applications, vol. 42, No. 1, Oct. 2007, pp. 105-139.
Castillo Tapia M.G. et al., "Applications of multi-objective evolutionary algorithms in economics and finance: A survey," Proc. IEEE Congress on Evolutionary Computation, Sep. 2007, pp. 532-539.
Dutheyne, E. et al., "Is Fitness Inheritance Useful for Real-World Applications?" Evolutionary Multi-Criterion Optimization, ser. LNCS 2631, Spring 2003, pp. 31-42.
Enee, Gilles et al., "Classifier Systems Evolving Multi-Agent System with Distributed Elitism," Proc. 1999 Congress on Evolutionary Computation (CEW'99) vol. 3:6, Jul. 1999, pp. 1740-1746.
Gopalakiishnan, G. et al., "Optimal Sampling in a Noisy Genetic Algorithm for Risk-Based Remediation Design," Bridging the gap: meeting the world's water and environmental resources challenges, Proc. World Water Congress 2001, 8 pp.
Juille, H. "Evolution of Non-Deterministic Incremental Algorithms as a New Approach for Search in State Spaces," Proc. 6th Int'l Conf. on Genetic Algorithms, 1995, 8pp.
International Search Report dated Jul. 2, 2010 in PCT/US10/32847 (GNFN 2510-2).
International Search Report dated Jun. 29, 2010 in PCT/US10/32841.
Sacks, J. et al. "Design and Analysis of Computer Experiments," Statistical Science 4:4, 1989, 409-435.
Torresen, J. "A Dynamic Fitness Function Applied to Improve the Generalisation when Evolving a Signal Processing Hardware Architecture," Proc. EvoWorkshops 2002, 267-299 (12 pp).
Bartlett II, J.E. et al., "Organizational Research: Determining Appropriate Sample Size in Survey Research," IT, Learning, and Performance Journal 19(1) Spring 2001, 8pp.
Fitzpatrick, J.M. et al., "Genetic Algorithms in Noisy Environments," Machine Learning 3: 101-120, May 1988.
JP 2010-533295, Office Action dated Apr. 16, 2013, 3 pp.
León C. et al., "Parallel hypervolume-guided hyperheuristic for adapting the multi-objective evolutionary island model," Proc. 3rd Int'l Workshop on Nature Inspired Cooperative Strategies for Optimization Studies in Computational Intelligence, vol. 236, Nov. 2008, pp. 261-272.
López Jaimes A. et al., "MRMOGA: Parallel evolutionary multiobjective optimization using multiple resolutions," Proc. IEEE Congress on Evolutionary Computation, vol. 3, Sep. 2005, pp. 2294-2301.
Davarynejad, M. et al., "A Novel General Framework for Evolutionary Optimization: Adaptive Fuzzy Fitness Granulation," CEC Sep. 2007, 6pp.
Davarynejad, M. "Fuzzy Fitness Granulation in Evolutionary Algorithms for complex optimization," Master of Science Thesis, Ferdowsi Univ. of Mashhad, Jun. 2007, 30pp.
Salami, M. et al., "A fast evaluation strategy for evolutionary algorithms," Applied Soft Computing 2/3F (Jan. 2003) 156-173.
M.-R Akbarzadeh-T. et al., "Friendship Modeling for Cooperative Co-Evolutionary Fuzzy Systems: A Hybrid GA-GP Algorithm," Proc. 22nd Int'l Conf. of N American FIPS, Jul. 2003, pp. 61-66.
Mouret, J.B. et al., "Encouraging Behavioral Diversity in Evolutionary Robotics: An Empirical Study," MIT, Evolutionary Computation 20(1):91-133, 2012.
Myers, Raymond H. and Montgomery, Douglas C., Response Surface Methodology: Process and Product Optimization Using Designed Experiments, John Wiley and Sons, Inc., New York, 1995.
Poli R et al., "Genetic Programmig: An introductory Tutorial and a Survey of Techniques and Applications," Univ. Essex School of Computer Science and Eletronic Engineering Technical Report No. CES-475, Oct. 2007, 112 pp.

Georgilakis, P.S. "Genetic Algorithm Model for Profit Maximization of Generating Companies in Deregulated Electricity Markets," Applied Artificial IntellIgence, Jul. 2009, 23:6,538-552.
Refaeilzadeh, P. et al., "Cross Validation" entry, Encyclopedia of Database Systems; eds. Öznu and Liu, Springer, 2009, 6pp.
Remde, S. et al. "Evolution of Fitness Functions to Improve Heuristic Performance," LION Dec. 8-10, 2007 II, LNCS 5313 pp. 206-219.
Sakauchi et al., UNIFINE. A Next Generation Financial Solution System of Nihon Unisys Ltd., Technology Review 'Unisys,' Japan, Nihon Unisys Ltd., Feb. 28, 2006, vol. 25, No. 4, pp. 14-15.
Schoreels C., "Agent based Genetic Algorithm Employing Financial Technical Analysis for Making Trading De6sions Using Historical Equity Market Data," IEEE/WIC/ACM International Conference on Intelligent Agent Technology (IAT2004), Beijing, China, Sep. 20-24, 2004, pp. 421-424.
Streichert F., "introduction to Evolutionary Algorithms," paper to be presented Apr. 4, 2002 at the Frankfurt MathFinance Workshop Mar. 30, 2002, Frankfurt; Germany, XP55038571, 22 pp. (retrieved from the Internet: URL: http://www.ra.cs.uni-tuebingen.de/mita rb/streiche/publications/Introduction to E volutionary Algorithms.pdf).
Tanev, I. et al., "Scalable architecture for parallel distributed implementation of genetic programming on network of workstations," J. Systems Architecture, vol. 47, Jul. 2001, pp. 557-572.
Ahn, Chang Wook et al.; "Elitism-Based Compact Genetic Algorithms"; 2003; IEEE; Transactions on Evolutionary Computation, vol. 7, No. 4: pp. 367-385.
Hornby, G.S., "ALPS: The Age-Layered Population Structure for Reducing the Problem of Premature Convergence," GECCO'06, Seattle, Jul. 2006, authored by an employee or the US Government, therefore in the pubic domain, 8pp.
Hornby, G.S., "A Steady-State Version of the Age-Layered Population Structure EA," Chapter 1 of Genetic Programming Theory and Practice VII, Riolo et al., editors, Springer 2009, 16pp.
Hornby, G.S., "Steady-State ALPS for Real-Valued Problems," GECCO'09, Montreal, Jul. 2009, Assoc. for Computing Machinery, 8pp.
Idesign lab, "ALPS—the Age-Layered Population Structure,"UC Santa Cruz web article printed Mar. 17, 2011, 3 pp. (http://idesign.ucsc.edu/projects/alps.html).
Hodjat et al., "Chapter 5: Introducing an Age-Varying Fitness Estimation Function." Genetic Programming Theory and Practice X. Ed. Riolo et al., Springer Apr. 19, 2013, pp. 59-71.
Li, Xiaodong, and Michael Kirley. "The effects of varying population density in a fine-grained parallel genetic algorithm." Evolutionary Computation, 2002. CEC'02. Proceedings of the 2002 Congress on. vol. 2. IEEE, 2002.
Fidelis, Marcos Vinicius, Heitor S. Lopes, and Alex A. Freitas. "Discovering comprehensible classification rules with a genetic algorithm." Evolutionary Computation, 2000 Proceedings of the 2000 Congress on. vol. 1. IEEE, 2000.
Dec. 23, 2008, International Search Report and Written Opinion for PCT/US2008/82876, 6 pp.
Nov. 26, 2012 Extended EP Search Report for EP 08847214, 9 pp.
Jun. 16, 2011 Written Opinion from Singapore Patent Office in related application SG 201003127-6, 9 pp.
Apr. 20, 2012 Exam Report for related application AU 2008323758, 2 pp.
Lehman, Joel, and Kenneth O. Stanley. "Exploting open-endedness to solve problems through the search for novelty." ALIFE. 2008. (Year: 2008).
Al-Haj Baddar, S.W., "Finding Better Sorting Networks," Dissertation to Kent State University for PhD, May 2009, 86 pages.
Cuccli, G., et al., "When Novelty is Not Enough," vol. 6624 in Lecture Notes in Computer Science, published in Applications of Evolutionary Computation, Springer-Verlag Berlin Heidelberg, Copyright 2011, pp. 234-243.
Gomes, J., et al., "Devising Effective Novelty Search Algorithms: A Comprehensive Empirical Study," Madrid, Spain, Copyright Jul. 11-15, 2015, ACM, 8 pages.
Gomes, J., et al., "Evolution of Swarm Robotics Systems with Novelty Search," published in Swarm Intelligence, vol. 7, Issue 2, ANTS Special Issue, Copyright Sep. 2013, pp. 115-144.

(56) References Cited

OTHER PUBLICATIONS

Gomes, J., et al., "Progressive Minimal Criteria Novelly Search," Lisboa, Portugal, cited in Advances in Artificial Intelligence, Springer-Verlag Berlin Heidelberg, Copyright 2012, pp. 281-290.
Gupta, D., et al., "An Overview of methods maintaining Diversity in Gerienc Algorithms," International Journal of Emerging Technology and Advanced Engineering, vol. 2, Issue 5, New Delhi, India, May 2012, pp. 56-60.
Hodjat, B., et al, "Maintenance of a Long Running Distributed Genetic Programming System for Solving Problems Requiring Big Data," Genetic Finance Chap 1, published in Genetic Programming Theory and Practice XI as Chapter 4, Copyright 2014, 20 pages.
Kipfer, P., et al., "Uberflow: A GPU-Based Particle Engine," Computer Graphics and Visualization, the Eurographics Association, Copyright 2004, 9 pp.
Krcah, P., et al., "Combination of Novelty Search and Fitness-Based Search Applied to Robot Body-Brain Co-volution," Charles University, Prague Czech Republic, in Proceedings of the 13th Czech-Japan Seminar on Data Analysis and Decision Making in Service Science, 2010, 6 pages.
Lehman, J., et al., "Abandoning Objectives: Evolution through the Search for Novelty Alone," Evolutionary Computation journal, MIT Press, Copyright 2011, pp. 189-223.
Lehman, J., et al., "Efficiently Evolving Programs through the Search for Novelty," Proceedings of the Genetic and Evolutionary Computation Conference, ACM New York NY, Copyright 2010, 8 pages.
Lehman, J., et al., "Evolving a Diversity of Creatures through Novelty Search and Local Competition," Proceedings of the Genetic and Evolutionary Computation Conference, ACM, Copyright 2011, 8 pages.
Lehman, J., et al., "Extinction Events Can Accelerate Evolution," PLoS One, journal.pone.0132886, Aug. 12, 2015, 16 pages.
Lehman, J., et al., "Overcoming Deception in Evolution of Cognitive Behaviors," University of Texas at Austin, ACM, Jul. 12-16, 2014, 8 pages.
Lehman, J., et al., "Revising the Evolutionary Computation Abstraction: Minimal Criteria Novelty Search," Proceedings of the Genetic and Evolutionary Computation Conference, ACM, Copyright 2010, 8 pages.
OReilly, U., et al., "EC-Star: A Massive-Scale, HUB and Spoke, Distributed Genetic Programming System," Evolutionary Design and Optimization Group, published in Genetic Programming and Theory X as Chapter 6, published in V as Chap 1, Springer New York, Copyright 2013, 14 pages.
Salge, C., et al., "Empowerment—An Introduction," published in Guided Self-Organization: Inception, Chap 4, University of Hertfordshire, Copyright 2014, pp. 67-114.
Secretan, J., et al., "Picbreeder: A Case Study in Collaborative Evolutionary Exploration of Design Space," Evolutionary Computation journal, MIT Press, Copyright 2011, 30 pages.
Shahrzad, H., et al., "Tackling the Boolean Multiplexer Function Using a Highly Distributed Genetic Programming System," published in Genetic Programming Theory and Practice XII, Springer International Publishing, Copyright 2015, pp. 157-179.
Valsalam, V.K., et al., "Using Symmetry and Evolutionary Search to Minimize Sorting Networks," Journal of Machine Learning Research 14, The University of Texas at Austin, Department of Computer Science, Copyright Sep. 2013, pp. 303-331.
Wissner-Gross, A.D., et al., "Causal Entropic Forces," Physical Review Letters, PRL 110.168702, American Physical Society, Apr. 19, 2013, 5 pages.
International Search Report and Written Opinion for PCT App. No. PCT/IB16/01060, dated Jan. 24, 2017.
Juan-Julian Merelo-Guervos, et al., "Pool-Based Distributed Evolutionary Algorithm Using an Object Database," C. Di Chio, et al. (Eds.), EvoApplications 2012, LNCS 7248, pp. 446-455, 2012.
Laumanns, Marco, et al., "A Unified Model for Multi-Objective Evolutionary Algorithms with Elitism," IEEE, pp. 46-53, 2000.

Cempel et al., "Multidimensional condition monitoring of machinesin non-stationary operation," Mechanical Systems and Signal Processing 21, No. 3 (2007), 11 pages.
Adami et al., "Evolutionary learning in the 2D artificial life system 'Avida'." in Artificial life IV, vol. 1194, Cambridge, MA: The MIT Press, 1994, 5 pages.
Mitchell et al., "Genetic algorithms and artificial life," Artificial life, 1(3),1994, 267-289.
Pontoppidan et al., "Non-stationary condition monitoring through event alignment," in Machine Learning for Signal Processing, Proceedings of the 2004 14th IEEE Signal Processing Society Workshop, IEEE, 2004, pp. 499-508.
Oduguwa et al., "Bi-level optimisation using genetic algorithm," in Artificial Intelligence Systems, ICAIS IEEE International Conference on, 2002, pp. 322-327.
Hickinbotham et al. "Embodied genomes and metaprogramming," Advances in artificial life, ECAL 2011, pp. 334-341.
Hickinbotham et al. "Diversity from a Monoculture-Effects of Mutation-on-Copy in a String-Based Artificial Chemistry," ALife, 2010, pp. 24-31.
Jing et al., "From ALife agents to a kingdom of N queens," in Jiming Liu and Ning Zhong (Eds.), Intelligent Agent Technology: Systems, Methodologies, and Tools, 1999, 13 pages.
Hodjat et al., "Introducing a dynamic problem solving scheme based on a learning algonthrn in artificial life environments," Neural Networks, 1994, IEEE International Conference on. vol. 4., pp. 2332-2338.
Von Neumann, John, and Arthur W. "Theory of self-reproducing automata." IEEE Transactions on Neural Networks 5.1 (1966): 64-87.
Spector, Lee "Autoconstructive evolution: Push, pushGP, and pushpop." Proceedings of the Genetic and Evolutionary Computation Conference (GECCO-2001). vol. 137146. 2001, 11 pages.
Ray, Thomas S., "An evolutionary approach to synthetic biology: Zen and the art of creating life," Artificial Life 1.1_2, 39 pp., 1993.
Ofria et al., "Design of evolvable computer languages," Evolutionary Computation, IEEE Transactions on 6.4 (Aug. 2002): 420.424.
Moore et al., "Development and evaluation of an open-ended computational evolution system for the genetic analysis of susceptibility to common human diseases," Evolutionary Computation, Machine Learning and Data Mining in Bioinformatics. Springer Berlin Heidelberg, 2008. 129-140.
Baugh et al., "Evolution of GP mapping in a von Neumann Self-reproducer within Tierra," Advances in Artificial Life, ECAL. vol. 12. 2013, pp. 210-217.
Wagner et al., "Perspective: complex adaptations and the evolution of evolvability," Evolution (1996): 967-976.
Agogino et al., "Unifying temporal and structural credit assignment problems," Proceedings of the Third International Joint Conference on Autonomous Agents and Multiagent Systems—vol. 2. IEEE Computer Society, 2004, 8 pages.
Xie et al., "Multiagent optimization system for solving the traveling salesman problem (TSP)," Systems, Man, and Cybernetics, Part B: Cybernetics, IEEE Transactions on 39.2 (2009): 489-502.
Cremer et al., "Growth dynamics and the evolution of cooperation in microbial populations," Scientific reports, 2:281 (2012), 6 pages.
Woese, "The universal ancestor," Proceedings of the National Academy of Sciences 95.12 (1998): 6854-6859.
Whitacre et al. "Evolutionary mechanics: new engineering principles for the emergence of flexibility in a dynamic and uncertain world," Natural computing 11.3 (2012): 21 pages.
Spector et al., "Emergence of collective behavior in evolving populations of flying agents," Genetic Programming and Evolvable Machines 6.1 (2005): 111-125.
Bedau et al., "A comparison of evolutionary activity in artificial evolving systems and in the biosphere," in Proceedings of the fourth European Conference on Artificial life, pp. 125-134. MIT Press/Bradford Books, 1997, 12 pages.
Hodjat et al., "The Self-organizing symbiotic agent," arXiv preprint cs/9812013 (1998), 12 pages.
Ackley et al., "Indefinitely Scalable Computing= Artificial Life Engineering," ALIFE 14: The Fourteenth Conference on the Synthesis and Simulation of Living Systems. vol. 14 (2014), 8 pages.

(56) References Cited

OTHER PUBLICATIONS

Casillas et al., "Fuzzy-XCS: A Michigan genetic fuzzy system," Fuzzy Systems, IEEE Transactions on 15:4 (2007), 536-550.
Hickinbotham et al., "Specification of the stringmol chemical programming language," version 0.2, Technical Report YCS-2010-458, Univ. of York, 2010, 48 pages.
Han, Jing, "Local and global evaluation functions for computational evolution." Complex Systems, vol. 15, No. 4 (2005), 41 pages.
Bedau et al., "Evolution of evolvability via adaptation of mutation rates," Biosystems 69.2 (2003): 31 pages.
Koza, "Genetic Programming: On the Programming of Computers by Means of Natural Selection", Dec. 1992, MIT Press, pp. 1-609.
Qiu, Xin, et al., "Enhancing Evolutionary Conversion Rate Optimization Via Multi-Armed Bandit Algorithms," arXiv: 1803.03737v3 [cs.NE], Nov. 16, 2018, 9 pp.
Risto Miikkulainen, et al., "Conversion Rate Optimization Through Evolutionary Computation," in Proceedings of the Genetic and Evolutionary Computation Conference (GECCO '17), ACM, New York, New York, USA, 1193-1199, 2017.
Risto Miikkulainen, et al., "Sentient Ascend: AI-Based Massively Multivariate Conversion Rate Optimization," in Proceedings of the Thirtieth Innovative Applications of Artificial Intelligence Conference, AAAI, 2018.
Shipra Agrawal and Navin Goyal, "Analysis of Thompson Sampling for the Multi-Armed Bandit Problem," COLT 2012—The $25^{th}$ Annual Conference on Algorithmic Learning Theory, Jun. 25-27, 2012, Ediburgh, Scotland, 39.1-39.26.
Emilie Kaufmann, et al., "Thompson Sampling: An Asymptotically Optimal Finite Time Analysis," in Proceedings of the $23^{rd}$ International Conference on Algorithmic Learning Theory (ALT '12), Springer-Verlag, Berlin, Heidelberg, 199-213, 2012.

\* cited by examiner

WEBINTERFACE LAYOUT OF A FUNNEL

Dimensions and Dimension Values

Trust logo: display
Trust logo: hide

Headline font: *Andromeda*
Headline font: Impact
Headline font: Cambria 20px
Headline font: American Typewriter
Headline font: COPPERPLATE Headline: Don't miss the live auction
Headline: Only a few minutes left! Live Auction
Headline: When it's gone, it's gone forever
Headline: Win Your Dream Car!
Headline: You Can Win Your Car!

Elements/Actions: 7/6
Total Values: 28
Combinations: 3,200

Webinterface Layout

FIG. 5

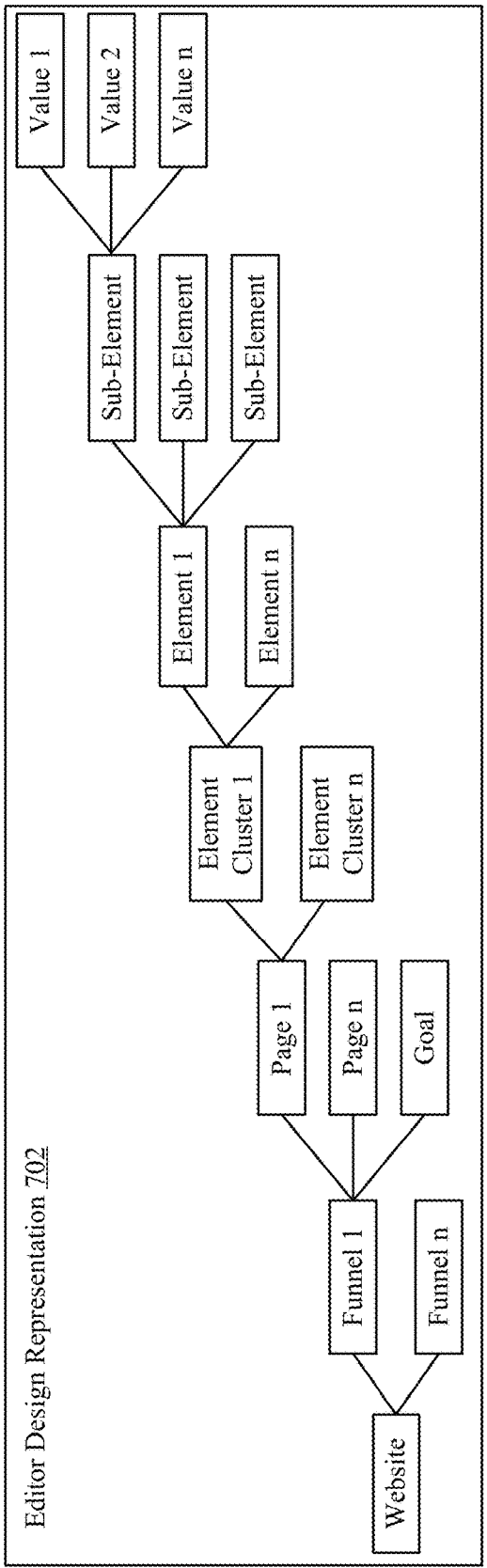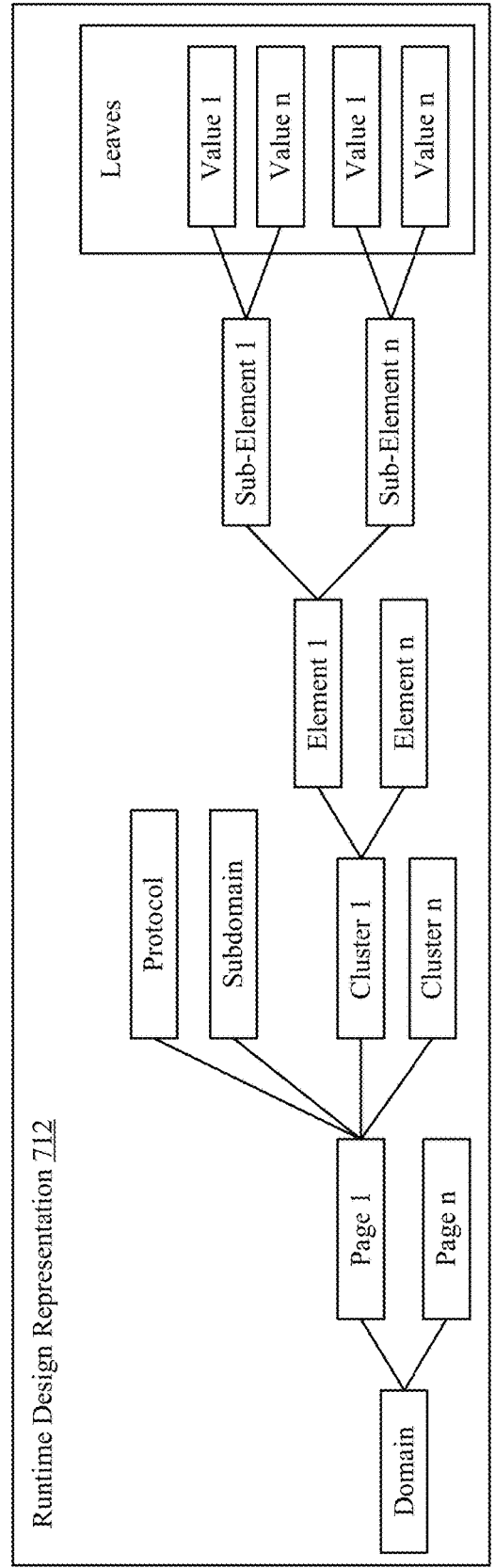
FIG. 7

CONTROL INDIVIDUAL & WINNING INDIVIDUAL
Control banner
Best performer
FIG. 17

METHOD AND SYSTEM FOR FINDING A SOLUTION TO A PROVIDED PROBLEM BY SELECTING A WINNER IN EVOLUTIONARY OPTIMIZATION OF A GENETIC ALGORITHM

CROSS REFERENCE TO OTHER APPLICATIONS

This application claims the benefit of U.S. Provisional Patent Application 62/466,227, "SELECTING A WINNER IN EVOLUTIONARY OPTIMIZATION", filed Mar. 2, 2017. The priority provisional application is hereby incorporated by reference.

This application incorporates by reference U.S. Non-provisional patent application Ser. No. 15/399,433, "MACHINE LEARNING BASED WEB INTERFACE GENERATION AND TESTING SYSTEM", filed on Jan. 5, 2017.

This application incorporates by reference U.S. Non-provisional patent application Ser. No. 15/399,520, entitled "WEB INTERFACE GENERATION AND TESTING USING ARTIFICIAL NEURAL NETWORKS", filed Jan. 5, 2017.

The application incorporates by reference U.S. Non-provisional patent application Ser. No. 14/494,346, entitled "VISUAL INTERACTIVE SEARCH,", filed on Sep. 23, 2014.

FIELD OF THE TECHNOLOGY DISCLOSED

The technology disclosed relates generally to genetic algorithm evolution, data mining and finding a solution to a provided problem by selecting a winning candidate using genetic algorithms, and in particular relates to web interface generation and testing using artificial intelligence by providing so-called machine learned conversion optimization (MLCO) solutions using evolutionary computations.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

A goal of evolving genetic algorithms and data mining is usually to solve some type of a problem. This can be accomplished by identifying a winner, i.e. the best candidate found during the evolution of many candidate solutions. The winner (i.e., the best candidate) is then employed in an application and good performance is expected to continue. For instance, when evolving web interfaces (e.g., webpages) that convert casual browsers (customers) to paying customers, the result is a web interface (webpage) that converts at an expected rate. However, the estimated or expected behavior of the webpages is often times based on a lucky response of a webpage.

For example, the performance of candidates can be measured during evolution of the genetic representation of a candidate through sampling. Sampling is performed by showing a candidate a relatively small number of examples, or subjecting the candidate to a small number of simulated situations, to see how well it performs. As a candidate, a web interface can be tested on a 1,000 users. The performance of the web interface converting the 1,000 users to paying customers is an average of these samples, i.e. a statistical estimate. This small sample size and/or small number of simulated situations can lead to inaccurate results.

Further, web interface optimization use A/B testing or multivariate analysis, where only a small number of candidate webpages are tested. A/B testing comprises designing two different versions of the same webpage (i.e., version A and version B), showing the different versions to different users, and collecting statistics on how well each version of the webpage was able to convert browsing customers to buying customers. This process allows incorporating human knowledge about the domain and conversion optimization into the design, and then testing the effect of the optimization. After observing the results, new designs can be compared and gradually improved. This A/B testing process is difficult and time-consuming and, as a result, only a very small fraction of webpage designs can be tested in this way. Therefore, subtle interactions in the design may be missed completely.

Multivariate analysis tests various combinations of a small number of variables. This approach relies on human intuition regarding which candidates of a genetic algorithm are worth testing, and therefore many good candidates (e.g., web interfaces) may never be found or implemented.

Further, common methods for running controlled experiments on websites include sophisticated conversion optimization solutions. Conversion optimization includes testing multiple combinations and variations of webpages and page elements at the same time. For example, two alternative images, plus two alternative headlines, plus two copy text alternatives, for a total of twenty-seven possible combinations (including the original control versions) may be provided. Thus, conversion optimization introduces a rather complex set of permutations and combinations that need to be analyzed to determine the most effective combination of page elements that truly engage the users.

These above-described shortcomings for webpage optimization become more prevalent as big data plays a more important role in web personalization. For example, the number of data signals, the complexity of rules and the sheer number of outcomes has increased exponentially, which amplifies these shortcomings. As that happens, human optimization simply cannot be done except perhaps after the fact, where there is little to no opportunity to impact the outcome. Algorithmic optimization is required. However, simple linear regression algorithms that can handle linear relationships and correlations may not be able to sufficiently create improved outcomes, given the vast number of data inputs and resulting measurements that have to be processed to predict performance.

Typically, to address these issues more user traffic is directed to the best candidates, with no guarantees or bounds, while knowing that resulting estimates are likely to be overestimates. This problem is a severe instance of the multiple hypothesis problem in statistics. The standard solution to this problem is to perform Bonferroni correction. Bonferroni correction essentially reduces the confidence by a factor of 1/N if N candidates are being tested. Given the large number of candidates, Bonferroni correction is not helpful in evolutionary optimization of genetic algorithms to identify one or more winning candidates. A better solution is described below.

SUMMARY OF THE INVENTION

The technology disclosed provides a so-called machine learned conversion optimization (MLCO) system that uses evolutionary computations to solve a provided problem by efficiently identifying most successful (i.e., a "winner") evolutions of genetic algorithms using a scoring system, such as fitness scores and neighborhood fitness scores. This will identify the best candidates for further evolution or implementation.

The technology discloses calculates an average fitness in a neighborhood of a candidate and then uses the neighborhood fitness instead of the candidate's own estimate fitness to select the winner and to report its performance.

For example, the MLCO system can use the evolutionary computations to efficiently identify most successful webpage designs in a search space without testing all possible webpage designs in the search space. The search space can be defined based on webpage designs provided by marketers. Website funnels (e.g., a single webpage or multiple webpages) are represented as genomes. Genomes identify different dimensions and dimension values of the funnels. The genomes are subjected to evolutionary operations like initialization, testing, competition, and procreation to identify parent genomes that perform well and offspring genomes (genetic algorithms) that are likely to perform well. Each webpage is tested only to the extent that it is possible to decide whether it is promising, i.e., whether it should serve as a parent for the next generation of genetic algorithms, or should be discarded.

According to an embodiment of the present technology, computer-implemented method for finding a solution to a provided problem by selecting a winning candidate individual is provided. The computer-implemented method includes storing, in a memory, a population of candidate individuals in a candidate pool, and evolving the candidate individuals in the candidate pool by performing evolution steps including: testing each candidate individual of the candidate individuals to obtain test results, assigning a performance measure to the tested candidate individuals in dependence upon the test results, discarding candidate individuals from the candidate pool in dependence upon their assigned performance measure, and adding, to the candidate pool, a new candidate individual procreated from candidate individuals remaining in the candidate pool after the discarding of the candidate individuals. The computer-implemented method further includes repeating the evolution steps to evolve the candidate individuals in the candidate pool, and selecting, as the winning candidate individual, a candidate individual from the candidate pool having a best neighborhood performance measure, where the neighborhood performance measure of a particular candidate individual is given by the performance measures of (i) the particular candidate individual and (ii) K neighborhood candidate individuals which are nearest in the candidate pool to the particular candidate individual according to a predefined definition of nearness, and where K>0, wherein the selected winning candidate individual is the solution to the provided problem.

According to another embodiment of the present technology, a non-transitory computer-readable recording medium having instructions recorded thereon for finding a solution to a provided problem by selecting a winning candidate individual is provided. The instructions, when executed by a processor of a computer, cause the computer to execute a method. The method includes storing, in a memory, a population of candidate individuals in a candidate pool, and evolving the candidate individuals in the candidate pool by performing evolution steps including: testing each candidate individual of the candidate individuals to obtain test results, assigning a performance measure to the tested candidate individuals in dependence upon the test results, discarding candidate individuals from the candidate pool in dependence upon their assigned performance measure, and adding, to the candidate pool, a new candidate individual procreated from candidate individuals remaining in the candidate pool after the discarding of the candidate individuals. The computer-implemented method further includes repeating the evolution steps to evolve the candidate individuals in the candidate pool, and selecting, as the winning candidate individual, a candidate individual from the candidate pool having a best neighborhood performance measure, where the neighborhood performance measure of a particular candidate individual is given by the performance measures of (i) the particular candidate individual and (ii) K neighborhood candidate individuals which are nearest in the candidate pool to the particular candidate individual according to a predefined definition of nearness, and where K>0, wherein the selected winning candidate individual is the solution to the provided problem.

In a further embodiment of the present technology, a computer-implemented system for finding a solution to a provided problem by selecting a winning candidate individual is provided. The computer-implemented system includes a memory storing a population of candidate individuals in a candidate pool and a conversion system evolving the candidate individuals in the candidate pool by performing evolution steps including: testing each candidate individual of the candidate individuals to obtain test results, assigning a performance measure to the tested candidate individuals in dependence upon the test results, discarding candidate individuals from the candidate pool in dependence upon their assigned performance measure, and adding, to the candidate pool, a new candidate individual procreated from candidate individuals remaining in the candidate pool after the discarding of the candidate individuals. The conversion system also repeats the evolution steps to evolve the candidate individuals in the candidate pool. The computer-implemented system further includes a winner selector selecting, as the winning candidate individual, a candidate individual from the candidate pool having a best neighborhood performance measure, where the neighborhood performance measure of a particular candidate individual is given the performance measures of (i) the particular candidate individual and (ii) K neighborhood candidate individuals which are nearest in the candidate pool to the particular candidate individual according to a predefined definition of nearness, and where K>0, wherein the selected winning candidate individual is the solution to the provided problem.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 5 depicts a web interface layout of a funnel.

FIG. 7 is a symbolic drawing of one implementation of transforming an editor design representation of a starter funnel into a runtime design representation.

FIG. 17 graphically illustrates a control individual and a winning individual, and comprising dimensions and dimension values.

DETAILED DESCRIPTION

Introduction

Figure 1:
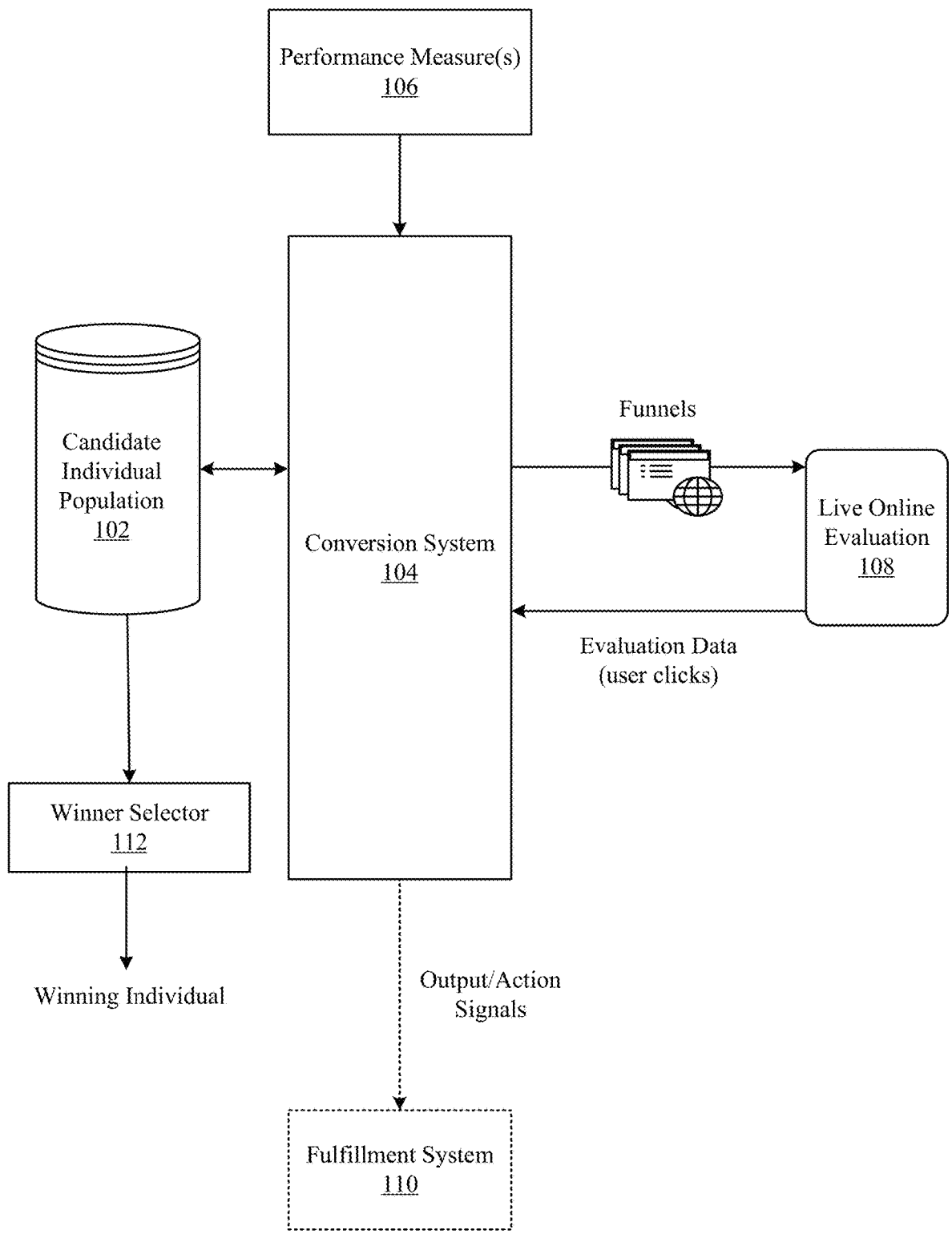
FIG. 1 depicts a conversion system that implements evolutionary computations to identify high performing candidate individuals in a candidate search space.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Examples of systems, apparatus, and methods according to the disclosed implementations are described in a conversion optimization context. In other instances, the technology disclosed can be applied to multivariate testing, A/B testing, landing page optimization, conversion rate optimization, website testing, website optimization, search engine optimization, information technology, telecommunications systems, financial systems, security trading, banking, business intelligence, marketing, medical and health sciences, mining, energy, etc. Other services are possible, such that the following examples should not be taken as definitive or limiting either in scope, context, or setting.

The technology disclosed can be implemented in the context of any computer-implemented system including a database system, a multi-tenant environment, or a relational database implementation like an Oracle™ compatible database implementation, an IBM DB2 Enterprise Server™ compatible relational database implementation, a MySQL™ or PostgreSQL™ compatible relational database implementation or a Microsoft SQL Server™ compatible relational database implementation or a NoSQL™ non-relational database implementation such as a Vampire™ compatible non-relational database implementation, an Apache Cassandra™ compatible non-relational database implementation, a BigTable™ compatible non-relational database implementation or an HBase™ or DynamoDB™ compatible non-relational database implementation. In addition, the technology disclosed can be implemented using different programming models like MapReduce™, bulk synchronous programming, MPI primitives, etc. or different scalable batch and stream management systems like Amazon Web Services (AWS)™, including Amazon Elasticsearch Service™ and Amazon Kinesis™, Apache Storm™, Apache Spark™, Apache Kafka™, Apache Flink™, Truviso™, IBM Info-Sphere™, Borealis™ and Yahoo! S4™.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "specify" is used herein to mean the same as "identify".

As used herein, a given signal, event or value is "in dependence upon" a predecessor signal, event or value of the predecessor signal, event or value influenced by the given signal, event or value. If there is an intervening processing element, step or time period, the given signal, event or value can still be "in dependence upon" the predecessor signal, event or value. If the intervening processing element or step combines more than one signal, event or value, the signal output of the processing element or step is considered "in dependence upon" each of the signal, event or value inputs. If the given signal, event or value is the same as the predecessor signal, event or value, this is merely a degenerate case in which the given signal, event or value is still considered to be "in dependence upon" or "dependent on" or "based on" the predecessor signal, event or value. "Responsiveness" of a given signal, event or value upon another signal, event or value is defined similarly.

As used herein, "concurrently" or "in parallel" does not require exact simultaneity. It is sufficient if the evaluation of one of the individuals begins before the evaluation of another of the individuals completes.

As used herein, the term "funnel" refers to a frontend of a candidate individual, which is perceivable, operable, and understandable by end users. In implementations, a funnel invites user interaction and responds to it. A funnel comprises one or more web interfaces. Some examples of web interfaces include, both control versions and variations of, webpages, websites, e-mails, mobile applications, desktop applications, digital advertisements, social media messages (e.g., Tweet™, Facebook Post™), social media feed items, social media profiles, social media accounts, social media chat messages, generic chat messages, forms, auto-filled forms, and so on. In some implementations a funnel can include branching.

In implementations of the technology disclosed, a funnel is implemented in or across one or more Internet accessible data centers such as a website (a set of funnels), together with associated applications running behind the website. End users operate Internet-accessible client devices or clients (e.g., desktop computers, notebook computers, tablets, mobile devices, phones or other devices having rendering engines, or the like) that are capable of accessing and interacting with the funnel. In one implementation, the end users access the funnel by opening a web browser or a mobile application. In some implementations, the end users may authenticate to the funnel (or some portion thereof).

In implementations of the technology disclosed, a web interface is a structured document whose structure is dependent upon the underlying format. For example, in one implementation, a web interface has a web-supported format based on Hyper Text Markup Language (HTML), Extensible Markup Language (XML), or other web-supported structured document. The web interface may include one or more resources (e.g., a JavaScript resource, a Cascading Style Sheet (CSS) resource, an Asynchronous and JavaScript XML (AJAX) resource, an image resource, a video resource, etc.), or, more typically, references to such resources, embedded within the web interface. By way of example, a resource embedded in the web interface may generally be included or specified within a script element, style element, image element, or object element, among others, depending on the type of resource. Typically, a web browser or other client application executing at the client device of the end user constructs a document object model (DOM) representation of the received web interface.

In another implementation, the web interface has an e-mail format based on plain text, rich text, or HTML (with or without a style definition format such as CSS or scripting instructions in a format such as JavaScript, e.g., Microsoft Outlook™, Google Gmail™, Apple Mail™, iOS Mail™, Thunderbird™, AOL Mail™, Yahoo Mail™, Windows Live™). In yet other implementations, the web interface has a mobile application format based on HTML5, native formats (e.g., iOS™ or Android™), and hybrid formats.

Any other conventional or future-developed structured documents or formats thereof or used therein, are considered to be web interfaces. Such implementations will be readily apparent to those skilled in the art without departing from the spirit and scope of the technology disclosed (such as audio and haptic presentations of web interfaces).

The web interface (e.g., webpages, websites, e-mails, mobile applications, desktop applications, digital advertisements) comprises page elements. Some examples of page elements include images, videos, animations, headline, heading, calls-to-action, text copies, form length, and others. In one example, the calls-to-action define what happens when a user clicks or taps on any part of the web interface. The page elements of the web interface are arranged in a so-called web interface layout. A web interface layout defines the positioning of the page elements of the web interface relative to each other. For example, an image might be at the bottom right and a video in the center of the web interface layout. In the web interface, all the interchangeable page elements are described using the web interface layout, which describes how the page elements are supposed to appear relative to each other and how they are supposed to interact with each other. Each page element has several properties. For example, image page elements have properties related to type, placement, and size; calls-to-action have properties related to color, text, size, and placement; and text copies have properties related to content, length, and size.

As used herein, the terms "funnel(s)", "candidate individual(s)", "individual(s)", "genome(s)", and "chromosome(s)" are used interchangeably. Also, "individual(s)", "genome(s)", and "chromosome(s)" are composed of gene(s) and/or "gene value(s)". As used herein, the term "gene(s)" and/or "gene value(s)" can refer to a different "entity" and/or different "entities" such as cluster(s) or page element(s) or element(s) or dimension(s) or starter dimension(s), page element value(s) or element value(s) or dimension value(s) or start dimension value(s) or value(s), sub-sequence(s), sub-element(s) or control sub-element(s) or test sub-element(s), sub-element value(s) or control sub-element value(s) or test sub-element values, or any combinations thereof. Accordingly, as used herein, "gene-by-gene" operations or operations conducted or carried out at the "gene-level", such as gene-by-gene selection, gene-by-gene crossover, or gene-by-gene mutation can treat a single entity as a single unit to select, to crossover, and/or to mutate and/or or a combination of entities as a single unit to select, to crossover, and/or to mutate.

Machine Learned Conversion Optimization

The technology disclosed provides a so-called machine learned conversion optimization (MLCO) system that uses evolutionary computations to efficiently identify most successful webpage designs in a search space without testing all possible webpage designs in the search space. The search space is defined based on webpage designs provided by marketers. Website funnels with a single webpage or multiple webpages are represented as genomes. Genomes identify different dimensions and dimension values of the funnels. The genomes are subjected to evolutionary operations like initialization, testing, competition, and procreation to identify parent genomes that perform well and offspring genomes (genetic material) that are likely to perform well. Each webpage (e.g., genetic material) is tested only to the extent that it is possible to decide whether it is promising, i.e., whether it should serve as a parent for the next generation of genetic materials, or should be discarded.

In addition to webpages, genetic algorithms can be applied to many other types of environments. For example, genetic algorithms can be used in any environment in which a large amount of data can be or has been collected which records experience over time within the environment. Specifically, for example, a healthcare environment may record clinical data, diagnoses and treatment regimens for a large number of patients, as well as outcomes. A business environment may record customer information such as who they are and what they do, and their browsing and purchasing histories. A computer security environment may record a large number of software code examples that have been found to be malicious. A financial asset trading environment may record historical price trends and related statistics about numerous financial assets (e.g., securities, indices, currencies) over a long period of time. Genetic algorithms have been applied to all of the above-mentioned environments. With respect to stock categorization, for example, according to one theory, at any given time, 5% of stocks follow a trend. Genetic algorithms are thus sometimes used, with some success, to categorize a stock as following or not following a trend.

In ecommerce, designing user experiences, i.e., webpages and interactions, which convert as many end users as possible from casual browsers to paying customers is an important goal. While there are some well-known design principles, including simplicity and consistency, there are also often unexpected interactions between elements of the page that determine how well it converts. The same element may work well in one context but not in others—it is often hard to predict the result, and even harder to decide how to improve a given page.

An entire industry has emerged to tackle these challenges; it is called conversion rate optimization, or conversion science. The standard method most practitioners use is AB testing, i.e., designing two different version of the same page, showing them to different users, and collecting statistics on how well they each convert. This process allows incorporating human knowledge about the domain and conversion optimization into the design, and then testing their effect. After observing the results, new designs can be compared and gradually improved. The A/B testing process is difficult and time-consuming. Only a very small fraction of page designs can be tested in this way, and subtle interactions in the design may simply be missed completely.

The technology disclosed automatically generates webpage candidates to be tested from the variables and variable values marketers themselves create. The variables and variable values can be anything on a website, from small changes like button color and font weight to whole-scale messaging and design specifications. These variables can all be on a single page or across multiple pages in a funnel. The technology disclosed searches for the most successful variables and variable values in a vast space of possible combinations of the values.

With the technology disclosed, thousands of page designs can be tested in a short time, which is impossible through A/B testing. On the other hand, through evolutionary search, the technology disclosed tests only a small subset (e.g., thousands) of page designs out of a much larger set of page designs (e.g., millions) to find the best ones. The technology disclosed learns over time which combinations of elements are effective, and gradually focuses the search around the most promising designs.

The technology disclosed is an automated system for conversion optimization, capable of testing vastly more ideas in shortened time frames. It finds the subtle combinations of variables that lead to conversion increases. The technology disclosed can discover designs that convert better than those designed by humans, often because it finds unexpected interactions between elements. For instance, the technology disclosed can find that the button needs to be green, but only when it is transparent and the header is in small font and the header text is aligned. Such interactions often do exist, and they can be very difficult to find. The technology disclosed makes this discovery process automatic, based on artificial intelligence, instead of extensive human effort. With the technology disclosed, it is thus possible to optimize conversions better and at a much larger scale than before—and keep optimizing them as the e-commerce conditions change.

Using Neighborhood Fitness

Evolutionary optimization is a parallel search method that gradually improves the quality of a population of candidates. The quality of a candidate is measured by a fitness function. At the end of the evolution, the candidate with the highest fitness is selected as a winner. Thus, the final result of the evolutionary run is to identify the candidate that is supposed to be the best in the population of candidates. In practice in many domains, however, the fitness can only be measured approximately, by testing each candidate with a number of samples. For instance, with respect to web interface design, each candidate is a web interface design that is shown to a number of users (such as 1,000) to estimate how well the web interface design converts browsing customers to purchasing customers. Such sampling results in a multiple hypothesis problem. Because several thousands of candidates are tested in this way, some of them will have high estimated conversion rates simply because they were lucky, i.e. by chance happened to receive many users that converted. If such a lucky candidate is selected as a winner, it will disappoint in the future because true conversion rate (that will be observed in the long run in the future) will be much lower. In some embodiments, all of the fitness estimates will be uncertain, unreliable, and/or stochastic.

In evolutionary computation, a set of new samples, called a validation set, is given to the top candidates, and the candidate that performs best on the validation set is selected. It is not known how many samples are needed to do this reliably and the multiple hypothesis problem still exists. This approach also requires more samples than can be used during evolution, and they need to be available after evolution, which is not always the case (e.g. in web interface design, no more users are available after the experiment is terminated).

The technique disclosed herein is based on the idea that the fitness space is smooth, such that similar genomes have similar fitness. This is a fundamental assumption in evolutionary computation in general, meaning that in searching for solutions, parts of existing genomes are combined, and they are mutated slightly, to find even better ones. With this assumption, it is possible to obtain a more reliable estimate of a candidate's true fitness by averaging the fitness of each of its neighbors. Fitness will be overestimated for some candidate and under estimated in other candidates in the neighborhood. However, an average fitness across neighbors should be close to the true fitness. Neighborhood fitness is thus used to identify the best candidate because the average across neighbors is a better estimate of a candidate's future performance. Further, the probabilities (p-values) that a candidate is better than others can be calculated based on a permutation test, and significance can be compared to a particular control by comparing two binomial distributions. Specific implementations and detailed descriptions of using neighborhood fitness methods are described below in more detail.

Machine Learned Conversion Optimization (MLCO) System

FIG. 1 depicts a conversion system 104 that implements evolutionary computations to identify high performing candidate individuals in a candidate search space. The conversion system 104 does so by perpetually collecting and developing performance measures 106 for candidate individuals in the candidate individual population 102. The conversion system 104 also uses a presentation generator to transform the candidate individuals into funnels of one or more web interfaces. The funnels are presented to end users during live online evaluation 108 so that the performance measures 106 can be developed for the corresponding candidate individuals based on evaluation data (e.g., user clicks) provided by the end users.

Each funnel has a mechanism by which achievement of a target user behavior can be detected. In one implementation, the target user behavior is conversion by end users. For each funnel, conversion can be detected based on a conversion goal defined by a designer, marketer, advertiser, or content creator. Examples of a conversion goal include a user reaching a specific web interface of a funnel (e.g., a thank you page), a user clicking a link or button or other user interface element on a web interface of a funnel, or any other custom event defined by the designer (e.g., using jQuery). Other examples of a conversion goal include a user clicking a "Buy Now" button on Amazon.com™, a user clicking a "Sign Up" button on an e-mail registration page, a user clicking a "Download Now" button on an application landing page, a user filling out a form to download a report, a user signing up for a webinar, a user completing a purchase process, a user adding an item to a shopping cart, a user initializing a shopping cart checkout, and a user making a pledge to read a book. The conversion goals can be different for different funnels and different testing environments.

The conversion system 104 operates according to the performance measures 106, which indicate to the conversion system 104 how to measure the fitness of a candidate individual. The conversion system 104 optimizes for candidate individuals that have the greatest fitness, however fitness is defined by the performance measures 106. The performance measures 106 are an indication of success of a candidate individual and corresponding funnel in achieving a target user behavior. The performance measures 106 are specific to the environment and goals of the particular application. In a webpage testing environment, for example, the performance measures 106 can be a function of a conversion goal defined for a funnel. In one implementation, the performance measures 106 are based on a "conversion rate". Conversion rate is a ratio of end users who visit a funnel and complete the conversion goal defined for the funnel (i.e., what percentage of the visitors complete the conversion goal). For example, a website with 5,000 visitors and 50 conversions has a conversion rate of 1%. In another implementation, the performance measures 106 are based on a "revenue rate". Revenue rate is a revenue amount (e.g., numerical dollar value) generated per end user as a result of the end users completing the conversion goal defined for the funnel.

Regarding the live online evaluation 108, "live online evaluation" means real time tests or trials where funnels constructed in dependence upon the candidate individuals are presented to real world end users for testing. During the live online evaluation 108, the performance measures 106 are developed for each of the candidate individuals based on the real time and real world user interaction with the corresponding funnels. Typically, for each funnel, the performance measures 106 are determined over a sample of end users (e.g., 1000 end users or 2000 end users, and so on). Note that the performance measures 106 calculated based on the performance of the funnels during the live online evaluation 108 are associated with or linked to or assigned to the corresponding candidate individuals originally used to generate the funnels. After that, the performance measures 106 are used by the disclosed evolutionary computations to procreate high performing individuals.

The conversion system 104 interacts with a database containing the candidate individual population 102. As used herein, the term "database" does not necessarily imply any unity of structure. For example, two or more separate databases, when considered together, still constitute a "database" as that term is used herein. In some implementations, the database can store information from one or more tenants into tables of a common database image to form an on-demand database service (ODDS), which can be implemented in many ways, such as a multi-tenant database system (MTDS). A database image can include one or more database objects. In other implementations, the database can be a relational database management system (RDBMS), object oriented database management system (OODBMS), distributed file system (DFS), no-schema database, or any other data storing system or computing device.

In one implementation, the candidate individuals in the candidate individual population 102 are stored and managed by conventional database management systems (DBMS), and are accessed using SQL statements. Thus, a conventional SQL query can be used to obtain, for example, the performance measures 106 of the candidate individuals. New candidate individuals can be inserted into the candidate individual population 102 using the SQL "insert" statement, and candidate individuals being discarded can be deleted using the SQL "delete" statement. In another implementation, the candidate individuals in the candidate individual population 102 are stored in a linked list. In such an implementation, insertion of a new candidate individual can be accomplished by writing its contents into an element in a free list, and then linking the element into the main linked list. Discarding of candidate individuals involves unlinking them from the main linked list and re-linking them into the free list.

In an implementation a winner selector 112 selects a winning candidate or multiple winning candidates from the candidate individual population 102 when evolution is complete. Evolution can be complete (i) after a set number of evolutions of the candidates have been performed, (ii) at a point when a predetermined conversion rate is reached, or (iii) at any other time that is convenient. When evolution of the candidates is complete, there should be multiple candidates in the candidate individual population 102. The winning candidate or candidates are selected by the winner selector 112 (from the candidate individual population 102) based on a neighborhood average fitness (e.g., based on a best neighborhood performance measure). The winning candidate or candidates can represent a particular solution to a problem, such as identifying a webpage that would likely result in the highest conversion rate or revenue. The determination of the neighborhood average fitness is discussed in more detail below.

In some implementations, the MLCO system uses an optional fulfillment system 110. Fulfillment system 110 is a system that is controlled automatically by output/action signals from the conversion system 104. In a webpage testing environment, for example, the fulfillment system 110 is a product distribution e-warehouse (e.g., Amazon.com™) that receives the signals via a computer network (not shown) and takes appropriate transactional and delivery actions.

The discussion now turns to the evolutionary computations implemented by the MLCO system of FIG. 1.

Evolutionary Computations

Figure 2:
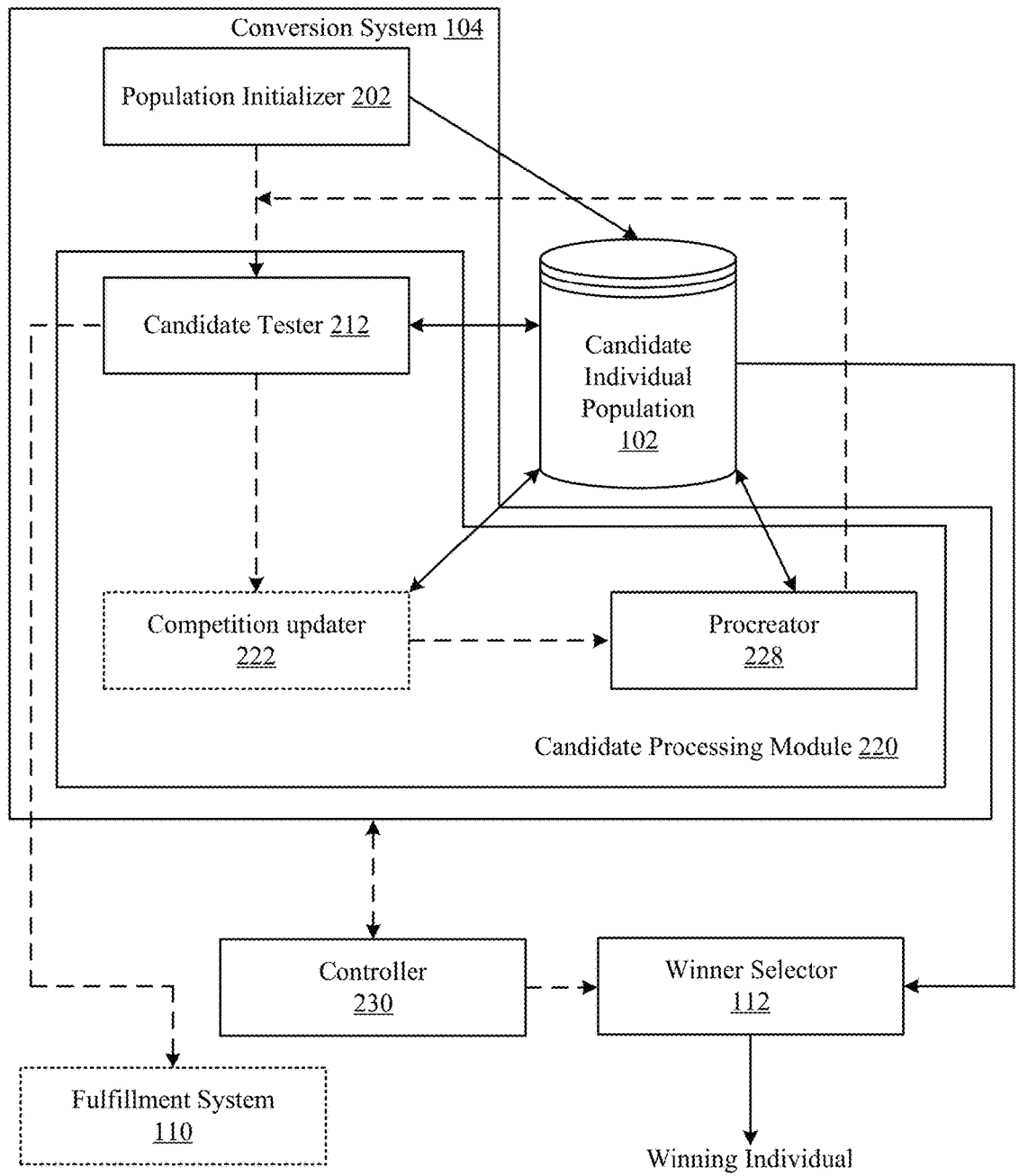
FIG. 2 illustrates modules that can be used to implement the evolutionary computations of the conversion system in FIG. 1.

FIG. 2 illustrates elements that can be used to implement the evolutionary computations of the conversion system 104 in FIG. 1. In FIG. 2, solid lines indicate data flow, broken lines indicate control flow, and dotted lines indicate optional modules. The elements in FIG. 2 can be implemented in hardware or software, and need not be divided up in precisely the same blocks as shown in FIG. 2. Some of the elements can also be implemented on different processors or computers, or spread among a number of different processors or computers. In addition, it will be appreciated that some of the elements can be combined, operated in parallel or in a different sequence than that shown in FIG. 2 without affecting the functions achieved. The blocks in FIG. 2, designated as elements, can also be thought of as flowchart steps in a method. An element also need not necessarily have all its code disposed contiguously in memory; some parts of the code can be separated from other parts of the code with code from other elements or other functions disposed in between.

Population Initialization

Referring to FIG. 2, the candidate individual population 102 is initialized by a population initializer 202, which writes a preliminary pool of candidate individuals in the candidate individual population 102. The preliminary pool can be created randomly, or in some implementations, a priori knowledge can be used to seed the first generation. In another implementation, candidate individuals from prior runs can be borrowed to seed a new run. At the start, all candidate individuals are initialized with performance measures 106 that are indicated as undefined.

The population initializer 202 also defines a candidate search space. As used herein, the term "candidate search space" refers to a space having M dimensions, where each dimension represents an axis along which different candidate individuals can have different values. The size of the space in each dimension is equal to the range of values available for that dimension.

The following discussion describes how a starter funnel is defined by a designer, marketer, advertiser, or content creator using a design editor. Once defined, the starter funnel is used by the population initializer 202 to define the candidate search space and seed the first generation.

Starter Funnel Definition

Figure 3:
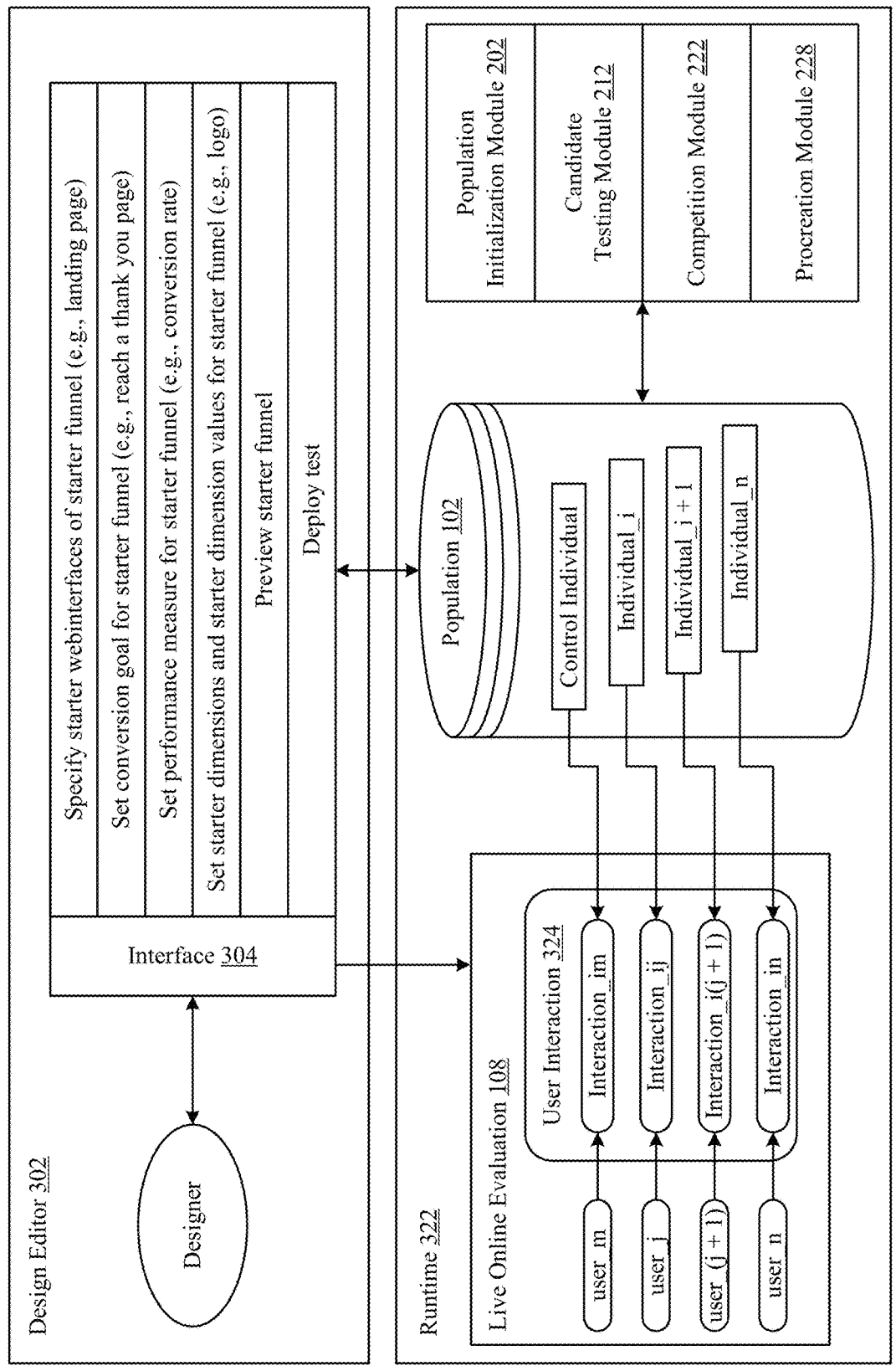
FIG. 3 shows a workflow of the disclosed machine learned conversion optimization (MLCO).

The candidate search space is defined by the population initializer 202 in dependence upon at least one starter funnel, and the starter dimensions and starter dimension values of its starter web interfaces. In implementations, the starter funnel is defined using a design editor 302, shown in FIG. 3. Design editor 302 comprises various interface components as part of interface 304 that are used by a designer, marketer, advertiser, or content creator to implement a MLCO workflow. In particular, the design editor 302 is used by the designer to: specify one or more starter web interfaces of the starter funnel; set a conversion goal for the starter funnel; set a performance metric for the starter funnel; set starter dimensions and starter dimension values for each of the starter web interfaces of the starter funnel; preview the starter funnel; and deploy the test.

Figure 4:
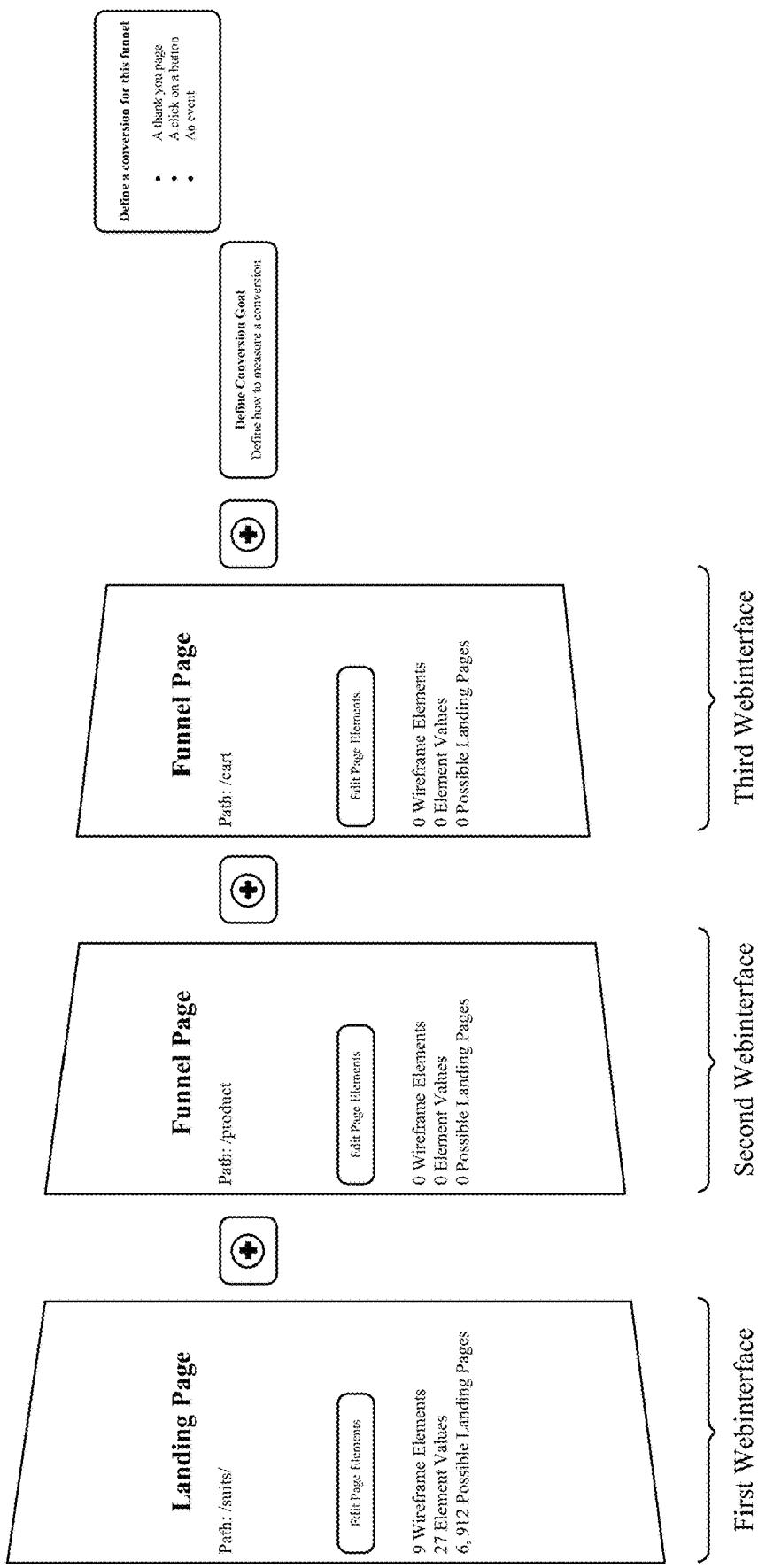
FIG. 4 illustrates a funnel with multiple web interfaces.

FIG. 4 shows one implementation of a starter funnel with three starter web interfaces (e.g., one landing page and two funnel pages). In one implementation, the starter web interfaces are identified in the starter funnel by their respective access paths (e.g., unified resource locators (URLs), and arranged in a topological sequence. Typically, the topological sequence determines a path an end user follows through a funnel to complete a conversion goal defined for the funnel. The topological sequence is set graphically by the designer across the interface 304 and stored logically in memory.

FIG. 4 also depicts a "define conversion goal" button that allows the designer to set a conversion goal for the starter funnel. Examples of a conversion goal also include "increase leads" or "increase revenue". The designer also defines what type of events will be considered to indicate that a conversion has occurred, such as visiting a thank you page, clicking on a button or link, or a custom event. After setting the conversion goal, the designer specifies a performance metric for the starter funnel. The performance metric is used by the disclosed evolutionary computations to evaluate the performance of the candidate individuals during the test.

Then, a web interface layout is generated for the starter funnel. As used herein, a "web interface layout" is merely a template within which the alternative values for dimensions are inserted in order to define a particular web interface of a funnel. In one implementation, the web interface layout is displayed across a simulated device selected by the designer from among options of devices with varying screen canvases (e.g., smartphones, tablets, computers, wearable devices). In some implementations, the options of devices lists different device models like iPhone X™, Samsung Galaxy S8™, and others. FIG. 5 illustrates one implementation of a web interface layout and different dimensions and dimension values that can be applied to the web interface layout.

Then, the designer selects different page elements (referred to herein as "starter dimensions") to be included in the web interface layout for each of the starter web interfaces of the starter funnel. In one implementation, the designer also specifies a type for a page element. For example, a name of the page element is "Clean, Awesome and Multi-Purpose" and the type of the page element is "Headline—Main". Advancing further, the designer defines different sub-elements (also referred to herein as "starter dimensions") for each of the starter web interfaces of the starter funnel. Examples of sub-elements include text, formatting/CSS (Cascading Style Sheets), page element concealment, page element removal, class, HTML, custom jQuery, and image. In some implementations, the designer can activate or deactivate some of the sub-elements (e.g., using a dropdown). In one implementation, the inactive sub-elements are displayed across the interface 304 with strikethrough. In other implementations, the design editor 302 automatically makes some sub-elements active and others inactive.

Then, the designer sets sub-elements values (referred to herein as "starter dimension values") for each of the defined sub-elements. In addition, the designer also sets, for each of the defined sub-elements, a control sub-element value and one or more test sub-element values. In other implementations, the design editor 302 automatically sets a default control value for the sub-elements. For example, for the page element "Headline—Main", the control sub-element value is set to be "Clean, Awesome and Multi-Purpose" and test sub-element values are set to be "Slick, Awesome and Powerful", "New, Fast, Better", "Shiny, Better than the Competition", and "Best you can Buy". Similarly, in other implementations, different page elements and corresponding sub-elements and sub-element values can be defined as a set of starter dimensions and starter dimension values of each of the starter web interfaces of the starter funnel.

Each web interface of a funnel can be thought of as a point in a vector-based search space. Each dimension axis in the vector space corresponds to one of the page elements, and each different coordinate position along a given axis indicates one of the designer-specified alternatives for that page element. For example, in FIG. 5, the call-to-action dimension has four coordinate positions (values or alternatives), namely "Go!", "Go to the Auction!", "Win the Auction!", and "Win it NOW!". A particular web interface of a funnel specifies a value for each of the page elements/dimensions.

Figure 6:
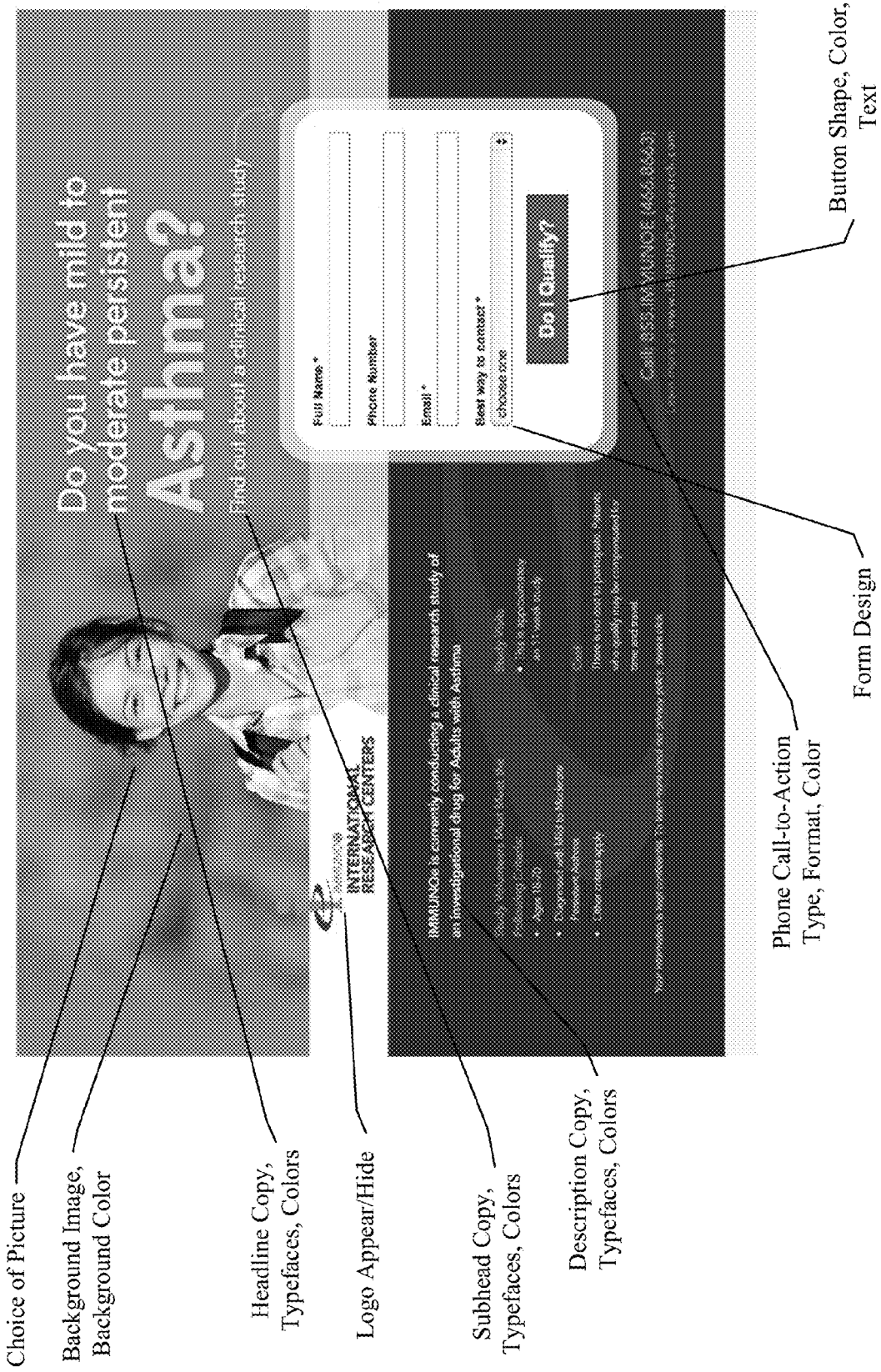
FIG. 6 shows a web interface of a funnel with its dimensions and dimension values.

FIG. 6 shows one implementation of a web interface of a funnel. In FIG. 6, the web interface is defined by the arrangement or position of different page elements/dimensions in the web interface layout, and corresponding properties or values of the page elements/dimensions, including, choice of picture (page element/dimension), background image (page element/dimension), background color (page element property/dimension value), headline copy (page element/dimension), typefaces and colors of the headline copy (page element property/dimension value), appearance or concealment of logo (page element/dimension), subhead copy (page element/dimension), typefaces and colors of the subhead copy (page element property/dimension value), description copy (page element/dimension), typefaces and colors of the description copy (page element property/dimension value), phone call-to-action (page element/dimension), type, format, and color of the phone call-to-action (page element property/dimension value), form design (page element/dimension), button (page element/dimension), and shape, color, and text of the button (page element property/dimension value).

Once created, a preview of the starter funnel, and its comprising starter web interfaces, is presented to the designer across the interface 304.

With the definition of the starter funnel understood, the discussion now turns to how a corresponding starter candidate individual is initialized by encoding the starter funnel at runtime.

Starter Individual Initialization

FIG. 7 is a symbolic drawing of one implementation of transforming an editor design representation 702 of a starter funnel into a runtime design representation 712. At runtime 322, the editor design representation 702 of the starter funnel defined by the designer is transformed into the runtime design representation 712. In the example used in FIG. 7, the editor design representation 702 includes a tree. The root of the tree is the highest level of granularity for which a test is performed. For a website or mobile webpage, the root is the domain. For mobile applications, the root is the application. For e-mails, the root is the e-mail; the subject and pages are next level of the tree. For other applications (such as advertising), different mappings can be used. In the domain of webpages and mobile applications, a website has one to n funnels; each funnel has a goal, and one to n pages. Each page has one to n clusters of elements. Each cluster has one to n elements. Each element has a set of sub-elements that change a property of the element. As used herein, sub-elements are elements too. Each sub-element has one to n values. In other implementations, the structure might be different. For example, elements might not be clustered, or the representation might not be hierarchical at all.

Also at the runtime 322, the starter funnel is represented by a starter genome that encodes it as a binary formulation. In one implementation, the binary encoding is a concatenation of the leaves of the tree, which in the case of the starter funnel includes concatenating the starter dimensions and starter dimension values of each of the starter web interfaces of the starter funnel. In some implementations, prior to the genome encoding, a schematic representation of the editor designer representation 702 is generated in the form of runtime design representation 712. In other implementations, the genome encoding can be based on other schemes relying on data types other than binary data type (0 or 1), such as quantitative or numerical data type, qualitative data type, discreet data type, continuous data type (with lower and upper bounds), integers data type (with lower and upper bounds), nominal data type, ordinal or ranked data type, categorical data type, interval data type, and/or ratio data type. For example, the genome encoding can be based on, or any combination thereof, real values between 0 and 1, continuous values such as Red, Green, Blue (RGB) values between 0 and 256, hexadecimal values of CSS colors (e.g., #F0F8FF), categorical color values of CSS colors (e.g., AliceBlue), respective values of other CSS property groups and properties, size of a particular dimension (e.g., height and width), a set of different values and data types (e.g., different numeric dollar price values or a combination of different numeric dollar price values and heights and widths), and others.

Figure 8:
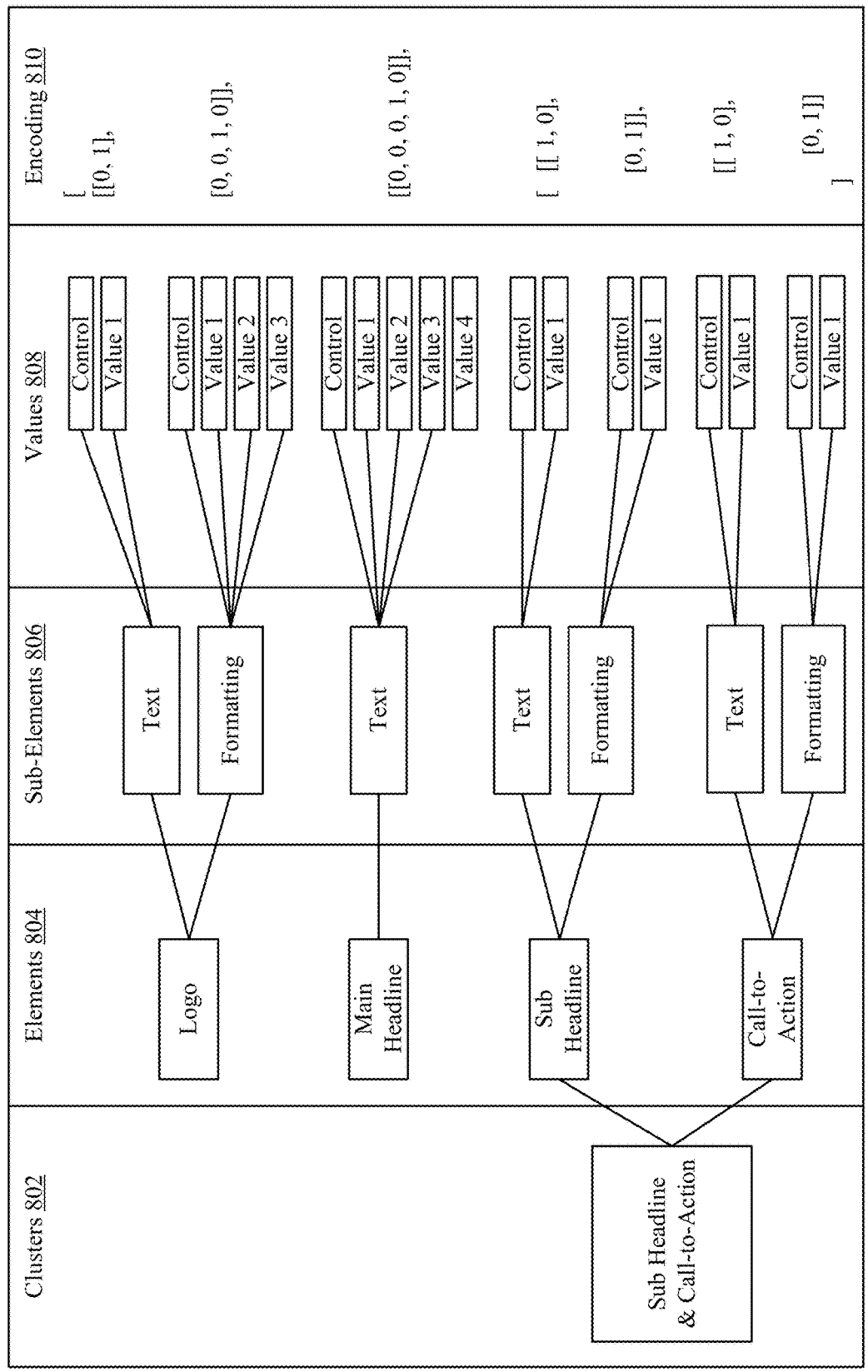
FIG. 8 depicts a symbolic drawing of one implementation of encoding starter dimensions and starter dimension values of a starter funnel.

FIG. 8 depicts a symbolic drawing of one implementation of encoding starter dimensions and starter dimension values of a starter funnel. In FIG. 8, clusters 802, elements 804, sub-elements 806, and sub-element values 808 corresponding to the sub-elements 806 of the starter funnel are encoded into a binary string encoding 810. In the binary string encoding 810, the left most bit for each sub-element value is the control value. In other implementations, the binary string encoding 810 can be based on other schemes relying on data types other than binary data type (0 or 1), such as quantitative or numerical data type, qualitative data type, discreet data type, continuous data type (with lower and upper bounds), integers data type (with lower and upper bounds), nominal data type, ordinal or ranked data type, categorical data type, interval data type, and/or ratio data type. For example, the binary string encoding 810 can be based on, or any combination thereof, real values between 0 and 1, continuous values such as Red, Green, Blue (RGB) values between 0 and 256, hexadecimal values of CSS colors (e.g., #F0F8FF), categorical color values of CSS colors (e.g., AliceBlue), respective values of other CSS property groups and properties, size of a particular dimension (e.g., height and width), a set of different values and data types (e.g., different numeric dollar price values or a combination of different numeric dollar price values and heights and widths), and others.

Figure 9:
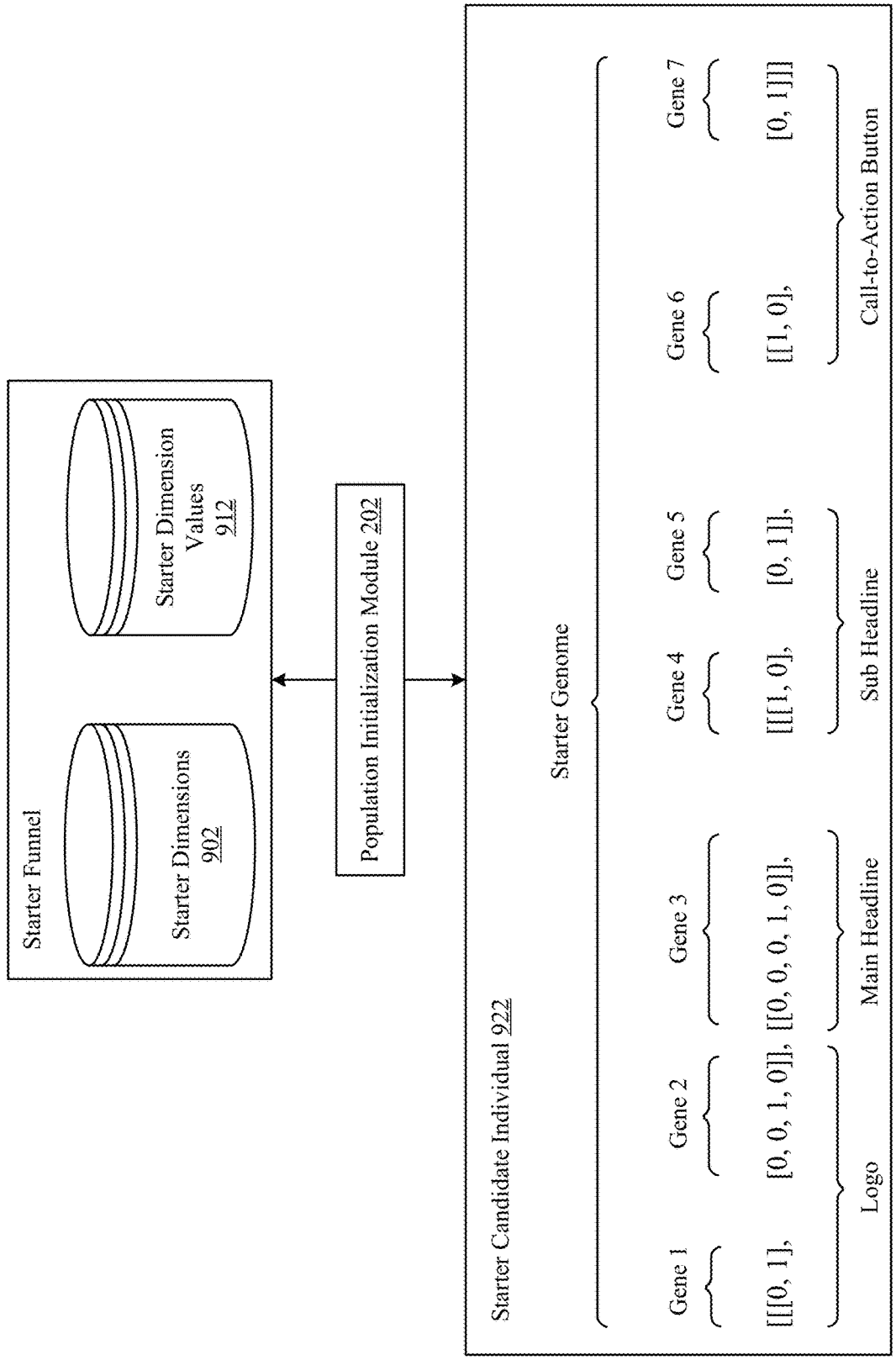
FIG. 9 illustrates one implementation of encoding starter dimensions and starter dimension values of a starter funnel into a starter candidate individual/starter genome.

FIG. 9 illustrates the population initializer 202 encoding starter dimensions 902 and starter dimension values 912 of a starter funnel into a starter candidate individual/starter genome. In particular, the encoding produces a binary sequence representing a starter candidate individual 922. The encoding of the starter candidate individual 922 is shown below:

```
[
    [ [0, 1],   [0, 0, 1, 0] ],           Logo
    [ 0, 0, 0, 1, 0         ],            Main Headline
    [                                     Cluster
        [ [1, 0],   [0, 1] ],             Sub Headline
        [ [1, 0],   [0, 1] ],             Call-to-Action
    ]
]
```

Starter candidate individual 922 includes seven genes corresponding to each of the seven sub-elements 806. The left most bit of each gene is the control value. In other implementations, the encoding of the starter candidate individual 922 can be based on other schemes relying on data types other than binary data type (0 or 1), such as quantitative or numerical data type, qualitative data type, discreet data type, continuous data type (with lower and upper bounds), integers data type (with lower and upper bounds), nominal data type, ordinal or ranked data type, categorical data type, interval data type, and/or ratio data type. For example, the encoding of the starter candidate individual 922 can be based on, or any combination thereof, real values between 0 and 1, continuous values such as Red, Green, Blue (RGB) values between 0 and 256, hexadecimal values of CSS colors (e.g., #F0F8FF), categorical color values of CSS colors (e.g., AliceBlue), respective values of other CSS property groups and properties, size of a particular dimension (e.g., height and width), a set of different values and data types (e.g., different numeric dollar price values or a combination of different numeric dollar price values and heights and widths), and others.

With the initialization and encoding of the starter candidate individual understood, the discussion now turns to how the candidate search space is defined.

Candidate Search Space Definition

As discussed above, the candidate search space is defined based on the starter funnel. In particular, the population initializer 202 defines the candidate search space by subjecting the starter dimensions and starter dimension values of the starter funnel to combinatorial operations. In one example, if the designer specifies 4 starter page elements (e.g., logo, main headline, sub headline, call-to-action), 7 possible starter sub-elements, and 19 possible starter sub-element values, then a candidate search space with 640 possible combinations of dimensions and dimension values is defined by subjecting 8 different variations of the logo, 5 different variations of the main headline, 4 different variations of the sub headline, and 4 different variations of the call-to-action to combinatorial operations (i.e., 8×5×4×4=640).

With the definition of the candidate search space understood, we now turn to how various generations of the evolutionary computations disclosed herein are optimized.

Generation Optimization

Starter Funnel Based Optimization

Figure 10:
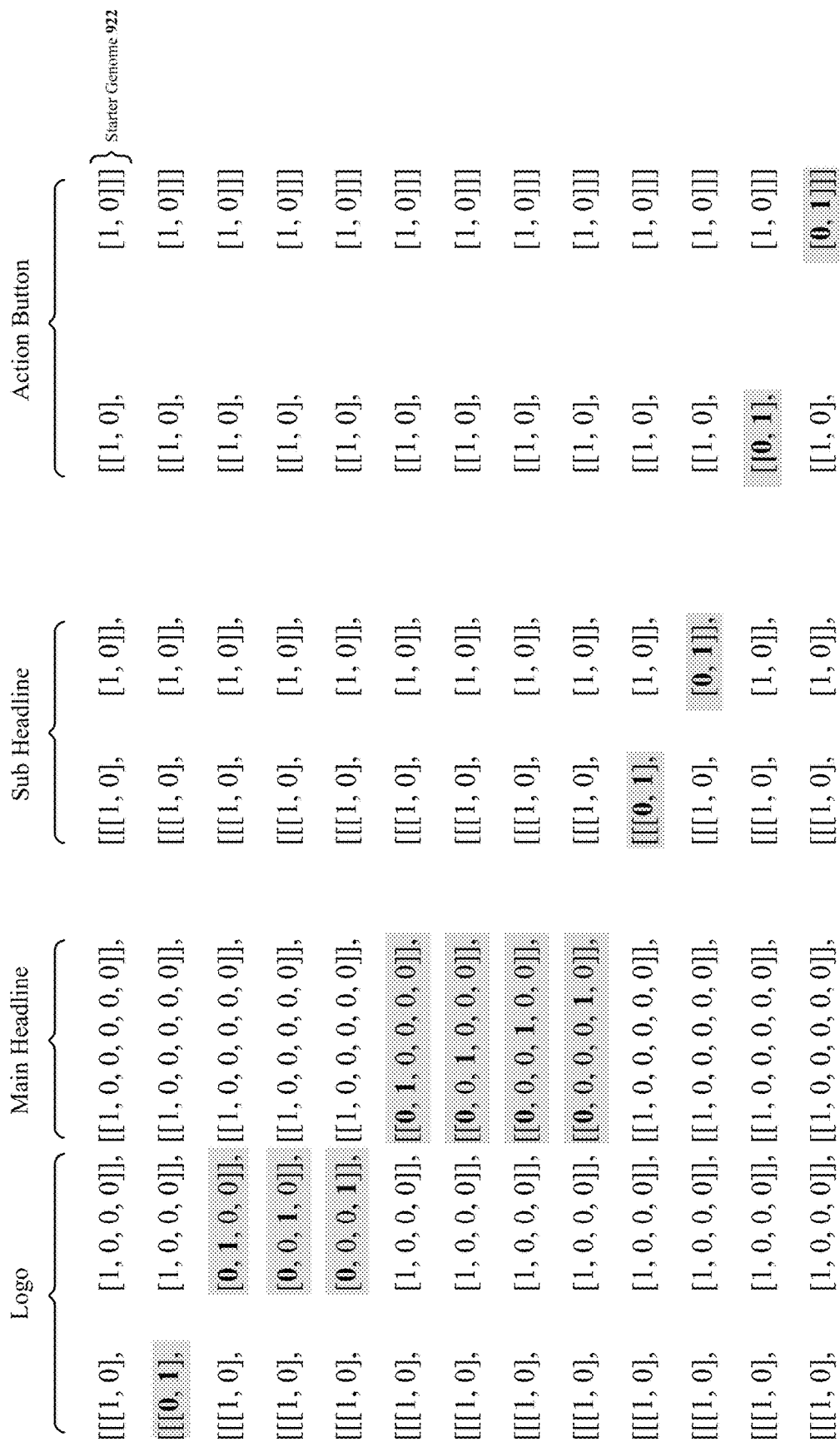
FIG. 10 depicts one implementation of initializing a first generation based on a starter funnel.

In implementations, the population initializer 202 creates the preliminary pool of candidate individuals (e.g., a first generation) in dependence upon at least one starter funnel and the starter dimensions and starter dimension values of its starter web interfaces (e.g., starter candidate individual 922). In one implementation, candidate individuals in the first generation are initialized in a manner that ensures that each of the starter dimension values occurs in only one of the initialized individuals of the first generation. FIG. 10 depicts such an implementation. In FIG. 10, the starter candidate individual 922 has 7 genes and 19 possible gene values. As a result, in just the starter candidate individual 922, 7 of the 19 gene values are initialized. Accordingly, the population initializer 202 creates 12 additional genomes such that the remaining 12 possible gene values are initialized in the respective 12 additional genomes. In FIG. 10, the 12 possible gene values are depicted with a grey background. Thus, in the example where the candidate search space comprised 640 possible combinations of dimensions and dimension values, only a subset of the 640 possible combinations (e.g., 13 combinations in FIG. 10) is initialized in the first generation.

In another implementation, candidate individuals in the first generation are initialized in a manner that ensures that each of the starter dimension value occurs in at least one of the initialized individuals of the first generation.

In another example, assume that a starter genome is specified to include 28 starter dimension values for a set of starter dimensions. Note that some or all of the 28 starter dimension values can apply to the same starter dimension or to a set of different starter dimensions. Thus, in some instances, multiple starter dimension values from the 28 starter dimension values apply to a single starter dimension, which is a member of a group consisting of a plurality of starter dimensions. In the example shown in FIG. 5, the "headline font" starter dimension can have five different starter dimension values, namely "Audiowide", "Impact", "Cambria 20px", "American Typewriter", and "Copperplate". Similarly, the "headline text" starter dimension can have five different starter dimension values as well, namely "Don't miss the live auction", "Only a few minutes left! Live Auction", "You can Win Your Car!", "When it's gone, it's gone forever", and "Win Your Dream Car!". In the same vein, the "sub-headline background color" starter dimension can have four different starter dimension values, namely blue, cyan, orange, and red. Also, the "sub-headline text" starter dimension can have four different starter dimension values, namely "Go!", "Go to the Auction!", "Win the Auction!", and "Win it NOW!".

Accordingly, in one implementation, the first generation is initialized in a manner that ensures that each of the 28 starter dimension values is included in only one of the candidate individuals of the first generation. In another implementation, the first generation is initialized in a manner that ensures that each of the 28 starter dimension values is included in at least one of the candidate individuals of the first generation. In such implementations, multiple starter dimension values from the 28 starter dimension values are included in a single candidate individual of the first generation. This ensures that each of the starter dimensions and dimension values identified in one or more starter dimensions are provided as input to the disclosed evolutionary computations so that the performance measures 106 can be developed for them during the live online evaluation 108.

In other implementations, the candidate individuals are initialized by randomly selecting from the candidate search space an available value for a set of dimensions. In yet other implementations, the candidate individuals are initialized in a maximally uniform manner across the distribution of dimension values in the candidate search space in dependence upon a predetermined number of candidate individuals to be created. In one implementation, once created, a candidate individual is stored in the candidate individual population 102 as a vector having a particular value for each dimension.

Test Parameters Based Optimization

The evolutionary computations disclosed herein customize the MLCO in dependence upon one or more test parameters specific to a particular organization seeking promotion of the target user behavior. Examples of such test parameters include live user traffic registered or received by the organization (e.g., on a weekly, monthly, quarterly, or other calendar basis) and the performance measures 106 (e.g., conversion rate, revenue rate (determined over a sample of users)) registered by the organization. In implementations, values for such test parameters are provided by the organization or determined over an initial testing period.

Additionally, since live user traffic is a valuable commodity in a webpage testing environment, the evolutionary computations disclosed herein generate and process the various generations in an efficient manner. In one implementation, the evolutionary computations disclosed herein achieve such efficiency by ensuring that, given an amount of live user traffic received by an organization during a time period (e.g., in a week or month), a minimum number of evolutionary computation loops are completed within the time period to yield evolved candidate individuals that have been determined by the live online evaluation 108 to have superior values for the performance measures 106. So, in one example, if the amount of live user traffic received by an organization during a month is hundred thousand users (i.e., 100,000 users/month), then the evolutionary computations disclosed herein can be configured to generate and process at least three generations within the month.

In another implementation, such efficiency is achieved by ensuring that, given an amount of live user traffic received by an organization during a time period (e.g., in a week or month), a minimum number of candidate individuals are evolved (or subjected to the live online evaluation 108 over a sample of users) within the time period and/or only a limited number of candidate individuals are processed at each generation so that multiple generations are evolved within the time period. So, in one example, if the amount of live user traffic received by an organization during a month is hundred thousand users (i.e., 100,000 users/month), then the evolutionary computations disclosed herein can be configured to generate and process at least fifty candidate individuals across three generations within the month such that each candidate individual is live evaluated by at least two thousand users. In another example, the evolutionary computations disclosed herein can be configured to generate and process no more than seventeen candidate individuals at each of the three generations.

In yet another implementation, a specialized scheme for initializing the first generation includes making a maximum population size of the candidate individual population a function of the live user traffic and the performance measures 106 (e.g., conversion rate, revenue rate (determined over a sample of users). Furthermore, when a maximum population size calculated for an organization based on its live user traffic and performance measures 106 is not consistent with the number of starter dimensions and/or the number of starter dimension values specified by the organization's designer, the evolutionary computations disclosed herein use specialized selection schemes to select starter dimensions and starter dimension values for candidate individual initialization in a manner that ensures a population size of the candidate population at some (e.g., just the first generation) or at all generations is constrained by the maximum population size calculated for the organization. In one implementation, this is achieved by traversing the starter dimensions and/or the starter dimension values on a gene-by-gene basis and only selecting a subset of values in each gene and/or only a subset of genes for candidate individual initialization. In such an implementation, the selection of the subset of values in each gene and/or the subset of genes can be biased for earlier values and/or earlier genes or later values and/or later genes, can be uniform selection of genes and/or values at the gene-level, can be one-point selection of genes and/or values at the gene-level, can be two-point selection of genes and/or values at the gene-level, or can be random selection of genes and/or values at the gene-level. In other implementations, the selection of genes and/or values at the gene-level can be based on any other conventional or future-developed selection technique.

In another implementation, the maximum population size-based constraint is achieved by distributing selection of the starter dimensions and/or the starter dimension values across different generations such that some subsets of the starter dimensions and/or the starter dimension values specified by the organization's designer are selected in earlier generations and other subsets are selected at later generations. The selection of subsets can be uniform, one-point, two-point, random, or can be based on any other conventional or future-developed selection technique.

Assume, in one example, that given the amount of live user traffic received by an organization during a month is fifty thousand users (i.e., 50,000 users/month) and that each candidate individual is supposed to be live evaluated by at least two thousand users, the maximum population size determined for the organization is twenty-five candidate individuals across three generations. Also assume that the organization's designer has selected thirty starter dimensions, each with four starter dimension values. If the standard initialization scheme is implemented, which requires each starter dimension value to occur in only one candidate individual, a hundred and twenty starter dimension values would require at least ninety one (91) candidate individuals to be created in just the first generation. However, this would in conflict with the maximum population size of twenty-five calculated for the organization, which limits candidate individual count in a given generation to either eight or nine.

To resolve this conflict, the specialized initialization and selection schemes of the evolutionary computations disclosed herein can select a subset of the hundred and twenty starter dimension values and/or a subset of the thirty starter dimensions to initialize only eight candidate individuals in each of the first and second generations and only nine candidate individuals in the third generation, according to one implementation. In implementations, the selection can be random or biased towards earlier or later starter dimension values and/or starter dimensions. In other implementations, the starter dimension values and/or the starter dimensions that are not selected during the first generation can be included in the candidate population at the end of the second generation, or at any other subsequent generation.

In implementations, any stage and/or generation (e.g., first, second, third, fourth, tenth, or twentieth generation, and so on) of the evolutionary computations disclosed herein can utilize the specialized and/or the standard initialization schemes. As used herein, the term "initialization" or "initialize" refers to an evolutionary operation that can be applied at any generation of the evolutionary computations to create and/or procreate new candidate individuals.

With the population initialization understood, we turn to how the individuals are tested.

Testing Individuals

Further to FIG. 2, conversion system 104 includes a candidate processing module 220 which comprises a candidate tester 212, a competition updater 222 and a procreator 228. Candidate tester 212 tests the candidate individuals in the candidate individual population 102. Each candidate individual undergoes a battery of tests or trials, each trial testing the candidate individuals on one or multiple samples of users with sample sizes ranging from hundreds, thousands, and millions of users. In another implementation, the number of tests or sample size is determined by parameters associated with the test. Examples of such test parameters include number of visitors per unit time, existing conversion rate, size of the candidate search space, preferred risk tolerance, and the type of performance measure. The tests or trials are implemented as the live online evaluation 108 where funnels generated in dependence upon the candidate individuals are presented to real world users for testing. Then, the performance measures 106 are collected based on the live online evaluation 108 during which the real world users interact with the funnels. The candidate tester 212 updates the performance measures 106 associated with each of the tested candidate individuals on a real time basis. The frequency of the updates is also determined by the test parameters.

Fitness-Proportionate Procreation

To consume the live user traffic efficiently, the evolutionary computations disclosed herein, in some implementations, use specialized procreation schemes to create a second generation of individuals. In one implementation, a specialized scheme for procreating the second generation includes the procreator 228 subjecting genomes created during the first generation, i.e., parent genomes, to fitness-proportionate selection (e.g., roulette wheel selection, stochastic universal sampling). In such an implementation, every parent genome has a chance of being selected to breed, but fitter parent genomes are more likely to be chosen than weaker parent genomes. This is achieved by making a parent genome's selection probability a function of its fitness defined by the performance measures 106 (e.g., conversion rate, revenue rate (determined over a sample of users)). For example, the probability for selecting each candidate for procreation is proportionate to their fitness scores (i.e., candidate individual is fitness-proportionally selected from parent candidate individuals). For example, suppose there are 3 candidates with fitness scores of 2, 3 and 5, respectively. The probability for selecting them is then 20% (2/(2+3+5)), 30% ((3/(2+3+5))) and 50% ((5/(2+3+5))), respectively. In the case that 2 candidates out of these 3 candidates need to be selected, the fitness proportionate selection is performed once to select one candidate first, and then process is repeated with the first candidate eliminated. For example, the probability of selecting the other two candidates is 40% (2/(2+3)) and 60% (3/(2+3)), respectively.

In one implementation, the selection from a given parent genome is done on a gene-by-gene basis in dependence upon the selection probability of a particular gene. In some implementations, the particular gene's selection probability is a function of the performance measures 106 (e.g., conversion rate, revenue rate (determined over a sample of users)) of the genome that contains the particular gene. Accordingly, the resulting genomes in the second generation include genes selected from the parent genomes in dependence upon their respective selection probabilities.

In yet another implementation, the second generation is procreated by making random selections from the parent genomes on a gene-by-gene basis.

In implementations, any stage and/or generation (e.g., first, second, third, fourth, tenth, or twentieth generation, and so on) of the evolutionary computations disclosed herein can utilize the specialized procreation schemes.

After procreation, the candidate tester 212 operates again on the updated candidate individual population 102. The process continues repeatedly. In implementations, a controller 230 iterates the candidate tester 212 and the procreator 228.

Competition

In one implementation, the evolutionary computations utilize a competition updater 222, which is operationalized in certain generations. The competition updater 222 updates the candidate individual population 102 contents in dependence upon the updated performance measures 106. In some implementations, the competition updater 222 discards candidate individuals that do not meet a minimum baseline individual fitness (e.g., pre-set by an administrator or automatically set), or candidate individuals whose "individual fitness" relatively lags the "individual fitness" of similarly tested candidate individuals. The candidate individual population 102 is updated with the revised contents.

The competition updater 222 manages graduation of candidate individuals from one generation to the next. This process can be thought of as occurring one candidate individual at a time, as follows. First, a loop is begun through all candidate individuals for whom the performance measures 106 have been updated since the last time the competition updater 222 was executed. In one implementation, if the performance measures 106 for a current candidate individual are still below a baseline individual fitness (e.g., pre-set by an administrator or automatically set) or are sufficiently lagged relative to individual fitness of other candidate individuals, then the current candidate individual is discarded and the next one is considered. If the performance measures 106 for the current individual are above a baseline individual fitness (e.g., pre-set by an administrator or automatically set) or are relatively on par with individual fitness of other candidate individuals, then the current candidate individual is added to the next generation. The process then moves on to consider the next candidate individual in sequence. In an implementation, the competition updater 222 identifies the candidate individuals that are above or below baseline individual fitness using the average neighborhood fitness, as described in more detail below.

Relative Performance Measure

High performance measures of individuals with less experience could be due to luck rather than true fitness (e.g., due to unrealistic affinity of the users to an individual due to holiday season). That is, if compared to other individuals that have much more experience, younger, luckier individuals that have been determined to have high performance could still displace individuals whose fitness levels are lower but more realistic. Allowing such individuals to compete against each other solely on the basis of absolute fitness would optimize the evolutionary computations for individuals that are lucky.

A solution to this problem is that candidate individuals be compared based on their "relative performance measures", instead of their absolute performance measures. A relative performance measure of a candidate individual is calculated based on the difference between an absolute performance measure of a control individual determined in a first time period and an absolute performance measure of the candidate individual also determined in the first time period. So, for example, if a first candidate individual created during a first generation has an absolute average conversion rate of 40% and a first control individual also initialized in the first generation has an absolute average conversion rate of 35%, then the relative performance measure of the first candidate individual is 5% (40%−35%=5%). Similarly, if a second candidate individual created during a second generation has an absolute average conversion rate of 45% and the first control individual's absolute average conversion rate in the second generation has increased to 42%, then the relative performance measure of the second candidate individual is 3% (45%−42%=3%). Accordingly, the first and second candidate individuals are compared based on their respective relative performance measures and the first candidate individual is found to be 2% better than the first candidate individual (5%−3%=2%), even though the absolute performance measure of the second candidate individual is 5% (45%−40%=5%) higher than that of the first candidate individual. Each comparison made by the competition updater 222 between the relative performance measure of one individual and that of another is sometimes referred to herein as a comparison "instance".

In one implementation, the competition updater 222 determines whether the relative performance measure of the current candidate individual exceeds that of the least fit candidate individual in the candidate individual population 102. If so, then the least fit candidate individual is discarded, and the current candidate individual is moved to the next generation. If not, then the current candidate individual is discarded. The process then moves on to consider the next candidate individual in sequence.

Crossover and Mutation Based Procreation

Regarding procreation, any conventional or future-developed technique can be used for procreation. In an implementation, conditions, outputs, or rules from parent individuals are combined in various ways to form child individuals, and then, occasionally, they are mutated. The combination process for example may include crossover—i.e., exchanging conditions, outputs, or entire rules between parent individuals to form child individuals. New individuals created through procreation begin with performance measures that are indicated as undefined.

The procreator 228 adds to the candidate individual population 102 new individuals formed in dependence upon a respective set of one or more parent individuals from the candidate individual population 102 and not yet selected for discarding by the competition updater 222. In one implementation, a third generation of genomes is created by selecting pairs of parent genomes from the second generation and subjecting the parent genome pairs to a crossover scheme. In other implementations, procreation (e.g., crossover and/or mutation) can be initiated at any other generations, such as the first, second, fourth, or tenth generation, and so on.

Crossover

Regarding crossover, parent genome pairs are identified for crossover when a subsequently selected second parent genome differs from a first parent genome selected from the candidate population immediately before the second parent genome. In implementations, a parent genome can be selected to participate in multiple crossover operations during the same generation. In some implementations, within a given generation, a variety of crossover schemes are used to carry out crossover between parent genome pairs until a count of offspring genomes reaches the maximum population size determined for the given generation. In one implementation, the crossover occurs on a gene-by-gene basis. So, in one example, parent genomes can crossover based on sub-elements 806 and/or sub-element values 808, shown in FIG. 8. In other implementations, the crossover schemes applied at the gene-level to evolve a particular generation can be based on a variety of crossover schemes such as uniform crossover (e.g., selecting gene values alternatively from the parent genome pairs), one-point crossover, two-point crossover, and/or random crossover. In yet other implementations, the crossover schemes applied at the gene-level to evolve a particular can be based on any other conventional or future-developed crossover technique.

Figure 11:
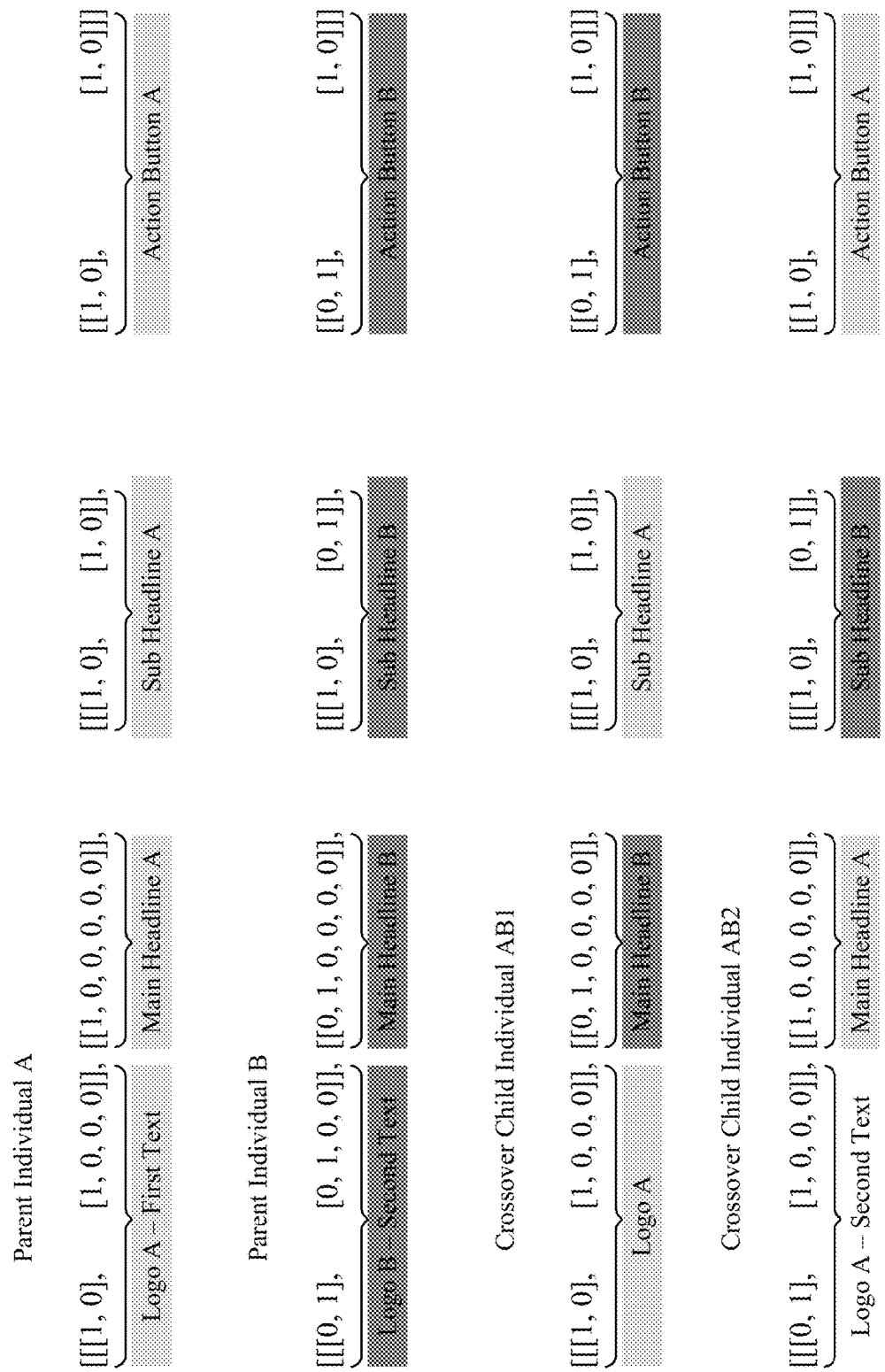
FIG. 11 shows a symbolic drawing of one implementation of procreating new candidate individuals using a crossover technique.

FIG. 11 shows a symbolic drawing of one implementation of procreating new candidate individuals using a crossover technique. In FIG. 11, a binary sequence of parent candidate individual A represents logo A with first text type (e.g., Times Roman), main headline A, sub headline A, and action button A. Also in FIG. 11, a binary sequence of parent candidate individual B represents logo B with second text type (e.g., Arial), main headline B, sub headline B, and action button B. In one exemplary implementation, the procreator 228 creates a crossover child individual AB1 that includes logo A and sub headline A from parent candidate individual A, and includes main headline B and action button B from parent candidate individual B. In another exemplary implementation, the procreator 228 creates a crossover child candidate individual AB2 that includes logo A (from parent candidate individual A) with second text type (e.g., Arial) (from parent candidate individual B) and sub headline B from parent individual B, and also includes main headline A and action button A also from parent candidate individual A.

Mutation

Figure 12:
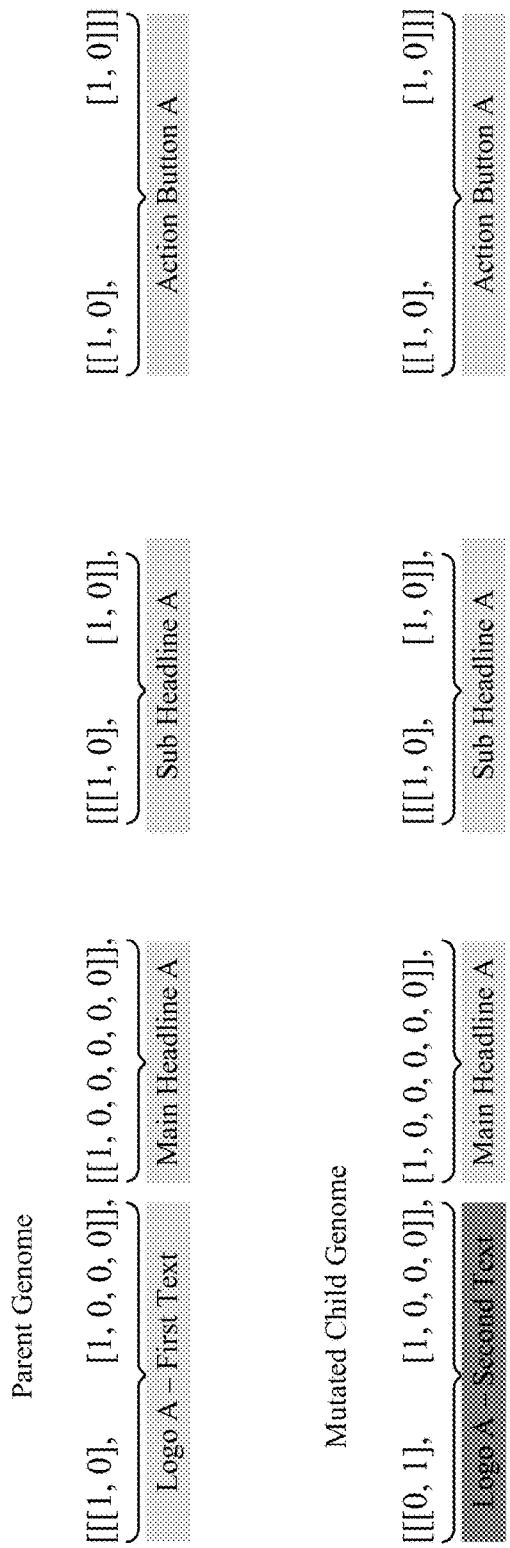
FIG. 12 is a symbolic drawing of one implementation of procreating candidate individuals using a mutation technique.

FIG. 12 is a symbolic drawing of one implementation of procreating candidate individuals using a mutation technique. In FIG. 12, a first gene of a parent genome is mutated such that text type of logo A is mutated from a first text (e.g., Times Roman) to a second text (e.g., Arial).

Preferably, procreation involves crossover to create a small predetermined number of new individuals followed by mutation of only a small subset of the new individuals. Mutation does not increase the number of candidate individuals in this implementation; it merely modifies individuals that were created by crossover.

The evolutionary computations disclosed herein use mutation to avoid or overcome local maxima. Accordingly, in some implementations, the evolutionary computations disclosed herein are configured to carry out mutation only after carrying out crossover in a certain number of generations and/or after carrying out crossover in a certain number of procreation operations within the same generation (e.g., mutation occurs only after the third generation). In other implementations, procreation (e.g., crossover and/or mutation) can be initiated at any other generations, such as the first, second, third, fourth, or tenth generation, and so on.

In implementations, each parent genome is assigned a genome mutation probability that determines the likelihood of a parent genome being subjected to mutation at all during a generation. The "genome mutation probability" can be based on any probability scheme such as random probability, uniform probability, weighted probability, and/or fitness-proportionate probability. When a parent genome is selected, the mutation occurs on a gene-by-gene basis, according to one implementation. So, in one example, parent genomes can be mutated based on sub-elements 806 and/or sub-element values 808, shown in FIG. 8.

Within a parent genome, the selection of genes and/or gene values for the gene-by-gene mutation can be based on a "gene mutation probability". The gene mutation probability can be based on any probability scheme such as random probability, uniform probability, weighted probability, and/or fitness-proportionate probability. So, for example, a Boolean or binary or vector encoding of a genome (such as the ones shown in FIG. 12) can be mutated on a gene-by-gene basis based on any probability scheme. In other implementations, the mutation at the gene-level can be uniform mutation, non-uniform mutation, boundary mutation, and/or gradient mutation. In yet other implementations, the mutation at the gene-level can be based on any other conventional or future-developed mutation technique.

With the procreation of individuals understood, we now turn to how the evolutionary computations disclosed herein accelerate traversal of the candidate search space using pseudo-evolution.

Accelerated Pseudo-Evolution

Performance efficiency is paramount for effective implementation of MLCO. The evolutionary computations disclosed herein add performance efficiency to the evolutionary process by accelerating traversal of the candidate search space (e.g., small search spaces). As discussed above, the candidate search space identifies all possible combinations of dimensions and dimension values; however only a subset of the combinations is initialized in each generation. Following the example used above, if the candidate search space identifies 640 combinations of dimensions and dimension values, then only 13 combinations are initialized in the first generation. Furthermore, whenever a previously generated combination (i.e., candidate individual or genome) is re-generated during a generation or between generations, it is identified as a duplicate and rejected. An evolutionary event or operation that produces a duplicate is referred to herein as a "collision". Collisions cause performance inefficiencies because the results of the collisions (i.e., duplicates) are rejected and do not advance the evolutionary process.

In one example, a spike in a collision count can occur when a majority of the all possible combinations of dimensions and dimension values have already been generated and the evolutionary operations frequently create duplicates. As a result, it could take substantial time to generate the remaining combinations of dimensions and dimension values. Following the example used above, if 620 of the 640 possible combinations are created over 50 generations, then routine evolution could take another 20-50 generations to create the remaining 20 combinations.

The evolutionary computations disclosed herein solve this technical problem by switching to pseudo-evolution when a collision count reaches a pre-set threshold. In one implementation, the evolutionary computations disclosed herein track which of the all possible combinations of dimensions and dimension values have already been generated (e.g., using an annotation and/or enumeration scheme), and when the collision count reaches the pre-set threshold, they randomly generate only those combinations (i.e., candidate individuals or genomes) that have not been yet generated. Accordingly, the evolutionary process is made to artificially focus only on those combinations that have not been selected or created during any of the preceding generations. This is referred to herein as "pseudo-evolution". Pseudo-evolution accelerates the evolutionary process because it bypasses the routine evolution (e.g., terminates, parallelizes, overrides, or avoids initialization and/or procreation schemes) and creates the remaining combinations in much fewer generations. Following the example used above, if 620 of the 640 possible combinations are created over 50 generations and the collision count reaches a threshold of 10, then the pseudo-evolution can exclusively utilize the next 2 generations to only create the remaining 20 combinations.

Evolution Pseudo Code

The following pseudo code shows one implementation of the evolutionary computations:

```
set_evolution_parameters
create_candidates_generation_1
repeat
    repeat
        test_candidates
    until candidate_spread_is_sufficient or remove_criteria_is_met
    remove_low_performing_candidates
    create_new_candidates
Until performance_is_sufficient or no_more_designs_are_possible
```

The following Extended Backus-Naur Form shows another implementation of the evolutionary computations:

```
genome ::= [ element_cluster+ ]
element_cluster ::= [ element+ ] | element
element ::= [ action+ ]
action ::= [ control, action_value ]
action_value ::= text | formatting | html | hid | remove | image | class | custom
text, formatting, html, image, class, custom ::= bit_value
hide, remove ::= bit_value
bit_value ::= 0 | 1
```

The discussion now turns to how candidate individuals are used to generate funnels and comprising web interfaces for frontend presentation to the end users.

Frontend Presentation

Figure 13:
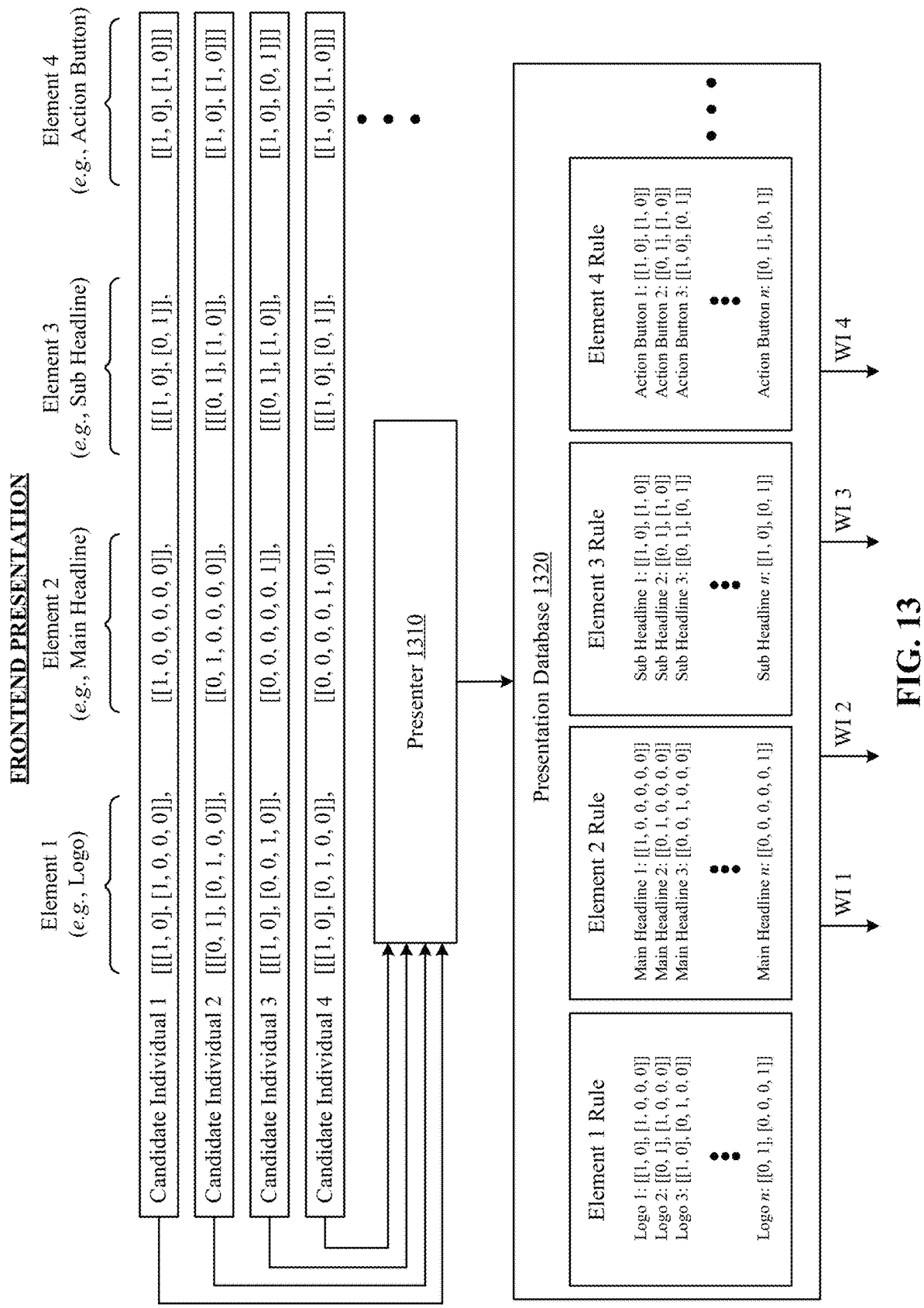
FIGS. 13 and 14 show one implementation of generating funnels of one or more web interfaces in dependence upon corresponding candidate individuals for frontend presentation to the end users.
Figure 14:
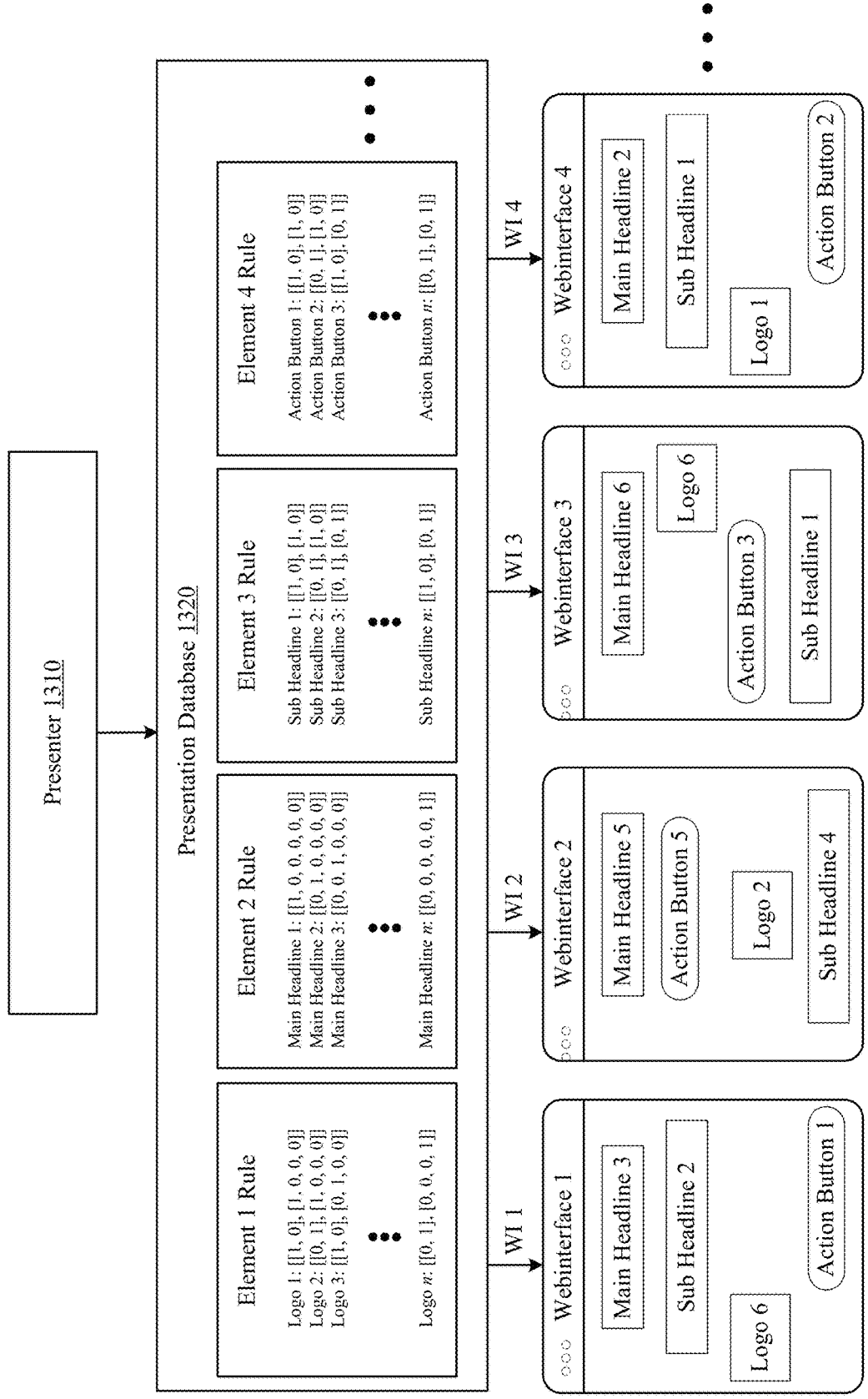

FIGS. 13 and 14 show one implementation of generating funnels of one or more web interfaces in dependence upon corresponding candidate individuals for frontend presentation to the end users. FIG. 13 shows four candidate individuals (CI 1 to CI 4) based on which four web interfaces are generated. Individuals (CI 1 to CI 4) can be any candidate individuals in the candidate individual population 102, i.e., they can be the candidate individuals for whom the performance measures 106 are developed during the live online evaluation 108.

FIG. 13 also shows that each genome is represented by a binary sequence (string). Each binary sequence is further compartmentalized into sub-sequences (sub-strings) referred to herein as "genes". Each gene represents a dimension and corresponding dimension value for a funnel (e.g., characteristics of a webpage or a funnel including webpages). Accordingly, each gene identifies a sub-element and corresponding sub-element value for the web interfaces that are to be generated in dependence upon the genomes (CI 1 to CI 4). In implementations where the web interfaces are frontend (e.g., graphical) objects comprising content, the genes identify frontend (e.g., graphical) elements/components and corresponding element/component values that are to be included in the web interfaces generated based on the genomes (CI 1 to CI 4).

Note that in the implementation of FIGS. 13 and 14, each element of a funnel is encoded as a fixed-length substring of bits grouped as genes. For example, the sub headline element has four bits grouped into two genes. For each gene, only one of the bits can be active or "hot" (e.g., represented by "1") so as to identify a particular dimension value from a set of available dimension values. The leftmost bit represents the "control" value of a gene, which, in one example, for main headline might indicate "plain text". The second, third, and forth bits might, for example, indicate "bold", "italics", and "bold underlined", respectively. It will be appreciated that many other encodings are possible in different implementations. For example, a 2-bit numeric value might be used, with "0" indicating the control, "1" indicating "bold", "2" indicating "italics", and "3" indicating "bold underlined".

In other implementations of FIGS. 13 and 14, a genome can be represented and comprising elements encoded using other schemes relying on data types other than binary data type (0 or 1), such as quantitative or numerical data type, qualitative data type, discreet data type, continuous data type (with lower and upper bounds), integers data type (with lower and upper bounds), nominal data type, ordinal or ranked data type, categorical data type, interval data type, and/or ratio data type. For example, the encoding of the genomes and the comprising elements in FIGS. 13 and 14 can be based on, or any combination thereof, real values between 0 and 1, continuous values such as Red, Green, Blue (RGB) values between 0 and 256, hexadecimal values of CSS colors (e.g., #F0F8FF), categorical color values of CSS colors (e.g., AliceBlue), respective values of other CSS property groups and properties, size of a particular dimension (e.g., height and width), a set of different values and data types (e.g., different numeric dollar price values or a combination of different numeric dollar price values and heights and widths), and others.

The genomes (CI 1 to CI 4) are generated and provided by the conversion system 104 using the disclosed evolutionary computations, as discussed above. The conversion system 104 then utilizes a presentation database 1320 and a presenter 1310 to transform the genomes (CI 1 to CI 4) into funnels of one or more web interfaces.

The presentation database 1320 serves as a rule repository that identifies a frontend element value for each of at least one available value of each of the dimensions of the funnel. The presenter 1310 applies a selected one of the candidate individuals to the presentation database 1320 to determine frontend element values corresponding to dimension values identified by the selected candidate individual. Accordingly, the presenter 1310 is able to evaluate a genome provided by the conversion system 104 against the presentation database 1320 and generate an appropriate variation of the funnel based on the genome.

Presentation database 1320 includes various element rules. In the presentation database 1320, element rules are provided for all possible dimensions in the candidate search space, i.e., all possible frontend (e.g., graphical) elements/components that can be included in a web interface. Also, each element rule includes pointers identifying all possible dimension values or page element/component values for a given dimension or page element/component. For example, a "sub headline" element rule includes pointers for all possible properties of the "sub headline" element, such as color, text, size, placement, and the like.

For a selected genome, the presenter 1310 accesses the presentation database 1320 and evaluates the applicable element rule for each gene in the selected genome. In FIG. 13's example, element 1 rule is identified for all the logo genes, element 2 rule is identified for all the main head line genes, element 3 rule is identified for all the sub headline genes, and element 4 rule is identified for all the action button genes. Further, each element rule identifies a pointer for the respective gene values and generates corresponding frontend (e.g., graphical) elements/components and element/component values.

In one implementation, when one of the available values for each of the dimensions is a default value, the resulting the funnel has a default frontend element value for the default dimension value of each of the dimensions. In such an implementation, the presenter 1310 applies the selected candidate individual to the presentation database 1320 to determine frontend element values corresponding to all dimension values identified by the selected candidate individual other than the default dimension value for each of the dimensions.

In other implementations, a funnel customization specification memory is utilized, which stores, for a particular variation of the web interface funnel, a value for each of the dimensions of the funnel. In such an implementation, the presenter 1310 presents toward a user a funnel having frontend element values indicated by the presentation database 1320 as corresponding to the dimension values stored in the funnel customization specification memory. The funnel customization specification memory is also updated with a new set of values for each of the dimensions of the funnel. Updated values for the funnel customization specification memory are retrieved in response to user behavior for entering the funnel (e.g., user providing a landing page URL via a browser). In addition, the presenter 1310 accesses the presentation database 1320 in response to user behavior (e.g., user providing a landing page URL via a browser).

In one implementation, when one of the available values for each of the dimensions is a default value, the funnel has a default frontend element value for the default dimension value of each of the dimensions. In such an implementation, the funnel presented toward the user by the presenter 1310 has frontend element values indicated by the presentation database 1320 as corresponding to all of the dimension values identified in the funnel customization specification memory other than the default dimension value for each of the dimensions.

In FIG. 14, four web interfaces (WI 1 to WI 4) are generated by the presenter 1310 in dependence upon each of the candidate individuals (CI 1 to CI 4). Each of the web interfaces include frontend (e.g., graphical) elements/components and element/component values identified by the rules in the presentation database 1320. Then, the web interfaces (WI 1 to WI 4) are presented to the users for the live online evaluation 108.

Machine Learned User Device (MLUD)

Figure 15:
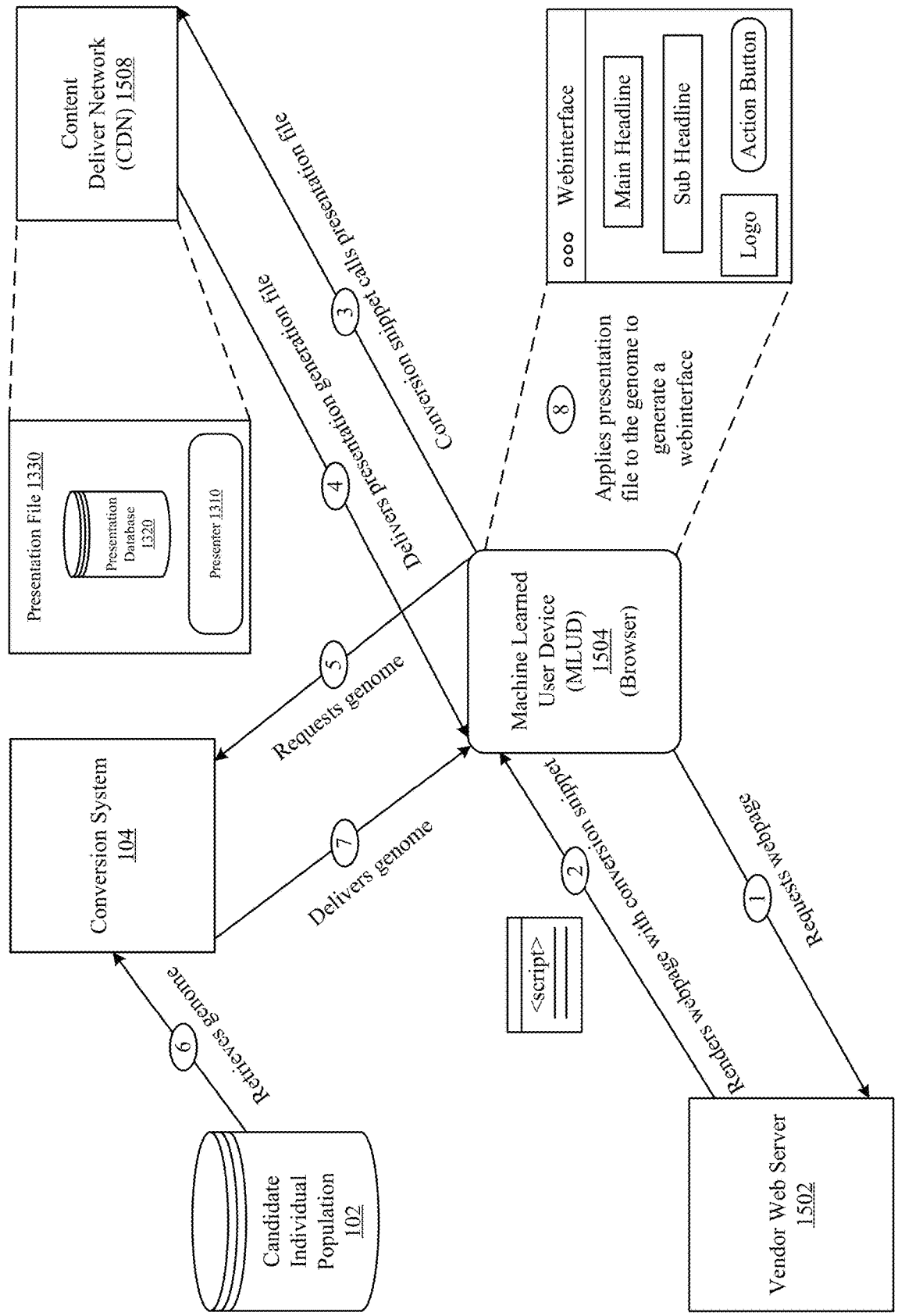
FIG. 15 is one implementation of a machine learned user device (MLUD).

FIG. 15 illustrates one implementation of an improved user device, referred to herein as the "machine learned user device" (MLUD). In FIG. 15, an end user uses a browser running on a MLUD 1504 to access a vendor website. The vendor web server 1502 is configured to deploy a conversion snippet, as part of a webpage, to the MLUD 1504 in response to the end user accessing the vendor website. After the conversion snippet is sent to the MLUD 1504 and before the webpage is rendered to the end user, the conversion snippet invokes a network server infrastructure. The network server infrastructure includes the conversion system 104, the candidate individual population 102, and a content delivery network (CDN) 1508.

The conversion snippet, deployed at the MLUD 1504, retrieves a presentation file 1330 from the CDN 1508 and stores the presentation file 1330 at the MLUD 1504. The CDN 1508 is pre-loaded with the presentation file 1330. Examples of common CDN services today include Akamai™, CloudFlare™, CloudFront™, Fastly™, MaxCDN™, KeyCDN™, Incapsula™, and GlobalDots™. The presentation file 1330 includes the presentation database 1320 and the presenter 1310, discussed above.

Then, the conversion snippet, deployed at the MLUD 1504, requests a genome from the conversion system 104. In response, the conversion system 104 retrieves a genome from the candidate individual population 102 and delivers the selected genome to the MLUD 1504.

Then, the MLUD 1504, having received the selected genome from the conversion system 104 and the presentation file 1330 from the CDN 1508, executes the presenter 1310. The presenter 1310 evaluates the selected genome against the rules of the presentation database 1320 and generates a funnel of one or more web interfaces, as discussed above. Accordingly, a standard user device is improved to generate algorithmically evolved web interfaces.

Machine Learned Content Delivery Network (MLCDN)

Figure 16:
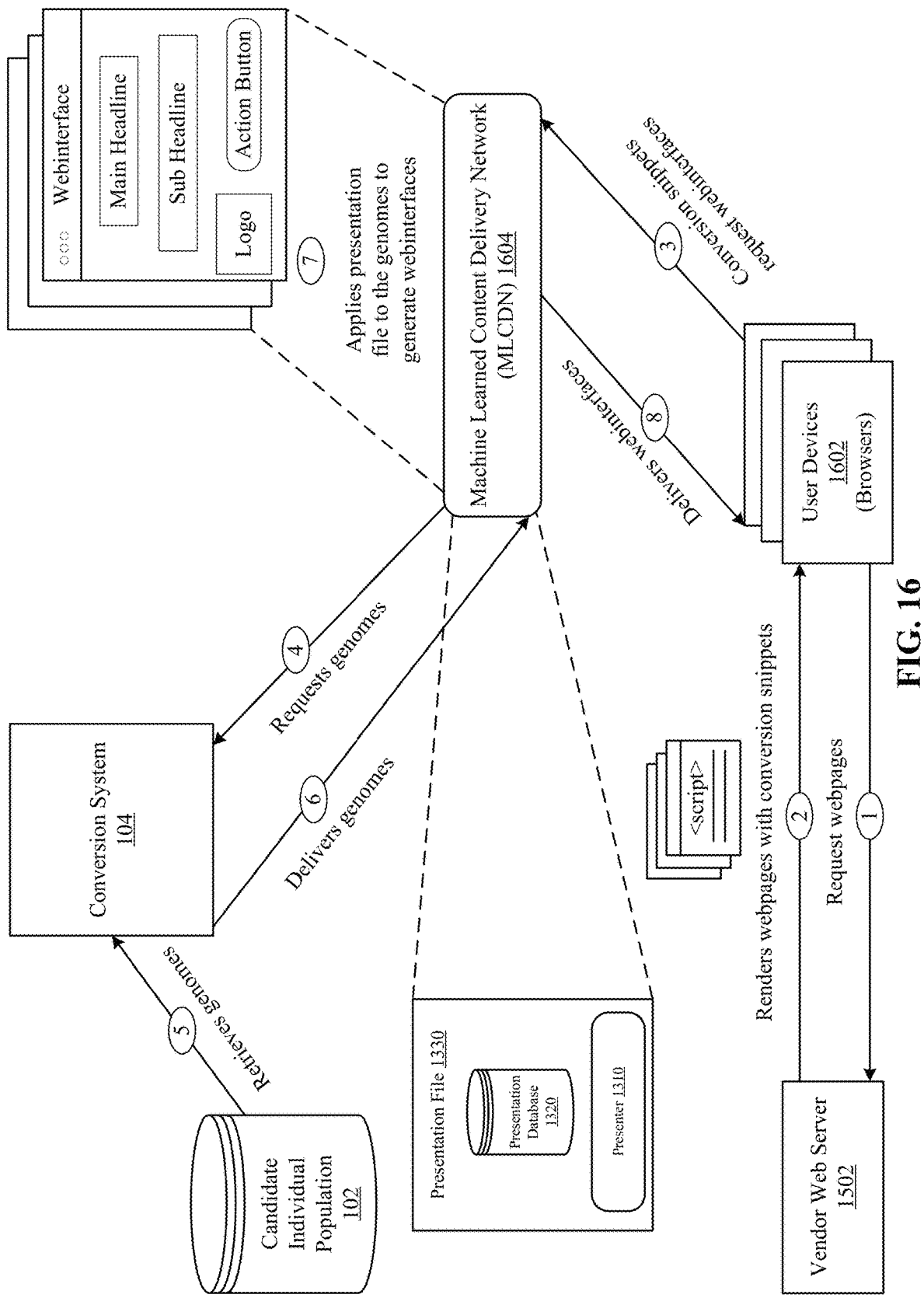
FIG. 16 illustrates one implementation of a machine learned content delivery network (MLCDN).

FIG. 16 illustrates one implementation of an improved content delivery network (CDN), referred to herein as the "machine learned content delivery network" (MLCDN). In FIG. 16, end users use browsers running on user devices 1602 to access a vendor website. The vendor web server 1502 is configured to deploy a conversion snippet, as part of a webpage, to the user devices 1602 in response to the end users accessing the vendor website. After the conversion snippet is sent to the user devices 1602 and before the webpage is rendered to the end users, the conversion snippet invokes a network server infrastructure. The network server infrastructure includes the conversion system 104, the candidate individual population 102, and a MLCDN 1604.

The MLCDN 1604 is pre-loaded with the presentation file 1330. The presentation file 1330 includes the presentation database 1320 and the presenter 1310, discussed above.

Then, the MLCDN 1604 requests a genome from the conversion system 104. In response, the conversion system 104 retrieves a genome from the candidate individual population 102 and delivers the selected genome to the MLCDN 1604.

Then, the MLCDN 1604, having both the selected genome and the presentation file 1330, executes the presenter 1310. The presenter 1310 evaluates the selected genome against the rules of the presentation database 1320 and generates a funnel of one or more web interfaces, as discussed above. The MLCDN 1604 then delivers the web interfaces to the user devices 1602 for frontend presentation to the end users (e.g., for live use by end users). Accordingly, a standard CDN is improved to generate algorithmically evolved web interfaces.

Example Results

During the live online evaluation 108, the performance measures 106 are gathered for each of the funnels based on user interaction 324. In some implementations, the interaction metadata can be tracked for each user on a session-by-session basis. For example, for each of the interacting users like user_m, user_j, user_(j+1), and user_n, corresponding sessions interaction_im, interaction_ij, interaction_i(j+1), and interaction_in can be created during the live online evaluation 108. During these sessions, funnels corresponding to candidate individuals like individual_i, individual_i+1, and individual_n can be presented to the users and evaluated in parallel. Based on the user interaction 324, the performance measures 106 for each of the candidate individuals can be collected and developed.

FIG. 17 graphically illustrates a control individual and a winning individual, and comprising dimensions and dimension values. In the example shown in FIG. 17, the best performing winning headline page element is shown along with the control banner.

Figure 18:
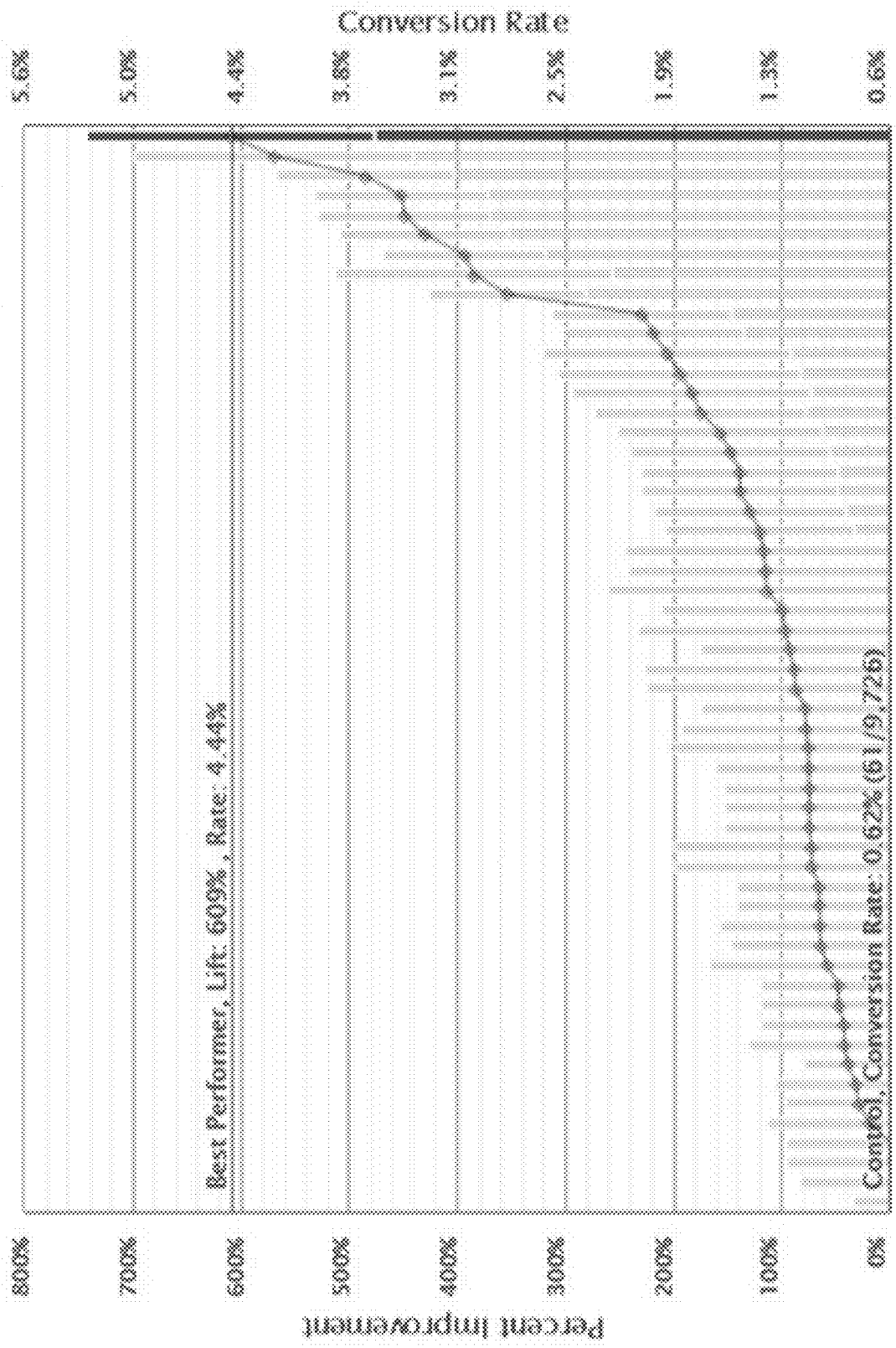
FIG. 18 is a chart that graphically illustrates example results of one implementation of the disclosed evolutionary computations.

FIG. 18 is a chart that graphically illustrates example results of one implementation of the disclosed evolutionary computations carrying out the MLCO. In FIG. 18, the chart shows that the best performing winning headline page element of FIG. 17 can improve the conversion rate from nearly 0% to 4.44%.

Risk Tolerance & Population Segmentation

Figure 19:
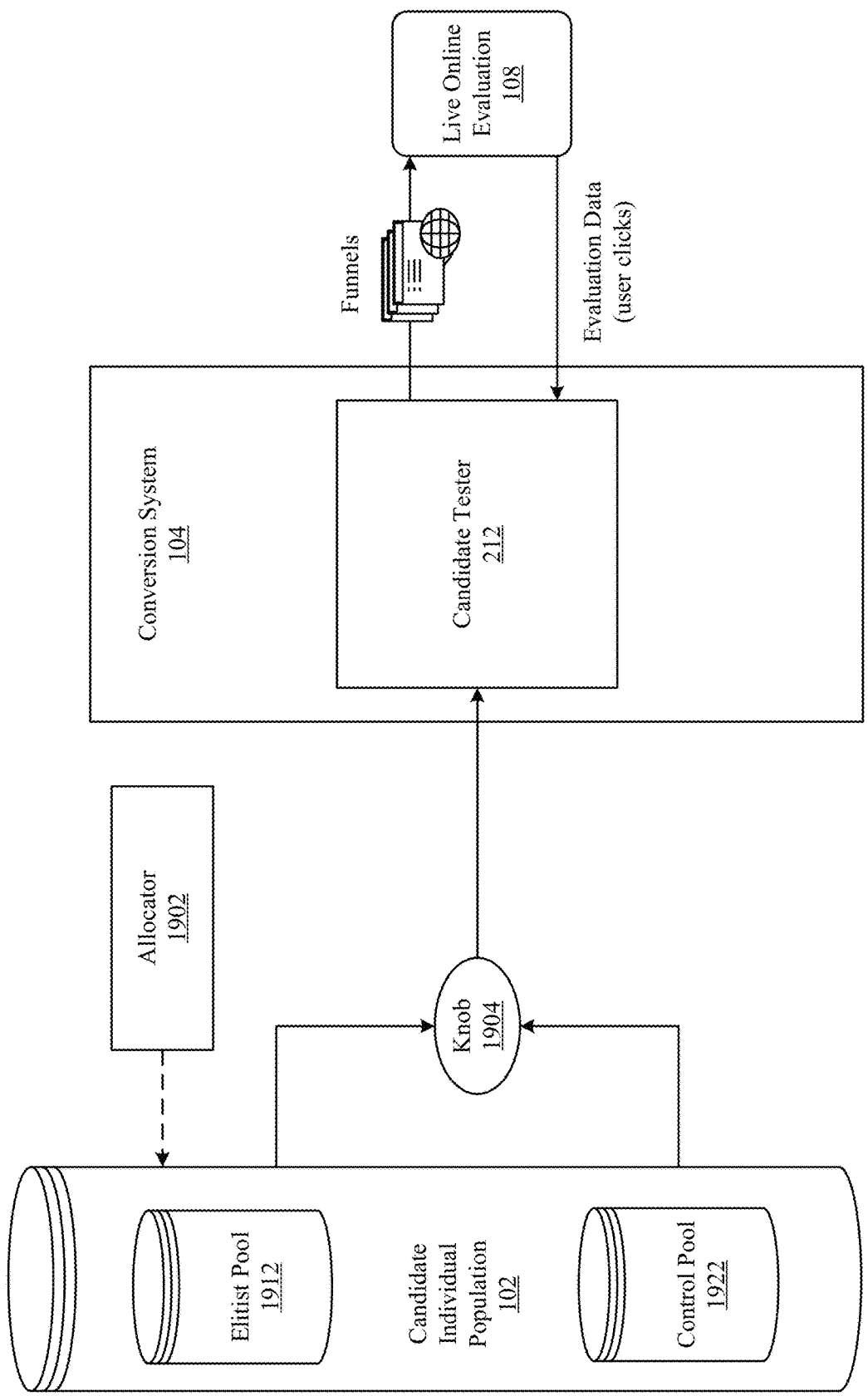
FIG. 19 shows one implementation of a risk tolerance module that implements risk tolerance for the disclosed evolutionary computations and an allocation module that segments the candidate population.

Existing conversion optimization solutions, which involve live testing on real users, sometimes are cancelled in the very early stages when they cause conversions to drop. The risk and returns of conversion optimization are "inversely related". As a result, the MLCO disclosed herein provides systems and methods of increasing conversions within the scope of the desired risk tolerance. FIG. 19 shows one implementation of a risk tolerance module that implements risk tolerance for the disclosed evolutionary computations. In the example shown in FIG. 19, the risk tolerance module is depicted in the form of a knob 1904 that can serve as a configurable parameter accessible across an administrative interface.

In one implementation, a risk tolerance level is specified that determines what percentage or amount of the live user traffic (i.e., what number of users) is presented algorithmically evolved funnels or candidate individuals and what percentage or amount of the live user traffic (i.e., what number of users) is presented control funnels or candidate individuals. For example, at a conservative risk tolerance level, only 5% of the webpages served to the user are determined by the evolutionary computations, whereas 95% of the webpages are control versions. In other implementations, different risk tolerance levels can be specified such as moderately conservative (e.g., 15% evolved webpages, 85% control webpages), moderate (e.g., 20% evolved webpages, 80% control webpages), moderately aggressive (e.g., 60% evolved webpages, 40% control webpages), and aggressive (e.g., 70% evolved webpages, 30% control webpages). For each of these risk tolerance levels, appropriate division of user exposure to algorithmically evolved candidate individuals and control candidate individuals can be set.

In one implementation, candidate individuals in the candidate individual population 102 can be segmented by an allocation module 1902 into multiple groups or pools in dependence upon a plurality of heuristics. Examples of such heuristics include how good a candidate individual is based on the performance measures (e.g., conversion rate or revenue rate), how experienced a candidate individual is based on the degree of live user evaluation or how recently a candidate individual was created or how many generations a candidate individual has survived or the number of times a candidate individual has been preserved due to being selected into the elitist pool, or whether the candidate individual is a control individual based on designer specification.

In one implementation, a first population group within the candidate population comprises only of control individuals, a second population group with the candidate population comprises only of elite individuals, a third population within the candidate population comprises only of non-elite pre-existing individuals (i.e., formed in a previous generation), and a fourth population within the candidate population comprises only of newly formed individuals (i.e., formed in a current generation).

Depending on the configuration of the knob 1904, frequency of alternative deployment of candidate individuals from an elitist pool 1912 and a control pool 1922 can be set. For example, if the knob 1904 is set at 20%, then the conversion system 104 accesses and deploys candidate individuals from the control pool 1922 80% of the time. In other implementations, different access frequency rules can be set that will be readily apparent to those skilled in the art.

Additionally, the live user traffic can be allocated to various groups or pools of the candidate population by the candidate tester 212 working in conjunction with the knob 1904. In one example, 50% of the live user traffic can be assigned to control individuals in a control pool, 30% of the liver user traffic can be assigned to elite individuals in an elite pool (e.g., the fittest members of the previous generation and preserved into the next generation), and 20% of the live user traffic can be assigned to non-elite individuals (e.g., recently created offspring genomes) in a non-elite pool. Furthermore, varied distribution of the live user traffic across different segments of the candidate population can be used by organizations to implement risk tolerance schemes. For instance, since elite individuals are superior to control individuals, an aggressive risk tolerance scheme can include routing a majority of the live user traffic to elite individuals in the elite pool and routing only minority of the live user traffic to the control pool and the non-elite pool. For example, 60% of the live user traffic can be assigned to the elite pool, 20% of the liver user traffic can be assigned to the control pool, and 20% of the live user traffic can be assigned to the non-elite pool. With such a scheme, because more users will be exposed to elite web interfaces, the organizational performance measures (e.g., organizational conversion rate or organizational revenue rate) improve faster. Similarly, in other implementations, conservative or semi-aggressive or semi-conservative schemes can be selected and/or implemented by the organizations.

In yet other implementations, different heuristics can be used to segment the candidate population (e.g., weighted probability, region, domain name, department within an organization, etc.), such that the live user traffic can be variedly distributed to the different segments, groups, pools, or clusters of the candidate population defined by the heuristics.

Selecting a Winner

Given that many candidates are produced and saved in the candidate individual population 102 during an evolutionary run, eventually a winning candidate or candidates should be chosen for long term implementation.

Turning back to FIG. 2, the winner selector 112, as controlled by the controller 230, selects a winner or multiple winners for implementation after the evolutionary algorithm is complete (i.e., after the genes are finished evolving). The winner selector 112 will perform "winner selection" to select one or more candidates from the candidate individual population 102.

One problem is that performance of the candidates has been estimated through sampling up to this point. This creates a multiple hypothesis problem, meaning that a candidate that seems to perform the best may have simply gotten lucky during the sampling (i.e., the creating of the candidate individual population 102 and/or the elitist pool 1912). As a result, a candidate that seems to be the best might perform poorly in the future in long term implementation.

A solution to this problem includes solving three sub-problems: (1) decide which candidate or candidates are the best candidate or candidates, (2) estimate performance of the best candidate or candidates and (3) confirm that the performance of the best candidate or candidates is statistically significantly better that that of other candidates, including control candidates.

There are potentially several ways to solve these problems, including age-layering (see Shahrzad et al., Estimating the Advantage of Age-Layering in Evolutionary Algorithms, 2016; incorporated herein by reference), performing successive A/B tests on the best candidates (see Kohavi et al., Online Controlled Experiments and A/B Tests, 2016; incorporated herein by reference) and nonparametric functional estimation (see Shahrzad et al., Nonparametric Functional Estimation, 2014; incorporated herein by reference). The technology disclosed implements a varied version of non-parametric functional estimation. As previously mentioned, the winner selector 112 performs the "winner selection" as a post-processing step to evolution, such that it does not affect the evolution itself. Further, the "winner selection" does not require additional sampling beyond that done during evolution. This provides an advantage, because in practice, evolution may have to be terminated at any time based on customer request, and a good candidate needs to be delivered without further testing. In practice such termination often happens early, before evolution has fully converged, when candidate fitnesses still vary significantly (i.e., the estimates are uncertain and are unreliable and/or stochastic). This amplifies the need for reliable and accurate "winner selection." Other implementations of selecting a winner can include selecting multiple winners at a given point to populate a new pool and/or to completely repopulate the candidate individual population 102.

Determining the Best Candidate and Estimating Performance

The first two sub-problems (i.e., deciding which candidate is the best candidate and estimating performance of the best candidate) can be solved by relying on a smoothness assumption. The technology disclosed implements a smoothness assumption by assuming that similar candidates have similar performance. Evolutionary computation in general relies on this assumption, such that small mutations (i.e., local search) are assumed to result in small changes in performance. With smoothness, it is then possible to estimate the performance of a candidate by averaging the performance of all candidates in its neighborhood:

$$f_{N,x}=1/k\Sigma_{i=1}^{k}f_{C,i} \quad \text{[EQUATION 1]}$$

In EQUATION 1, $f_{N,x}$ is the neighborhood fitness (neighborhood performance measure) of candidate x and $f_{C,i}$ is the candidate fitness (i.e., performance estimated through sampling) of candidate i among the k candidates in its neighborhood. In other words, the neighborhood performance measure of a particular candidate individual is given by the performance measures of (i) the particular candidate individual and (ii) K neighborhood candidate individuals which are nearest in the candidate pool to the particular candidate individual according to a predefined definition of nearness, and where K>0.

Regarding lucky candidates (i.e., the candidate fitness is overestimating its realistic performance), the neighborhood fitness evens out the score. For example, even if the candidate itself may have gotten lucky, its neighborhood is likely to contain both lucky and unlucky candidates. This neighborhood fitness, therefore, is more reliable and can be used as a more realistic estimate of the candidate's performance, and thereby to identify good candidates. The definition of a neighborhood (nearness) can be based on distance or k-nearest neighbors in any space, such as a metric space (e.g., a metric-genotype space) or a vector space (e.g., a vector-genotype space). Distances between candidates can be measured using Euclidean distance and using other calculations known to a person of ordinary skill in the art, such as cosine distance, etc. A neighborhood can be defined to include all neighbor candidates within a certain (predefined) distance or to include the k-nearest neighbors based on the distance. Other embodiments can use different types of measurements to determine distance for purposes of defining a neighborhood. Embedding spaces, metric spaces, vector spaces, and genotypes spaces are described in U.S. patent application Ser. No. 14/494,346, entitled "VISUAL INTERACTIVE SEARCH," (incorporated herein by reference). Since evolution converges the population around good candidates, it is likely that there are a large enough number of candidates in good neighborhoods. Thus, the neighborhood fitness can be used to select good candidates and estimate their future performance better than candidate fitness. Additionally, neighborhood fitness can be calculated differently for different segments of the candidate population (e.g., weighted probability, region, domain name, department within an organization, etc.). Additionally, in other implementations segmentation could be performed in, at least, two ways: (i) in the traditional way where segments are defined before we begin the evolution, such that there are separate evolutionary processes for each segment, and each one is like the one described here; and (ii) auto-segmentation where each candidate is actually a neural network that maps users to optimal webpages (e.g., instead of a page, the candidates are neural network mappings). As such, neighborhood fitness can be applied in multiple evolutionary optimization processes, where each process optimizes pages for one segment, and neighborhood fitness can also be applied to evolution of pages themselves, or mappings from user segments to optimal pages for each segment.

Figure 20A:
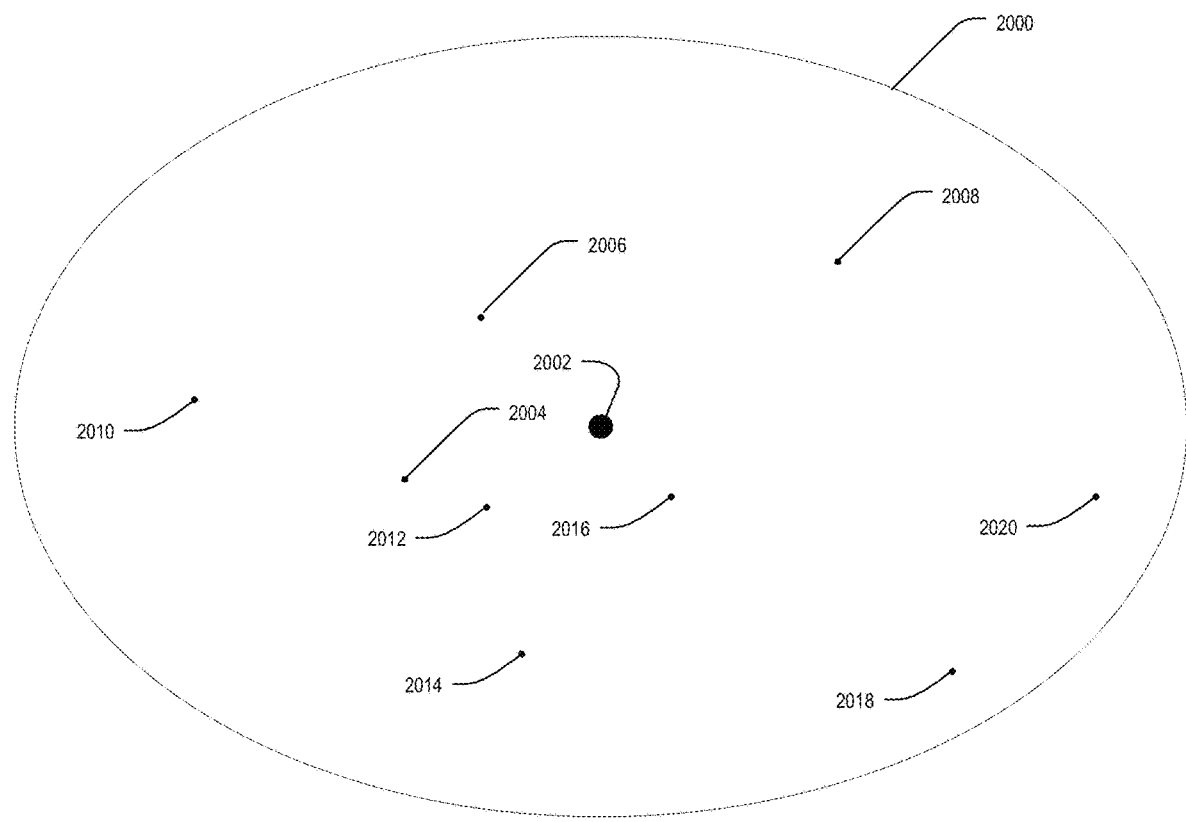
FIG. 20A illustrates an example embedding space having candidate individuals.
Figure 20B:
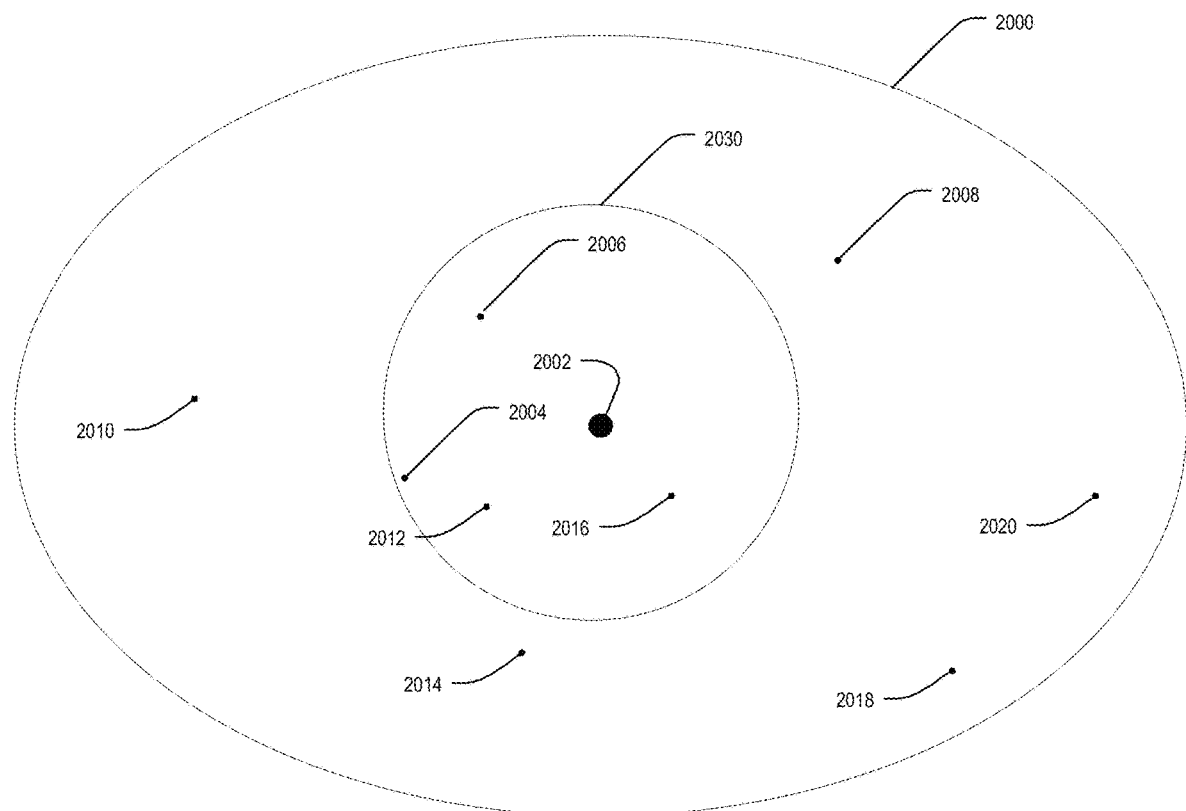
FIG. 20B illustrates an example embedding space and a neighborhood formed within the embedding space.

An example two-dimensional embedding space and creation of a neighborhood is illustrated in FIGS. 20A and 20B.

Referring to FIG. 20A, a candidate list 2000 is illustrated as including candidates 2002, 2004, 2006, 2008, 2010, 2012, 2014, 2016, 2018 and 2020, also referred to as "the group of candidates." Each candidate of the group of candidates is illustrated as a point in the embedding space. Candidate 2002 is at or near the center or origin of the embedding space for illustrative and explanatory purposes. The group of candidates is an example of a subset of candidates from the candidate individual population 102 and/or the elitist pool 1912. As described earlier, each of the candidates of the group of candidates has a fitness score. Note that candidate list 2000 represented in FIG. 20A is represented in a two-dimensional embedding space for ease of illustration and explanation. In many implementations the embedding space is a multi-dimensional space.

Referring to FIG. 20B, a neighborhood 2030 is formed around candidate 2002. The size and location of the neighborhood 2030 can be determined using a variety of methods known to a person of ordinary skill in the art. As mentioned above, the size/location of the neighborhood 2030 can be based on k-nearest neighbors of candidate 2002 in the embedding space.

Alternatively, a mechanism for determining the size and location of the neighborhood 2030 can implement a clustering algorithm to select a discriminative subset of the candidate list 2000 with respect to candidate 2002. Such a mechanism may use a clustering algorithm such as k-means, or k-medoids to identify clusters of similar candidates in the candidate list 2000 with respect to the candidate 2002. See http://en.wikipedia.org/wiki/K-means_clustering (visited 2 Feb. 2018) and http://en.wikipedia.org/wiki/K-medoids (visited 2 Feb. 2018), both incorporated by reference herein.

The example illustrated in FIG. 20B happens to have candidate 2002 at the center of the neighborhood 2030, but this is not always the case. Other implementations my include utilizing algorithms that will shift a symmetrically sized neighborhood 2030 in a certain direction so as to be able to include an increased number or a decreased number of candidates within the neighborhood 2030, as opposed to leaving the neighborhood 2030 centered around candidate 2002. This neighborhood 2030 need not be symmetrical and can be shaped/defined using other methods not described herein that would be apparent to a person of ordinary skill in the art. For example, as mentioned above, the neighborhood 2030 can be defined a different manner, such as, by radius, number of nearest neighbors, and/or through a weighted scheme according to how important each dimension between genomes is in affecting the fitness. Also, in different embodiments the population may consist of every candidate created in the entire evolutionary run, or only those in the last generation Once the neighborhood 2030 surrounding candidate 2002 is defined, the average fitness score of the entire neighborhood 2030 can be calculated. This average fitness score can be calculated using EQUATION 1, as described above. The best candidate, e.g., candidate B, can be identified using these techniques. In other words, this above-described approach solves the first two problems.

Estimating Performance of the Best Candidate

The third sub-problem, i.e. confirming that the best candidate is statistically significantly better than other candidates, including the control candidate, can be solved in two confirmatory steps. In the first confirmatory step, the probability that the performance of the best candidate B is due to luck is estimated. The probability that candidate B was identified as the best candidate as a result of luck can be determined using, for example, a permutation test. Other methods of determining the probability of a score being the best as the results of luck will be readily apparent to a person skilled in the art. This probability is hereinafter referred to a probability p1. The permutation test can be performed by repeating the following four permutation steps, M times.

The first permutation step is to permute the samples assigned to candidates, i.e. assign+/−labels in the same proportions as seen during evolution. This is called a permutation test. The permutation test is performed by randomly assigning "+" and "−" labels to the candidates, where a "+" label represents a conversion and a "−" label represents a non-conversion. For example, suppose that for a population of Z total candidates, X conversions (i.e., X candidates with a "+" label) and Y non-conversions (i.e., Y candidates with a "−" label) were observed during testing. In this situation, the permutation test will assign X conversion and Y non-conversions randomly to the Z candidates. This assignment is performed M times, as mentioned below to achieve a baseline rate (e.g., how often would the candidate convert if all candidates were equally good).

The second permutation step is to calculate the neighborhood fitness of each candidate using EQUATION 1, as discussed above.

The third permutation step is to find the candidate with the best neighborhood fitness in this permutation of samples.

The fourth permutation step is to increment a counter S if the candidate found in the third step has a neighborhood fitness that is equal to or better than that of candidate B.

After the permutation test has been performed M times, the probability p1 that performance as good as that of candidate B could have been observed by chance (luck), given the multiple hypotheses, is p1=S/M [EQUATION 2].

The second confirmatory step will test whether the performance of candidate B is significantly better than that of control. Control is one specific candidate C, which is likely to be tested more than the other candidates. Accordingly, the standard fitness score/calculation can be used for control candidate C, rather than determining the neighborhood fitness of candidate C. Note that the standard fitness score and the performance of control candidate C is still a random variable. The probability that the performance observed for candidate B is better than that of candidate C can be estimated by comparing (i) an observed means of a binomial distribution using candidate B and (ii) an observed means of a binomial distribution using candidate C. A comparison of both of the observed means can be used to identify a probability p2 that the binomial distribution of candidate B is the same as the binomial distribution of candidate C.

Next, the probability that candidate B is better than control candidate C (e.g. probability $P_{BC}$) is calculated using $(1-p1)(1-p2)$ [EQUATION 3]. Specifically, the probably $P_{BC}=(1-p_1)(1-p_2)$. This probability can be used to confirm the performance of the winning candidate or candidates.

Evaluation and Confirmation of Candidates

The methods described above for identifying the best candidate or candidates using neighborhood fitness can be verified using an 11-multiplexer function (see Miikkulainen, et al. How to Select a Winner in Evolutionary Optimization?, IEEE Symposium Series in Computational Intelligence, 2017; incorporated by reference) (see Shahrzad et al., Tackling the Boolean Multiplexer Function Using a Highly Distributed Genetic Programming System, 2015; incorporated herein by reference). Specifically, the 11-multiplexer function can be used to determine True Fitness of a candidate over many evolutions of that candidate. Then the True Fitness scores over the evolution of that candidate can be compared to fitness scores of that same candidate and also the neighborhood fitness score of that same candidate. An example is provided below with respect to how the accuracy of the candidate fitness using neighborhood fitness can be verified. This example is described in further detail and additional examples are provided in "How to Select a Winner in Evolutionary Optimization."

Figure 21:
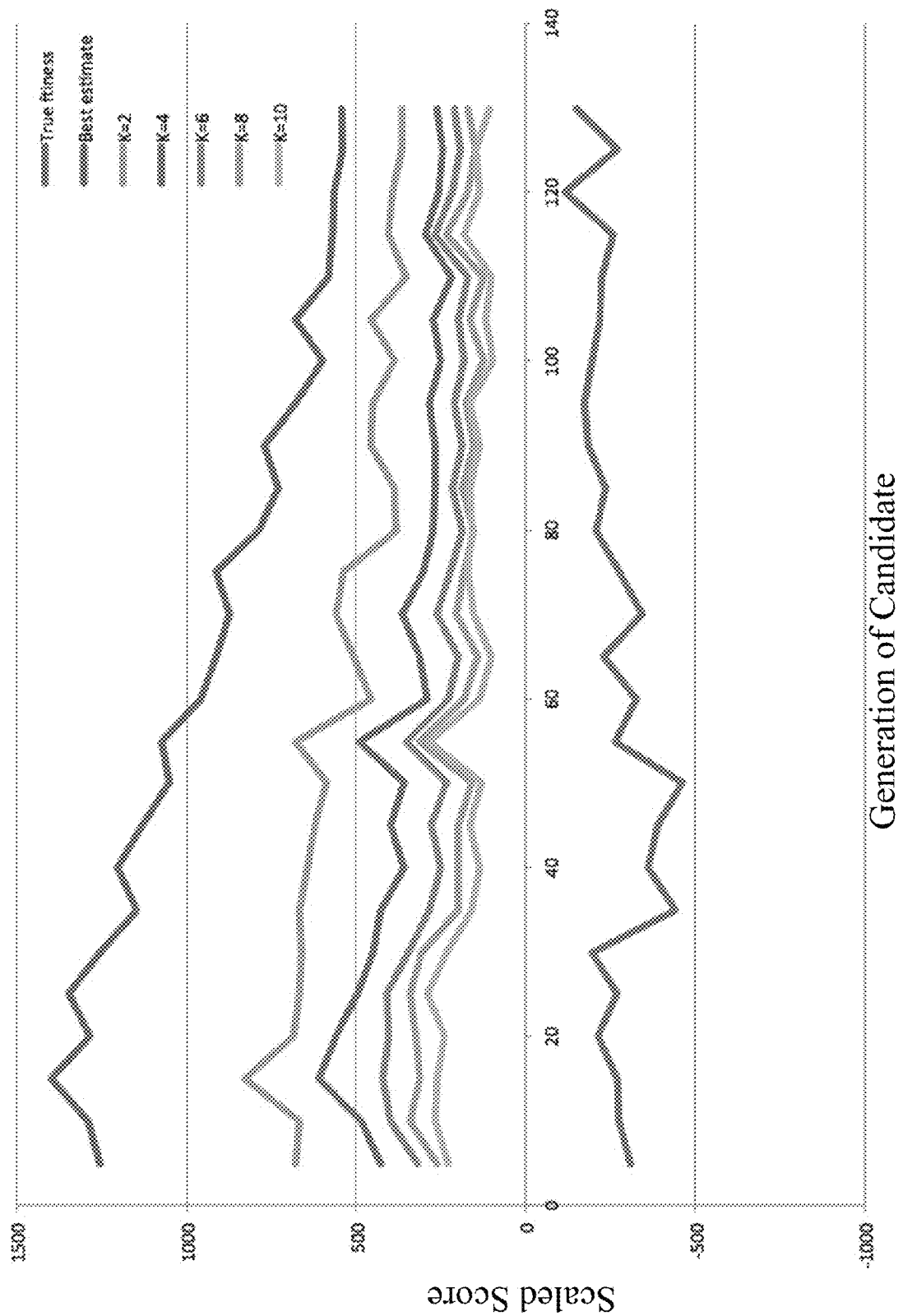
FIG. 21 illustrates scaled performance/fitness scores over various generations of a candidate individual.

FIG. 21 illustrates a graph of scaled scores (see Y-AXIS) vs. number of evolutions (see X-AXIS) for a particular candidate. The scores are scaled and the candidate or candidates are evolved as described in "How to Select a Winner in Evolutionary Optimization."

Referring to FIG. 21, scored results are provided for a particular candidate over many evolutions (generations), where each colored line represents a plot obtained using a different scoring technique. Specifically, seven scoring techniques are illustrated. One of the seven scoring techniques is the True Fitness, which represents the actual fitness score of a particular webpage. True Fitness is the score too which the other fitness scores are compared. Another of the seven scoring techniques is the Best Estimate, which represents the fitness score (without using neighborhood fitness) of the particular candidate at each generation. The remaining scoring techniques are Neighborhood Fitness scores represented as K=2, K=4, K=6, K=8 and K=10. The value of "K" represents the number of nearest neighbors along with the candidate itself. For example, the Neighborhood Fitness score for K=2 represents the neighborhood fitness score of the particular candidate using two of the nearest neighbors, and the Neighborhood Fitness score for K=10 represents the neighborhood fitness score of the particular candidate using ten of the nearest neighbors.

As illustrated in FIG. 21, the Best Estimate plot is consistently the furthest away from the True Fitness plot. Each of the Neighborhood Fitness plots is closer to the True Fitness plot than the Best Estimate plot, meaning that the Neighborhood Fitness plots are more accurate with respect to the True Fitness. Within the various Neighborhood Fitness plots, the plot represented as K=10 is closest to the True Fitness plot. As the number of generations of the particular candidate increase, the Best Estimate plot and the Neighborhood Fitness plots all begin to converge towards the True Fitness plot. However, the Neighborhood Fitness plot K=10 is consistently closer to the True Fitness plot.

Computer System

Figure 22:
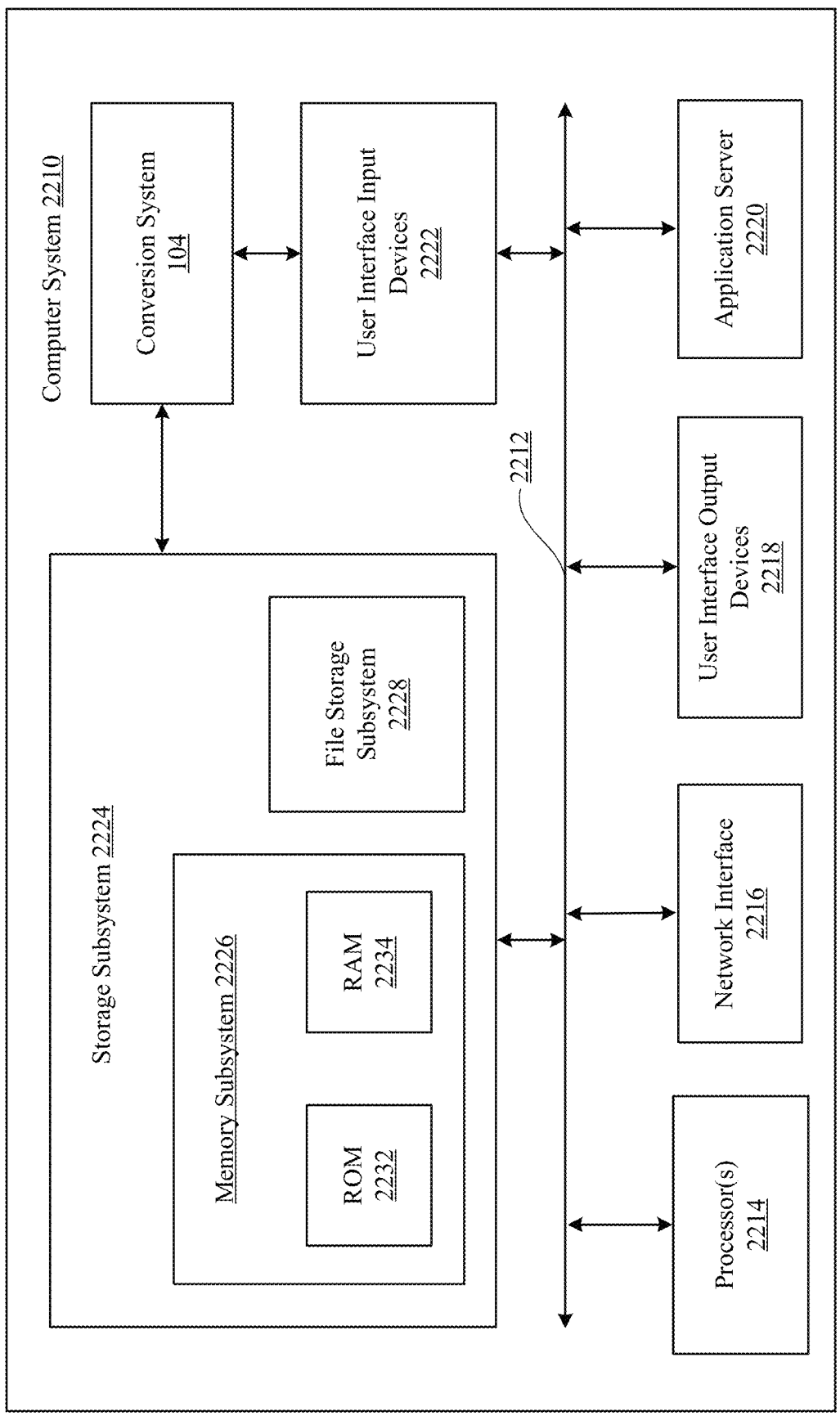
FIG. 22 is a simplified block diagram of a computer system that can be used to implement the technology disclosed.

FIG. 22 is a simplified block diagram of a computer system that can be used to implement the technology disclosed. Computer system 2210 typically includes at least one processor 2214 that communicates with a number of peripheral devices via bus subsystem 2212. These peripheral devices can include a storage subsystem 2224 including, for example, memory devices and a file storage subsystem, user interface input devices 2222, user interface output devices 2218, and a network interface subsystem 2216. The input and output devices allow user interaction with computer system 2210. Network interface subsystem 2216 provides an interface to outside networks, including an interface to corresponding interface devices in other computer systems.

In one implementation, the conversion system 104 is communicably linked to the storage subsystem 2224 and a user interface input devices 2222.

User interface input devices 2222 or clients or client devices can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2210.

User interface output devices 2218 can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2210 to the user or to another machine or computer system.

Storage subsystem 2224 stores programming and data constructs that provide the functionality of some or all of the modules and methods described herein. These software modules are generally executed by processor 2214 alone or in combination with other processors.

Memory 2226 used in the storage subsystem can include a number of memories including a main random access memory (RAM) 2234 for storage of instructions and data during program execution and a read only memory (ROM) 2232 in which fixed instructions are stored. A file storage subsystem 2228 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2228 in the storage subsystem 2224, or in other machines accessible by the processor.

Bus subsystem 2212 provides a mechanism for letting the various components and subsystems of computer system 2210 communicate with each other as intended. Although bus subsystem 2212 is shown schematically as a single bus, alternative implementations of the bus subsystem can use multiple busses. Application server 2220 can be a framework that allows the applications of computer system 2210 to run, such as the hardware and/or software, e.g., the operating system.

Computer system 2210 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 2210 depicted in FIG. 22 is intended only as a specific example for purposes of illustrating the preferred embodiments of the present invention. Many other configurations of computer system 2210 are possible having more or less components than the computer system depicted in FIG. 20.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

What is claimed is:

1. A computer-implemented method for finding an optimal funnel for converting web users through machine learned evolutionary optimization of genetic algorithms, the computer-implemented method comprising:
- storing, in a memory, a population of candidate funnels in a candidate pool, wherein each candidate funnel includes one or more webpages;
- a candidate processing module evolving the candidate funnels in the candidate pool by performing machine learned evolution steps including:
- testing by a candidate testing module each candidate funnels of the population of candidate funnels to obtain test results;
- assigning by the candidate testing module a performance measure to the tested candidate funnels in dependence upon the test results, wherein the performance measure is a relative performance measure calculated based on a difference between an absolute performance measure of a control funnels in a time period and an absolute performance measure of the candidate funnels in the time period;
- discarding by a competition module candidate funnels from the candidate pool in dependence upon their assigned relative performance measure; and
- adding, to the candidate pool, a new candidate funnel procreated by a procreation module from candidate individuals remaining in the candidate pool after the discarding of the candidate funnels, wherein the new candidate funnel is procreated in accordance with a machine learned genetic algorithm by crossing over two or more parent individuals on a gene-by-gene basis;
- repeating the machine learned evolution steps to evolve the candidate funnels in the candidate pool over multiple generations;
- a winner selector selecting, as a winning candidate funnel, a candidate funnel from the candidate pool having a best neighborhood performance measure, where the neighborhood performance measure of a particular candidate funnel is given by an average of the relative performance measures of (i) the particular candidate funnel and (ii) K neighborhood candidate funnels which are nearest in the candidate pool to the particular candidate funnel according to a predefined definition of nearness, and where K>0, the average being calculated as follows:

$$f_{N,x} = 1/k \Sigma_{i=1}^{k} f_{C,i}$$

wherein $f_{N,x}$, is the neighborhood performance measure of candidate funnel x and $f_{C,i}$ is a candidate performance measure of candidate i among k candidates in x's neighborhood; and
- a machine learned computer system confirming that the selected winning candidate funnel is statistically better than other candidate funnels by determining at least one of:
- (i) a probability that the selected winning candidate funnel was identified as having a best neighborhood performance measure by luck; and
- (ii) whether performance of the selected winning candidate funnel is better than performance of a control candidate funnel;
- wherein the selected winning candidate funnel is a solution to the provided problem.

2. The computer-implemented method of claim 1, wherein the winning candidate funnel is selected by:
- selecting a candidate funnel having a highest computed neighborhood performance measure.

3. The computer-implemented method of claim 1, wherein the new candidate funnel is added to the candidate pool, such that genes for the new candidate funnel are fitness-proportionally selected from parent candidate funnels remaining in the candidate pool.

4. The computer-implemented method of claim 3, wherein the new candidate funnel is procreated by mutating at least one parent funnel on a gene-by-gene basis.

5. The computer-implemented method of claim 3, wherein the new candidate funnel is added by mutation only after being procreated by crossover.

6. The computer-implemented method of claim 1, wherein the performance measure of a subject candidate funnel is determined based on a difference between an absolute performance measure of a control candidate funnel determined in a first time period and an absolute performance measure of the subject candidate funnel determined in the first time period.

7. The computer-implemented method of claim 1, wherein the computer-implemented method further comprises:
- segmenting by an allocation module the population of candidate funnels into multiple population groups based on a plurality of heuristics; and
- wherein the evolution steps are only performed on a sub-set of the segmented population of candidate funnels, such that every segment of the population of candidate funnels is not evolved.

8. The computer-implemented method of claim 1, wherein each candidate funnel identifies a value for each of a plurality of dimensions of the one or more webpages.

9. The computer-implemented method of claim 8, wherein the identified values for the plurality of dimensions represent different characteristics of the one or more webpages.

10. The computer-implemented method of claim 8, wherein the selected winning candidate funnel represents a candidate funnel determined to be the most likely to successfully achieve conversion of end users.

11. The computer-implemented method of claim 1, wherein:
- each webpage represented by the candidate funnels has a plurality of dimensions, each having a value; and
- the webpage represented by the selected winning candidate funnel is to be implemented for live use by end users.

12. The computer-implemented method of claim 1, wherein each candidate funnel of the candidate pool belongs to a metric space and the predefined definition of nearness is based on distances between the particular candidate funnel and other candidate funnels of the candidate pool.

13. The computer-implemented method of claim 12, wherein the distances are Euclidean distances determined in dependence upon dimensions of the candidate funnels of the candidate pool.

14. The computer-implemented method of claim 12, wherein K=10, such that the nearest 10 candidate funnels to the particular candidate funnel are selected for determining the neighborhood performance measure.

15. The computer-implemented method of claim 12, wherein a predefined distance in the metric space is selected and all candidate funnels of the candidate pool that are within the predefined distance from the particular candidate funnel are selected for determining the neighborhood performance measure.

16. The computer-implemented method of claim 12, wherein the performance measure is a conversion rate obtained by testing a candidate funnel using a predefined number of samples.

17. The computer-implemented method of claim 1, wherein the selecting of the winning candidate funnel includes selecting N candidate funnels having the highest neighborhood performance measures, where N>1.

18. The computer-implemented method of claim 17, further comprising:
discarding all other candidate funnels from the candidate pool, except for the N candidate funnels; and
performing the evolving, the repeating, and the selecting of the winning candidate funnel.

19. A non-transitory computer-readable recording medium having instructions recorded thereon for finding an optimal funnel for converting web users through machine learned evolutionary optimization of genetic algorithms, the instructions, when executed by a processor of a computer, causing the computer to execute a method comprising:
storing, in a memory, a population of candidate funnels in a candidate pool, wherein each candidate funnel includes one or more webpages;
evolving by a candidate processing module the candidate funnels in the candidate pool by performing machine learned evolution steps including:
testing by a candidate testing module each candidate funnels of the candidate individuals to obtain test results;
assigning by the candidate testing module a performance measure to the tested candidate funnels in dependence upon the test results, wherein the performance measure is a relative performance measure calculated based on a difference between an absolute performance measure of a control funnel in a time period and an absolute performance measure of the candidate funnel in the time period;
discarding by a competition module candidate funnels from the candidate pool in dependence upon their assigned relative performance measure; and
adding by a procreation module, to the candidate pool, a new candidate funnel procreated from candidate funnels remaining in the candidate pool after the discarding of the candidate funnels, wherein the new candidate funnel is procreated in accordance with a machine learned genetic algorithm by crossing over two or more parent funnels on a gene-by-gene basis;
repeating the machine learned evolution steps to evolve the candidate funnels in the candidate pool over multiple generations; and
selecting, by a winner selector, as a winning candidate funnel, a candidate funnel from the candidate pool having a best neighborhood performance measure, where the neighborhood performance measure of a particular candidate funnel is given by an average of the relative-performance measures of (i) the particular candidate funnel and (ii) K neighborhood candidate funnels which are nearest in the candidate pool to the particular candidate funnel according to a predefined definition of nearness, and where K>0, the average being calculated as follows:

$$f_{N,x} = 1/k \Sigma_{i=1}^{k} f_{C,i}$$

wherein $f_{N,x}$ is the neighborhood performance measure of candidate funnel x and $f_{C,i}$ is a candidate performance measure of candidate i among k candidates in x's neighborhood; and a machine learned computer system confirming that the selected winning candidate funnel is statistically better than other candidate funnels by determining at least one of:
(i) a probability that the selected winning candidate funnel was identified as having a best neighborhood performance measure by luck; and
(ii) whether performance of the selected winning candidate funnel is better than performance of a control candidate funnel;
wherein the selected winning candidate funnel is a solution to the provided problem.

20. A computer-implemented system for finding an optimal funnel for converting web users a solution to a provided problem by selecting a winning candidate individual through machine learned evolutionary optimization of genetic algorithms, the computer-implemented system comprising:
a memory storing a population of candidate funnels in a candidate pool, wherein each candidate funnel includes one or more webpages;
a candidate processing module for evolving the candidate funnels in the candidate pool by performing machine learned evolution steps including:
a candidate testing module for testing each candidate funnel of the candidate funnels to obtain test results and assigning a performance measure to the tested candidate funnels in dependence upon the test results, wherein the performance measure is a relative performance measure calculated based on a difference between an absolute performance measure of a control funnel in a time period and an absolute performance measure of the candidate funnel in the time period; a competition module for discarding candidate funnels from the candidate pool in dependence upon their assigned relative performance measure;
a procreation module for adding, to the candidate pool, a new candidate funnel procreated from candidate funnels remaining in the candidate pool after the discarding of the candidate funnels, wherein the new candidate funnel is procreated in accordance with a machine learned genetic algorithm by crossing over two or more parent funnels on a gene-by-gene basis;
repeating the machine learned evolution steps to evolve the candidate funnels in the candidate pool over multiple generations; and a winner selector for selecting, as a winning candidate funnel, a candidate funnel from the candidate pool having a best neighborhood performance measure, where the neighborhood performance measure of a particular candidate funnel is given by an average of the relative performance measures of (i) the particular candidate funnel and (ii) K neighborhood candidate funnels which are nearest in the candidate pool to the particular candidate funnel according to a predefined definition of nearness, and where K>O, the average being calculated as follows:

$$f_{N,x} = 1/k \Sigma_{i=1}^{k} f_{C,i}$$

wherein $f_{N,x}$ is the neighborhood performance measure of candidate funnel x and $f_{C,i}$ is a candidate performance measure of candidate i among k candidates in x's neighborhood; and
a machine learned computer system confirming that the selected winning candidate funnel is statistically better than other candidate funnels by determining at least one of:

(i) a probability that the selected winning candidate funnel was identified as having a best neighborhood performance measure by luck; and
(ii) whether performance of the selected winning candidate funnel is better than performance of a control candidate funnel;
wherein the selected winning candidate funnel is a solution to the provided problem.

21. The computer-implemented method of claim 9, wherein one characteristic of the different characteristics of the webpage represented by the values for the plurality of dimensions is a color of a portion of the webpage.

\* \* \* \* \*